(12) United States Patent
Dravid

(10) Patent No.: US 12,246,058 B2
(45) Date of Patent: Mar. 11, 2025

(54) METHODS AND COMPOSITIONS FOR TREATING PAIN

(71) Applicant: Creighton University, Omaha, NE (US)

(72) Inventor: Shashank Dravid, Omaha, NE (US)

(73) Assignee: Creighton University, Omaha, NE (US)

( * ) Notice: Subject to any disclaimer, the term of this patent is extended or adjusted under 35 U.S.C. 154(b) by 1085 days.

(21) Appl. No.: 17/153,165

(22) Filed: Jan. 20, 2021

(65) Prior Publication Data

US 2021/0379152 A1 Dec. 9, 2021

Related U.S. Application Data

(60) Provisional application No. 62/963,253, filed on Jan. 20, 2020.

(51) Int. Cl.
*A61K 38/19* (2006.01)
*A61P 25/02* (2006.01)
*A61P 25/04* (2006.01)

(52) U.S. Cl.
CPC ............ *A61K 38/191* (2013.01); *A61P 25/02* (2018.01); *A61P 25/04* (2018.01)

(58) Field of Classification Search
None
See application file for complete search history.

(56) References Cited

U.S. PATENT DOCUMENTS

| | | | |
|---|---|---|---|
| 5,122,458 A | 6/1992 | Post et al. | |
| 5,168,062 A | 12/1992 | Stinski | |
| 7,213,538 B2 | 5/2007 | Han et al. | |
| 2006/0040354 A1 | 2/2006 | O'Keefe | |

FOREIGN PATENT DOCUMENTS

| WO | WO 1998/010088 | 3/1998 |
|---|---|---|
| WO | WO 2005/073384 | 8/2005 |

OTHER PUBLICATIONS

Zhong, W., Barde, S., Mitsios, N., Adori, C., Oksvold, P., von Feilitzen, K., O'Leary, L., Csiba, L., Hortobagy, T., Szocsics, P., Mechawar, N., Magloczky, Z., Renner, E., Palkovits, M., Uhlen, M., Mulder, J., Hokfet, T. The neuropeptide landscape of human prefrontal cortex. PNAS. 2022. 119(33) 1-12. (Year: 2022).*
Burbach, J.P.H., Neuropeptides from concept to online database www.neuropeptides.nl. 2010. European Journal of Pharmacology. 626:27-48. (Year: 2010).*
Sabnis, S., Narasimhan, K., Chettiar P., Gakare, S., Shelkar, G., Asati, D., Thakur, Dravid, S., Intravenous recombinant cerebellin 1 treatment restores spinal glutamate delta 1 receptor signalingand mitigates chronic pain. British Journal of Pharmacology. Dec. 3, 2023. doi: 10.1111/bph.16296, (Year: 2023).*
Sandor, K., Krishnan, S., Mohan Agalave, N., Krock, E., Villarreal Salcido, J., Fernandez-Zafra, T., Khoonsari, P., Svensson, C., Kultima, K. Spinal injection of newly identified cerebellin-1 and cerebellin-2 peptides induce mechanical hypersensitivity in mice. Neuropeptides. 2018. 53-59. (Year: 2018).*
Krishnan et al. Autism gene Ube3a and seizures impair sociability by repressing VTA Cbln1. Nature. 2017. 543:507-512. (Year: 2017).*
Cherny et al. Opioid Pharmacotherapy in the Management of Cancer Pain. A Survey of Strategies Used by Pain Physicians for the Selection of Analgesic Drugs and Routes of Administration. 1995. Cancer. 76(7):1283-1293. (Year: 1995).*
Glare et al. Pain in Cancer Survivors. 2014. J Clin Oncol 32(16): 1739-1747. (Year: 2014).*
Elegheert, Kakegawa, Clay, Shanks, Behiels, Matsuda, Kohda, Miura, Rossmann, Mitakidis, Motohashi, Chang, Siebold, Greger, Nakagawa, Yuzaki, Aricescu, A., Structural basis for integration of GluD receptors within synaptic organizer complexes. Science. 2016. 353(6296) 295-299. (Year: 2016).*
Elegheert, et al., Supplementary Information. A., Structural basis for integration of GluD receptors within synaptic organizer complexes. Science. 2016. 353(6296) 1-67. (Year: 2020).*
Gandhi, P., 2020. Organisation of Glutamatergic Inputs to Central Amygdala. ProQuest No. 28021786. Doctoral Dissertation, Creighton University. (Year: 2020).*
Quintao, N., Santin, J., Stoeberl, L., Correa, T., Melato, J., Costa, R., Pharmacological Treatment of Chemotherapy-Induced Neuropathic Pain: PPARγ Agonists as a Promising Tool. Frontiers. 2019. 13: 1-17. (Year: 2019).*
Sandor et al. Spinal injection of newly identified cerebellin-1 and cerebellin-2 peptides induce mechanical hypersensitivity in mice. Neuropeptides. 2018; 69:53-59. (Year: 2018).*
Allen et al., "Left and right hemispheric lateralization of the amygdala in pain," Prog Neurobiol, 2021,196: 14 pages.
Arbuthnot et al., "In vitro and in vivo hepatoma cell-specific expression of a gene transferred with an adenoviral vector," Human gene therapy, Aug. 20, 1996, 7(13):1503-1514.
Asokan et al., "The AAV vector toolkit: poised at the clinical crossroads," Molecular Therapy, Apr. 1, 2012, 20(4):699-708.
Batt et al., "Characterization of the polyomavirus late polyadenylation signal," Molecular and cellular biology, Sep. 1, 1995, 15(9):4783-4790.
Bird et al., "Protein kinase A-dependent enhanced NMDA receptor function in pain-related synaptic plasticity in rat amygdala neurones," The Journal of physiology, May 2005, 564(3):907-921.
Boshart et al., "A very strong enhancer is located upstream of an immediate early gene of human cytomegalovirus," Cell, Jun. 1, 1985, 41(2):521-530.
Boulikas et al. "Nature of DNA sequences at the attachment regions of genes to the nuclear matrix.," Journal of cellular biochemistry, May 1993, 52(1):14-22.

(Continued)

Primary Examiner — Daniel E Kolker
Assistant Examiner — Maureen Varina Driscoll
(74) Attorney, Agent, or Firm — Fish & Richardson P.C.

(57) ABSTRACT

The disclosure provides polypeptides and pharmaceutical compositions thereof. Such polypeptides can be useful, for example, in treating pain in a subject. In some embodiments, the polypeptides are useful for treating neuropathic and/or inflammatory pain.

13 Claims, 31 Drawing Sheets
(31 of 31 Drawing Sheet(s) Filed in Color)
Specification includes a Sequence Listing.

(56) References Cited

OTHER PUBLICATIONS

Braz et al., "Parallel "pain" pathways arise from subpopulations of primary afferent nociceptor.," Neuron, Sep. 15, 2005, 47(6):787-793.
Carrasquillo et al., "Activation of the extracellular signal-regulated kinase in the amygdala modulates pain perception," Journal of Neuroscience, Feb. 14, 2007, 27(7):1543-1551.
Chen et al., "Expression of rat bone sialoprotein promoter in transgenic mice," Journal of bone and mineral research, May 1996, 11(5):654-664.
Cheng et al., "Role of extracellular signal-regulated kinase in synaptic transmission and plasticity of a nociceptive input on capsular central amygdaloid neurons in normal and acid-induced muscle pain mice," Journal of Neuroscience, Feb. 9, 2011, 31(6):2258-2270.
Colloca et al., "Neuropathic pain," Nat Rev Dis Primers, Feb. 16, 2017, 3:17002, 19 pages.
De Lacalle et al., "Calcitonin gene-related peptide-like immunoreactivity marks putative visceral sensory pathways in human brain," Neuroscience, Sep. 7, 2000, 100(1):115-130.
Delgado et al., "Validation of digital visual analog scale pain scoring with a traditional paper-based visual analog scale in adults," Journal of the American Academy of Orthopaedic Surgeons, Global research & reviews, Mar. 2018, 2(3): 1-6.
D'Hanis et al., "Topography of thalamic and parabrachial calcitonin gene-related peptide (CGRP) immunoreactive neurons projecting to subnuclei of the amygdala and extended amygdala," Journal of Comparative Neurology, Nov. 20, 2007, 505(3):268-291.
Dixon et al., "Staircase bioassay: the up-and-down method," Neuroscience & Biobehavioral Reviews, Mar. 1, 1991, 15(1):47-50.
Dobolyi et al., "Calcitonin gene-related peptide-containing pathways in the rat forebrain," Journal of Comparative Neurology, Aug. 15, 2005, 489(1):92-119.
Fisher et al., "Transduction with recombinant adeno-associated virus for gene therapy is limited by leading-strand synthesis," Journal of virology, Jan. 1, 1996, 70(1):520-532.
Gao et al., "Orphan glutamate receptor δ1 subunit required for high-frequency hearing," Molecular and cellular biology, Jun. 15, 2007, 27(12):4500-4512.
Gauriau et al., "Pain pathways and parabrachial circuits in the rat," Experimental physiology, Mar. 2002, 87(2):251-258.
Gossen et al., "Tight control of gene expression in mammalian cells by tetracycline-responsive promoters," Proceedings of the National Academy of Sciences., Jun. 15, 1992, 89(12):5547-5551.
Gossen et al., "Transcriptional activation by tetracyclines in mammalian cells. Science," Jun. 23, 1995, 268(5218): 5 pages.
Hagedorn et al., "S/MAR element facilitates episomal long-term persistence of adeno-associated virus vector genomes in proliferating cells," Human gene therapy, Dec. 1, 2017, 28(12): 29 pages.
Han et al., "Elucidating an affective pain circuit that creates a threat memory," Cell, Jul. 16, 2015, 162(2): 13 pages.
Hansal et al., "Cutting edge: Induction of antigen-specific hyporesponsiveness by transplantation of hemopoietic cells containing an MHC class I transgene regulated by a lymphocyte-specific promoter," The Journal of Immunology, Aug. 1, 1998, 161(3): 7 pages.
Harvey et al., "Inducible control of gene expression: prospects for gene therapy," Current opinion in chemical biology, Jan. 1, 1998, 2(4):512-518.
Hepp et al., "Glutamate receptors of the delta family are widely expressed in the adult brain," Brain Structure and Function, Sep. 2015, 220(5):2797-2815.
Iijima et al., "Activity-dependent repression of Cbln1 expression: mechanism for developmental and homeostatic regulation of synapses in the cerebellum," Journal of Neuroscience, Apr. 29, 2009, 29(17):5425-5434.
Iijima et al., "SAM68 regulates neuronal activity-dependent alternative splicing of neurexin-1," Cell, Dec. 23, 2011, 147(7):1601-1614.
Ikeda et al., "NMDA receptor-independent synaptic plasticity in the central amygdala in the rat model of neuropathic pain," Pain, Jan. 1, 2007, 127(1-2):161-172.
Ji et al., "5-HT2C receptor knockdown in the amygdala inhibits neuropathic-pain-related plasticity and behaviors," Journal of Neuroscience, Feb. 8, 2017, 37(6):1378-1393.
Ji et al., "Fear extinction learning ability predicts neuropathic pain behaviors and amygdala activity in male rats," Molecular pain, Oct. 2018, 14: 1-13.
Kidd et al., "Mechanisms of inflammatory pain," British journal of anaesthesia, Jul. 1, 2001, 87(1):3-11.
Kim et al., "An experimental model for peripheral neuropathy produced by segmental spinal nerve ligation in the rat. Pain," Sep. 1, 1992, 50(3):355-363.
Konno et al., "Enriched expression of GluD1 in higher brain regions and its involvement in parallel fiber-interneuron synapse formation in the cerebellum," Journal of Neuroscience, May 28, 2014, 34(22):7412-7424.
Kruger et al., "Calcitonin gene-related peptide (CGRP) in the rat central nervous system: patterns of immunoreactivity and receptor binding sites," Brain research, Nov. 1, 1988, 463(2):223-244.
Lein et al. "Genome-wide atlas of gene expression in the adult mouse brain," Nature, Jan. 2007, 445(7124):168-176.
Levitt et al., "Definition of an efficient synthetic poly (A) site," Genes & Development, Jul. 1, 1989, 3(7):1019-1025.
Li et al., "Spared nerve injury differentially alters parabrachial monosynaptic excitatory inputs to molecularly specific neurons in distinct subregions of the central amygdala," Pain, Jan. 2020, 61(1):166-176.
Liu et al., "Modulation of burst firing of neurons in nucleus reticularis of the thalamus by GluN2C-containing NMDA receptors," Molecular pharmacology, Aug. 1, 2019, 96(2):193-203.
Liu wet al., "Striatal glutamate delta-1 receptor regulates behavioral flexibility and thalamostriatal connectivity," Neurobiology of disease, Apr. 1, 2020, 137:104746, 11 pages.
Lykken et al., "Recent progress and considerations for AAV gene therapies targeting the central nervous system," Journal of neurodevelopmental disorders, Dec. 2018, 10(1):1-10.
Magari et al., "Pharmacologic control of a humanized gene therapy system implanted into nude mice," The Journal of clinical investigation, Dec. 1, 1997, 100(11):2865-2872.
Miura et al., "Distinct expression of Cbln family mRNAs in developing and adult mouse brains," European Journal of Neuroscience, Aug. 2006, 24(3):750-760.
Naur et al., "Ionotropic glutamate-like receptor δ2 binds D-serine and glycine," Proceedings of the National Academy of Sciences, Aug. 28, 2007, 104(35):14116-14121.
Navratilova et al., "Selective modulation of tonic aversive qualities of neuropathic pain by morphine in the central nucleus of the amygdala requires endogenous opioid signaling in the anterior cingulate cortex," Pain, Mar. 1, 2020, 161(3): 39 pages.
Neugebauer et al., "The amygdala and persistent pain," The Neuroscientist, Jun. 2004, 10(3): 15 pages.
Neugebauer et al., "Synaptic plasticity in the amygdala in a model of arthritic pain: differential roles of metabotropic glutamate receptors 1 and 5," Journal of neuroscience, Jan. 1, 2003, 23(1):52-63.
Neugebauer, "Amygdala Pain Mechanisms," Handbook of Experimental Pharmacology, 2015, 227:261-284.
No et al., "Ecdysone-inducible gene expression in mammalian cells and transgenic mice," Proceedings of the National Academy of Sciences, Apr. 16, 1996, 93(8):3346-3351.
Orkin et al., "Thalassemia due to a mutation in the cleavage-polyadenylation signal of the human beta-globin gene," The EMBO journal, Feb. 1985, 4(2):453-456.
Otsuka et al., Roles of Cbln1 in non-motor functions of mice. Journal of Neuroscience. Nov. 16, 2016;36(46):11801-16.
Piccioli et al., "Neuroantibodies: ectopic expression of a recombinant anti-substance P antibody in the central nervous system of transgenic mice," Neuron, Aug. 1, 1995, 15(2):373-384.
Piccioli et al., "Neuroantibodies: molecular cloning of a monoclonal antibody against substance P for expression in the central nervous system," Proceedings of the National Academy of Sciences, Jul. 1, 1991, 88(13):5611-5615.

(56) References Cited

OTHER PUBLICATIONS

Powell et al., "Viral expression cassette elements to enhance transgene target specificity and expression in gene therapy," Discovery medicine, Jan. 1, 2015, 19(102): 15 pages.

Schek et al., "Definition of the upstream efficiency element of the simian virus 40 late polyadenylation signal by using in vitro analyses," Molecular and Cellular Biology, Dec. 1, 1992, 12(12):5386-5393.

Schwaber et al., "Neurons containing calcitonin gene-related peptide in the parabrachial nucleus project to the central nucleus of the amygdala," Journal of Comparative Neurology, Apr. 15, 1988, 270(3):416-426.

Seigneur et al., "Cerebellins are differentially expressed in selective subsets of neurons throughout the brain," Journal of Comparative Neurology, Oct. 15, 2017, 525(15):3286-3311.

Spike et al., "A quantitative and morphological study of projection neurons in lamina I of the rat lumbar spinal cord," European Journal of Neuroscience, Nov. 2003, 18(9):2433-2448.

Staff et al., "Chemotherapy-induced peripheral neuropathy: a current review," Annals of neurology, Jun. 2017, 81(6): 19 pages.

Stein et al., "The osteocalcin gene: a model for multiple parameters of skeletal-specific transcriptional control," Molecular biology reports, Aug. 1997, 24(3):185-196.

Sugimura et al., "Synaptic and network consequences of monosynaptic nociceptive inputs of parabrachial nucleus origin in the central amygdala," Journal of neurophysiology, Jun. 1, 2016, 115(6):2721-2739.

Szymanski et al., "Development and validation of a robust and versatile one-plasmid regulated gene expression system," Molecular Therapy, Jul. 1, 2007, 15(7):1340-1347.

Tao et al., "Postsynaptic δ1 glutamate receptor assembles and maintains hippocampal synapses via Cbln2 and neurexin," Proceedings of the National Academy of Sciences, Jun. 5, 2018, 115(23):E5373-E5381.

Thompson et al., "Amygdala plasticity and pain," Pain research & management, Dec. 10, 2017, 2017:8296501, 13 pages.

Thompson et al., "Small conductance calcium activated potassium (SK) channel dependent and independent effects of riluzole on neuropathic pain-related amygdala activity and behaviors in rats," Neuropharmacology, Aug. 1, 2018, 138:219-231.

Uemura et al., "Trans-synaptic interaction of GluRδ2 and Neurexin through Cbln1 mediates synapse formation in the cerebellum," Cell, Jun. 11, 2010, 141(6):1068-1079.

Varrassi et al., "Towards an effective and safe treatment of inflammatory pain: a Delphi-guided expert consensus," Advances in therapy, Oct. 2019, 36(10):2618-2637.

Wang et al., "Ligand-inducible and liver-specific target gene expression in transgenic mice," Nature biotechnology, Mar. 1997, 15(3):239-243.

Wang et al., "Positive and negative regulation of gene expression in eukaryotic cells with an inducible transcriptional regulator," Gene therapy, May 1997, 4(5):432-441.

Watabe et al., "Synaptic potentiation in the nociceptive amygdala following fear learning in mice," Molecular brain, Dec. 2013, 6(1):1-14.

Wei et al., "The Cbln family of proteins interact with multiple signaling pathways," Journal of neurochemistry, Jun. 2012, 121(5):717-729.

Wilson et al., "Dual and opposing functions of the central amygdala in the modulation of pain," Cell reports, Oct. 8, 2019, 29(2): 21 pages.

Woychik et al., "Requirement for the 3'flanking region of the bovine growth hormone gene for accurate polyadenylylation," Proceedings of the National Academy of Sciences, Jul. 1, 1984, 81(13):3944-3948.

Yadav et al., "Deletion of glutamate delta-1 receptor in mouse leads to enhanced working memory and deficit in fear conditioning," PloS one, Apr. 3, 2013, 8(4):e60785, 12 pages.

Yadav et al., "Mutations in the transmembrane domain M3 generate spontaneously open orphan glutamate delta 1 receptor," Brain research, Mar. 25, 2011, 1382:1-8.

Ye et al., "Cell-type specific parallel circuits in the bed nucleus of the stria terminalis and the central nucleus of the amygdala of the mouse," Brain Structure and Function, Apr. 2019, 224(3):1067-1095.

Younger et al., "Pain outcomes: a brief review of instruments and techniques," Current pain and headache reports, Feb. 1, 2009, 13(1):39-43.

Yuzaki et al., "A GluD coming-of-age story," Trends in neurosciences, Mar. 1, 2017, 40(3): 13 pages.

Yuzaki, "Two classes of secreted synaptic organizers in the central nervous system," Annual review of physiology, Feb. 10, 2018, 80:243-262.

Zhao et al., "Activity-dependent synaptic recruitment of neuroligin 1 in spinal dorsal horn contributed to inflammatory pain," Neuroscience, Sep. 15, 2018, 388:1-10.

\* cited by examiner

METHODS AND COMPOSITIONS FOR TREATING PAIN

CROSS-REFERENCE TO RELATED APPLICATIONS

This application claims the benefit of U.S. Provisional Application No. 62/963,253, filed Jan. 20, 2020, the contents of which are hereby incorporated by reference.

DESCRIPTION OF THE TEXT FILE SUBMITTED ELECTRONICALLY

The contents of the text file submitted electronically herewith are incorporated herein by reference in their entirety: A computer readable format copy of the Sequence Listing filename: 44264_0008001_ST25.txt, date created: Feb. 11, 2021 file size 15 kilobytes.

STATEMENT OF FEDERALLY SPONSORED RESEARCH

This invention was made with government support under Grant Nos. MH116003 and NS118731, awarded by National Institutes of Health's National Institute of Mental Health and National Institute of Neurological Disorders and Stroke, respectively. The government has certain rights in the invention.

TECHNICAL FIELD

The present disclosure is related to methods and compositions for treating pain using cerebellin 1 or a variant thereof.

BACKGROUND

Chronic pain is a debilitating condition involving neuronal dysfunction. Pain perception is essential for survival, but chronic pain can produce long-term disability and lead to precipitation of anxiety, depression, and cognitive impairment. Synaptic mechanisms underlying persistence of pain are still poorly understood.

The major "pain pathways" that process and transmit nociceptive information include the spinothalamic and spino-parabrachio-amygdaloid pathways (Gauriau et al. *Exp Physiol.* 2002; 87(2):251-8). In the spino-parabrachio-amygdaloid pathway, glutamatergic neurons in the external lateral parabrachial nucleus (PB) project to the lateral and capsular divisions of the central amygdala (CeLC), which have been termed the "nociceptive amygdala" and this region is critical for the integration of nociceptive and emotional-affective processing (see, e.g., Gauriau et al. *Exp Physiol.* 2002; 87(2):251-8; Braz et al. *Neuron.* 2005; 47:787-793; Spike et al. *Eur J Neurosci.* 2003; 18(9):2433-48; Neugebauer et al. *Handb Exp Pharmacol.* 2015; 227: 261-84; Thompson et al. *Pain Res Manag.* 2017; 2017: 8296501; and Neugebauer et al. *Neuroscientist.* 2004; 10(3): 221-34). Studies over the past two decades have shown functional plasticity at the parabrachio-amygdala synapses in the CeA as a mechanism for persistent and chronic pain (see, e.g., Thompson et al. Pain Res Manag. 2017; 2017: 8296501; Neugebauer et al. J Neurosci. 2003 Jan. 1; 23(1): 52-63; and Carasquillo et al. J Neurosci. 2007; 27(7):1543-51). Pain related functional changes such as increase in PB-CeLC neurotransmission and CeLC neuron hyperexcitability are documented in different pain models, including acute inflammatory pain and more persistent models such as neuropathic pain (see, e.g., Thompson et al. Pain Res Manag. 2017; 2017:8296501; Bird et al. *J Physiol.* 2005; 564(Pt 3): 907-921; Cheng et al. J Neurosci. 2011; 31(6): 2258-70; and Ikeda et al. *Pain.* 2007; 127(1-2): 161-72).

Neuropathic pain can be caused by a lesion or disease of the somatosensory system, and it is estimated to affect 7-10% of the general population (Colloca et al. *Nat Rev Dis Primers.* 2017; 3: 17002). Conditions associated with neuropathic pain include painful radiculopathy, postherpetic neuralgia, trigeminal neuralgia, leprosy, amputation, diabetic neuropathy, HIV infection, peripheral nerve injury pain, and stroke (Colloca et al. *Nat Rev Dis Primers.* 2017; 3: 17002). Neuropathic pain is also associated with increased drug prescriptions and visits to health care providers (Colloca et al. *Nat Rev Dis Primers.* 2017; 3: 17002). Chronic inflammatory pain includes pain hypersensitivity that accompanies inflammation (Kidd and Urban. *Br. J. Anaesth.* 2001; 87(1):3-11). Chronic inflammatory pain can result from, for example, arthritis, nerve injury, and tumor growth.

Despite advances, a significant knowledge gap remains in the understanding of the structural synaptic signaling under normal conditions and in pain conditions associated with dysfunction of PB-CeLC neurotransmission. Furthermore, there is a need to develop better, and safer, treatments for pain.

SUMMARY

Provided herein are methods of treating pain in a subject in need thereof, the method including administering to the subject a therapeutically effective amount of a polypeptide comprising at least 80% sequence identity to SEQ ID NO:2, or a pharmaceutical composition thereof.

In some embodiments, administration of the polypeptide or a pharmaceutical composition thereof increases glutamate delta 1 receptor (GluD1)-cerebellin 1 (Cbln1) signaling. In some embodiments, administration of the polypeptide or a pharmaceutical composition thereof increases GluD1 expression. In some embodiments, administration of the polypeptide or a pharmaceutical composition thereof reduces GluA1 expression.

Also provided herein are methods of increasing GluD1-Cbln1 signaling in a subject in need thereof, the method including administering to the subject a polypeptide having at least 80% sequence identity to SEQ ID NO:2, or a pharmaceutical composition thereof.

In some embodiments, the polypeptide comprises an amino acid sequence having at least 85% sequence identity to SEQ ID NO:2. In some embodiments, the polypeptide comprises an amino acid sequence having at least 90% sequence identity to SEQ ID NO:2. In some embodiments, the polypeptide comprises an amino acid sequence having at least 95% sequence identity to SEQ ID NO:2. In some embodiments, the polypeptide comprises an amino acid sequence having at least 98% sequence identity to SEQ ID NO:2. In some embodiments, the polypeptide comprises an amino acid sequence having at least 99% sequence identity to SEQ ID NO:2.

In some embodiments, the polypeptide comprises a substitution at one or more of the following amino acids: the asparagine at position 71, the histidine at position 72, the glutamate at position 73, the glutamate at position 76, the valine at position 121, the tyrosine at position 122, the arginine at position 124, the aspartate at position 147, the threonine at position 149, the aspartate at position 173, the methionine at position 177, the glycine at position 178, and the glycine at position 179, wherein the amino acid position is relative to SEQ ID NO:1.

In some embodiments, the tyrosine at position 122 of SEQ ID NO:2 is substituted with an amino acid selected from the group consisting of: aspartic acid and glutamic acid, wherein the amino acid position is relative to SEQ ID NO: 1. In some embodiments, the arginine at position 124 of SEQ ID NO:2 is substituted with a lysine, wherein the amino acid position is relative to SEQ ID NO:1. In some embodiments, the arginine at position 147 of SEQ ID NO:2 is substituted with a glutamic acid, wherein the amino acid position is relative to SEQ ID NO:1.

In some embodiments, the polypeptide comprises an amino acid sequence of SEQ ID NO:2.

In some embodiments, the pain comprises neuropathic pain, inflammatory pain, or a combination thereof. In some embodiments, the pain comprises neuropathic pain. In some embodiments, the neuropathic pain is associated with nerve compression, nerve damage, abnormal processing of pain signals, or a combination thereof. In some embodiments, the abnormal processing of pain signals is associated with phantom limb pain, postherpetic neuralgia, complex regional pain syndrome, or a combination thereof.

In some embodiments, the neuropathic pain is associated with surgery, trauma, a viral infection, cancer, a vascular malformation, alcoholism, a central nervous system disorder, a metabolic disorder, or a combination thereof. In some embodiments, the trauma comprises brain trauma or spinal cord trauma. In some embodiments, the central nervous system disorder is selected from the group consisting of multiple sclerosis, Parkinson's disease, Alzheimer's disease, stroke, and epilepsy. In some embodiments, the metabolic disorder is diabetes. In some embodiments, the neuropathic pain comprises central pain syndrome.

In some embodiments, the neuropathic pain is a side effect of a therapeutic agent. In some embodiments, the therapeutic agent is a chemotherapy. In some embodiments, the chemotherapy comprises a taxane, a platinum-based agent, a vinca alkaloid, an epothilone, eribulin, bortezomib, thalidomide, or a combination thereof.

In some embodiments, the subject has chemotherapy-induced neuropathic pain. In some embodiments, the subject was administered a chemotherapy comprising a taxane, a platinum-based agent, a vinca alkaloid, an epothilone, eribulin, bortezomib, thalidomide, or a combination thereof. In some embodiments, the taxane is selected from one or more of: paclitaxel, docetaxel, cabazitaxel, nab-paclitaxel, larotaxel, ortataxel, BMS-184476, tesetaxel, milataxel, taxoprexin, and opaxio. In some embodiments, the platinum-based agent is selected from one or more of: carboplatin, cisplatin, oxaliplatin, nedaplatin, lobaplatin, heptaplatin, satraplatin, picoplatin, liposomal cisplatin, and AP 5346. In some embodiments, the vinca alkaloid is selected from one or more of: vinblastine, vincristine, vindesine, and vinorelbine. In some embodiments, the epothilone is selected from one or more of: ixabepilone, epothilone A, epothilone B, epothilone C, epothilone D, epothilone E, and epothilone F.

In some embodiments, the pain comprises inflammatory pain. In some embodiments, the inflammatory pain is associated with surgery, trauma, arthritis, or a combination thereof.

In some embodiments, the pain is idiopathic.

In some embodiments, the subject is on an opioid-regimen. In some embodiments, the dosage of the opioid is decreased following administration of the polypeptide or a pharmaceutical composition thereof. In some embodiments, the method further comprises administering an opioid to the subject. In some embodiments, the subject is administered a lower dose of the opioid when administered in combination with the polypeptide compared to administration of the opioid alone. In some embodiments, the polypeptide or a pharmaceutical composition thereof and the opioid are administered as separate dosages sequentially in any order. In some embodiments, the polypeptide or a pharmaceutical composition thereof and the opioid are administered simultaneously as separate dosages.

In some embodiments, the polypeptide or a pharmaceutical composition thereof is administered to the central nervous system of the subject. In some embodiments, the polypeptide or a pharmaceutical composition thereof is administered intrathecally. In some embodiments, the polypeptide or a pharmaceutical composition thereof is administered intravenously. In some embodiments, the polypeptide or a pharmaceutical composition thereof is administered once every about 2 to about 4 weeks. In some embodiments, the polypeptide or a pharmaceutical composition thereof is administered during surgery.

Also provided herein are methods of treating pain in a subject in need thereof, the method including administering to the subject a therapeutically effective amount of a polypeptide that increases GluD1-Cbln1 signaling. In some embodiments, the polypeptide has about 20 to about 300 amino acids. In some embodiments, the polypeptide has about 250 to about 300 amino acids. In some embodiments, the polypeptide is a recombinant cerebellin 1 or a variant thereof. In some embodiments, the recombinant cerebellin 1 or a variant thereof has at least 80% sequence identity to SEQ ID NO:2.

Also provided herein are viral vectors having a coding sequence that encodes a polypeptide having at least 80% sequence identity to SEQ ID NO:2. In some embodiments, the viral vector is an AAV vector. In some embodiments, the AAV vector is an AAV serotype 1 vector (AAV1), an AAV serotype 2 vector (AAV2), an AAV serotype 1 and 2 hybrid vector (AAV1/2), an AAV serotype 3 vector (AAV3), an AAV serotype 4 vector (AAV4), an AAV serotype 5 vector (AAV5), an AAV serotype 6 vector (AAV6), an AAV serotype 7 vector (AAV7), an AAV serotype 8 vector (AAV8), or an AAV serotype 9 vector (AAV9). In some embodiments, the AAV vector is an AAV1 vector, an AAV2 vector, an AAV1/2 vector, an AAV4 vector, an AAV5 vector, an AAV8 vector, or an AAV9 vector.

In some embodiments, the viral vector comprises a regulatory sequence. In some embodiments, the regulatory sequence comprises a promoter. In some embodiments, the promoter is an inducible promoter, a constitutive promoter, or a tissue-specific promoter. In some embodiments, the promoter is the platelet-derived growth factor B-chain (PDGF-beta) promoter, the JC polymovirus promoter, the chicken β-actin (CBA) promoter, or the cytomegalovirus (CMV) promoter. In some embodiments, the regulatory sequence is a SV40 early enhancer/promoter element, a hybrid CMV enhancer/PDGF-beta promoter element, or a hybrid CMV enhancer/CBA promoter element. In some embodiments, the viral vector comprises a post-transcriptional regulatory element. In some embodiments, the viral vector comprises a scaffold attachment region sequence. In some embodiments, the viral vector comprises a polyadenylation signal sequence.

In some embodiments, the viral vector comprises a nucleic acid sequence of SEQ ID NO:7. In some embodiments, the viral vector comprises a nucleic acid sequence of SEQ ID NO:8.

Also provided herein are pharmaceutical compositions including any of the viral vectors described herein. In some embodiments, the pharmaceutical composition further includes a pharmaceutically acceptable excipient.

Also provided herein are kits including any of the viral vectors described herein or any of the pharmaceutical compositions thereof described herein.

In some embodiments, a kit provided herein further includes a pre-loaded syringe including any of the viral vectors described herein or any of the pharmaceutical compositions thereof described herein.

Also provided herein are methods of expressing a polypeptide that increases GluD1-Cbln1 signaling in a mammalian cell, the method including introducing any of the viral vectors described herein into the mammalian cell. In some embodiments, the mammalian cell is a neuron. In some embodiments, GluD1-Cbln1 signaling is increased at a synapse. In some embodiments, GluD1-Cbln1 signaling is increased at a parabrachio-central laterocapsular amygdala glutamatergic synapse.

Also provided herein are kits including: (i) any of the pharmaceutical compositions described herein; and (ii) instructions for performing any of the methods described herein.

Reference to the term "about" has its usual meaning in the context of compositions to allow for reasonable variations in amounts that can achieve the same effect and also refers herein to a value of plus or minus 10% of the provided value. For example, "about 20" means or includes amounts from 18 to and including 22.

As used herein, the terms "at least a portion" or "fragment" of a nucleic acid or polypeptide means a portion having the minimal size characteristics of such sequences, or any larger fragment of the full length molecule, up to and including the full length molecule.

As used herein, the term "amino acid modification" refers to, e.g., an amino acid substitution, deletion, and/or insertion, as is well understood in the art.

As used herein, "treatment" or "treating" of a disease, disorder, or condition encompasses alleviation of at least one symptom thereof, a reduction in the severity thereof, or the delay or inhibition of the progression thereof. Treatment need not mean that the disease, disorder, or condition is totally cured. A useful polypeptide or composition herein needs only to reduce the severity of a disease, disorder, or condition, reduce the severity of one or more symptoms associated therewith, or improve a patient or subject's quality of life.

As used herein, "preventing" refers to a reduction in risk of the onset, recurrence or spread, in whole or in part, of the disease or condition as described herein, or a symptom thereof.

The term "therapeutically effective amount" as used herein, means that amount of polypeptide or pharmaceutical agent that elicits the biological or medicinal response in a tissue system, animal or human that is being sought by a researcher, veterinarian, medical doctor or other clinician, which includes alleviation of the symptoms of the disease or disorder being treated. In particular, a therapeutically effective amount, when administered to a subject in need of such treatment, is sufficient to (i) treat or prevent a particular disease, condition, or disorder which can be treated with a polypeptide described herein, (ii) attenuate, ameliorate, or eliminate one or more symptoms of the particular disease, condition, or disorder, or (iii) prevent or delay the onset of one or more symptoms of the particular disease, condition, or disorder described herein. The amount of one or more polypeptides as provided herein that will correspond to such a therapeutically effective amount will vary depending upon factors such as the disease condition and its severity, the identity (e.g., weight) of the mammal in need of treatment, but can nevertheless be routinely determined by one skilled in the art.

The term "excipient" or "pharmaceutically acceptable excipient" means a pharmaceutically-acceptable material, composition, or vehicle, such as a liquid or solid filler, diluent, carrier, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, e.g., *Remington: The Science and Practice of Pharmacy, 21st ed.*; Lippincott Williams & Wilkins: Philadelphia, PA, 2005; *Handbook of Pharmaceutical Excipients*, 6th ed.; Rowe et al., Eds.; The Pharmaceutical Press and the American Pharmaceutical Association: 2009; *Handbook of Pharmaceutical Additives*, 3rd ed.; Ash and Ash Eds.; Gower Publishing Company: 2007; *Pharmaceutical Preformulation and Formulation*, 2nd ed.; Gibson Ed.; CRC Press LLC: Boca Raton, F L, 2009.

The terms "percent identity" or "identity" in the context of two or more nucleic acids or polypeptides, refers to the measurement of the similarity between the two or more sequences. The percent identity can be measured by any method known to one of skill in the art including using a sequence comparison software, an algorithm, and by visual inspection.

The term "subject" as used herein, refers to an animal, preferably a mammal, most preferably a human, who has been the object of treatment, observation or experiment. In some embodiments, the subject has experienced and/or exhibited at least one symptom of the disease or disorder to be treated and/or prevented. In some embodiments, a patient is a pediatric patient (i.e., a patient under the age of 21 years at the time of diagnosis or treatment).

Unless otherwise required by context, singular terms shall include pluralities and plural terms shall include the singular. As used herein, the singular form "a", "an", and "the" include plural references unless indicated otherwise. For example, "an" excipient includes one or more excipients. It is understood that aspects and variations of the invention described herein include "consisting of" and/or "consisting essentially of" aspects and variations.

The details of one or more embodiments of the invention are set forth in the accompanying drawings and the description below. Other features, objects, and advantages of the invention will be apparent from the description and drawings, and from the claims.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

DESCRIPTION OF DRAWINGS

The patent or application file contains at least one drawing executed in color. Copies of this patent or patent application publication with color drawing(s) will be provided by the Office upon request and payment of the necessary fee.

FIGS. 18A-18C are plots showing no change in mechanical threshold in Von Frey analysis in control (non-CFA injected) paw. Control for experiments in FIGS. 13-16.

DETAILED DESCRIPTION

Figure 1:
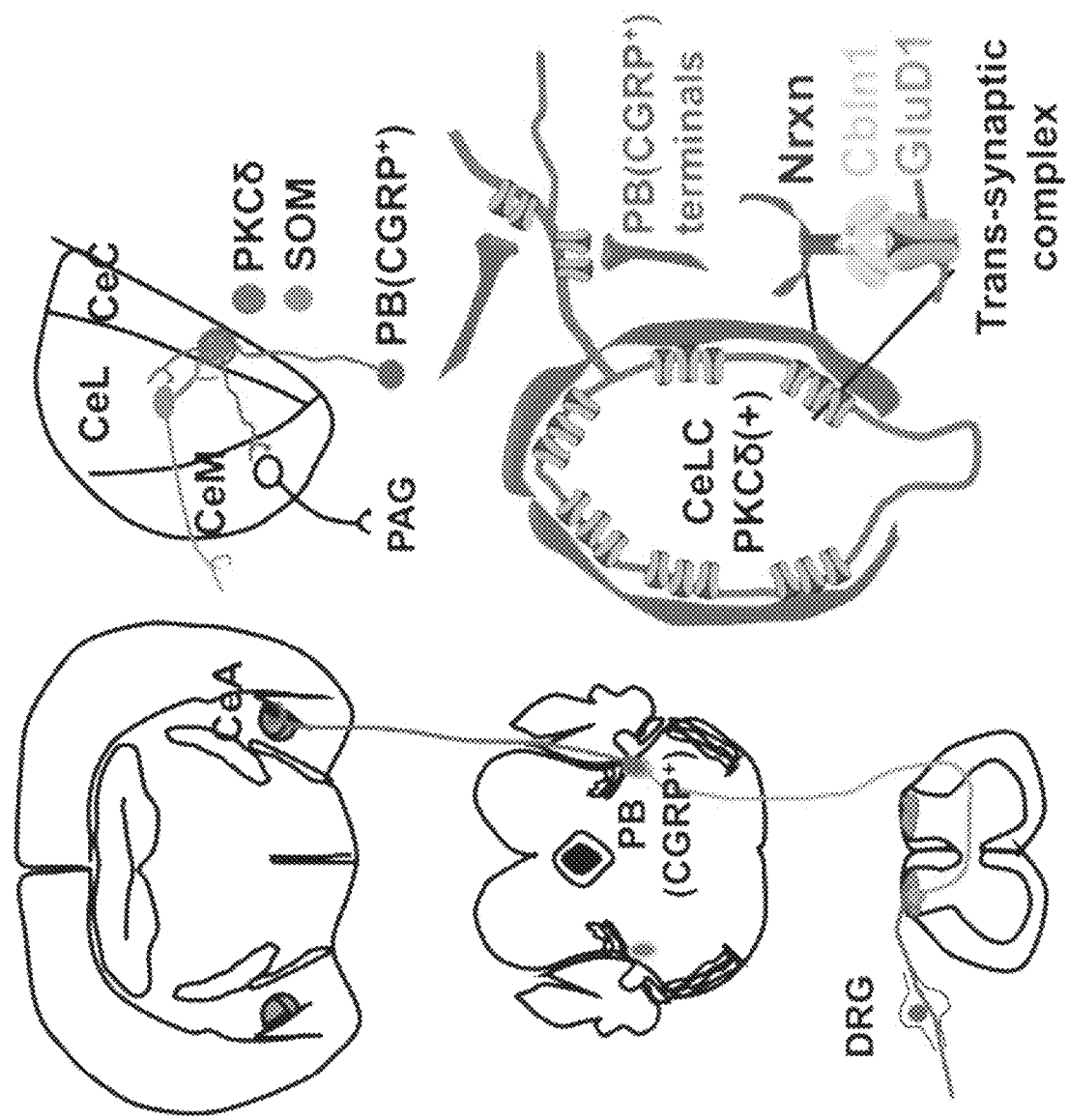
FIG. 1 is a schematic representation of parabrachio-amygdalar pathway.

This document provides compositions and methods for treating subjects in need thereof (e.g., subjects having pain) using a cerebellin polypeptide or a variant or fragment thereof. Cerebellins (Cbln) are secreted glycoproteins that belong to the C1q and tumor necrosis factor (TNF) superfamily (Kishore et al. *J Comp Neurol.* 2017; 525(15): 3286-3311). Cerebellins can function as trans-synaptic cell-adhesion molecules and contribute to the formation and/or function of synapses (Kishore et al. *J Comp Neurol.* 2017; 525(15): 3286-3311). Via Cbln1 released from presynaptic terminals, glutamate receptor deltas (GluDs) are involved in synapse formation and maintenance through interactions with presynaptic Neurexin. As shown herein, the transsynaptic GluD1-Cbln1 complex is a substrate for pain plasticity and pain persistence, and this complex undergoes aberrant changes in pain states. Furthermore, increasing GluD1-Cbln1 signaling can restore synaptic function. In some embodiments, the methods provided herein include increasing GluD1-Cbln1 signaling in the subject. In some embodiments, the methods provided herein include increasing GluD1 expression in the subject. In some embodiments, the methods provided herein include reducing GluA1 expression in the subject. Such methods can be useful, for example, for treating pain in a subject in need thereof by administering a therapeutically effective amount of a Cbln1 polypeptide or a variant or fragment thereof.

The full-length Clbn1 protein encoded by the *Homo sapiens* genomic sequence is 193 amino acids in length (e.g., SEQ ID NO:1, encoded by SEQ ID NO:7). Residues 1-21 are a signal peptide that is cleaved in vivo to produce a mature protein of 172 amino acids (e.g., SEQ ID NO:2; encoded by SEQ ID NO:8). Non-limiting exemplary amino acid sequences for Cbln1 are provided below.

TABLE 1

Exemplary amino acid sequences for Cbln1

| Description | SEQ ID NO. | Amino Acid Sequence |
|---|---|---|
| Full Cbln1 | 1 | MLGVLELLLLGAAWLAGPARGQNETEPIVLEGKC LVVCDSNPTSDPTGTALGISVRSGSAKVAFSAIR STNHEPSEMSNRTMIIYFDQVLVNIGNNFDSERS TFIAPRKGIYSFNFHVVKVYNRQTIQVSLMLNGW PVISAFAGDQDVTREAASNGVLIQMEKGDRAYLK LERGNLMGGWKYSTFSGFLVFPL |
| Mature Cbln1 | 2 | QNETEPIVLEGKCLVVCDSNPTSDPTGTALGISV RSGSAKVAFSAIRSTNHEPSEMSNRTMIIYFDQV LVNIGNNFDSERSTFIAPRKGIYSFNFHVVKVYN RQTIQVSLMLNGWPVISAFAGDQDVTREAASNGV LIQMEKGDRAYLKLERGNLMGGWKYSTFSGFLVF PL |

In some embodiments, a polypeptide described herein includes a polypeptide of SEQ ID NO:1 or a variant thereof (see Table 1). Variant polypeptides differ from another polypeptide and/or from one another by a small number of amino acid residues (e.g., they differ by no more than about 40 amino acid residues). The amino acid positions used to describe the Clbn1 amino acid modifications herein are based on the full Cbln1 amino acid sequence of SEQ ID NO:1. For example, a variant of SEQ ID NO:1 can be a polypeptide with about 1, about 2, about 3, about 4, about 5, about 6, about 7, about 8, about 9, about 10, about 15, about 20, about 25, about 30, about 35, or about 40 amino acid modifications relative to SEQ ID NO:1.

In some embodiments, the variant can be at least 50%, 55%, 60%, 65%, 70%, 75%, 80%, 85%, 90%, 91%, 92%, 93%, 94%, 95%, 96%, 97%, or 98% identical to SEQ ID NO:1. Examples of amino acid modifications with respect to the amino acid sequence set forth in SEQ ID NO:1, include, without limitation, amino acid substitutions, amino acid deletions, and amino acid insertions. In some embodiments, the variant can be at least 50%, 55%, 60%, 65%, 70%, 75%, 80%, 85%, 90%, 91%, 92%, 93%, 94%, 95%, 96%, 97%, or 98% identical to SEQ ID NO:2. In some embodiments, the polypeptide comprises an amino acid sequence having SEQ ID NO:1. In some embodiments, the polypeptide comprises an amino acid sequence having SEQ ID NO:2.

In some embodiments, an amino acid substitution of SEQ ID NO:1 or SEQ ID NO:2 can be a conservative amino acid substitution. For example, conservative amino acid substitutions can be made by substituting one amino acid residue for another amino acid residue having a similar side chain (see Table 2). Families of amino acid residues having similar side chains can also include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine).

TABLE 2

Chemically Related Amino Acid Side Chains

| | |
|---|---|
| Positively-Charged Side Chains | Lysine, Arginine, Histidine |
| Negatively-Charged Side Chains | Glutamate and Aspartate |
| Nonpolar and/or Aliphatic Side Groups | Glycine, Alanine, Valine, Leucine, Isoleucine, and Proline |
| Polar, Uncharged Side Groups | Serine, Threonine, Cysteine, Methionine, Asparagine, Glutamine |
| Aromatic Side Chains | Phenylalanine, Tyrosine, and Tryptophan |

In some embodiments, an amino acid substitution of SEQ ID NO:1 or SEQ ID NO:2 can be a non-conservative amino acid substitution. Non-conservative amino acid substitutions can be made by substituting one amino acid residue for another amino acid residue having a dis-similar side chain. Examples of non-conservative substitutions include, without limitation, substituting (a) a hydrophilic residue (e.g., serine or threonine) for a hydrophobic residue (e.g., leucine, isoleucine, phenylalanine, valine, or alanine); (b) a cysteine or proline for any other residue; (c) a residue having a basic side chain (e.g., lysine, arginine, or histidine) for a residue having an acidic side chain (e.g., aspartic acid or glutamic acid); and (d) a residue having a bulky side chain (e.g., phenylalanine) for glycine or other residue having a small side chain.

In some embodiments, a polypeptide described herein comprises a substitution (e.g., a substitution with any of the other naturally-occurring amino acids) at one or more of the following amino acid positions relative to SEQ ID NO:1: the asparagine at position 71, the histidine at position 72, the glutamate at position 73, the glutamate at position 76, the valine at position 121, the tyrosine at position 122, the arginine at position 124, the aspartate at position 147, the threonine at position 149, the arginine at position 173, the methionine at position 177, the glycine at position 178, and the glycine at position 179. In some embodiments, the substitution is a conservative amino acid substitution. In some embodiments, the substitution is a non-conservative amino acid substitution.

In some embodiments, the tyrosine at position 122 of SEQ ID NO:1 is substituted with an amino acid selected from the group consisting of: aspartic acid and glutamic acid. In some embodiments, the arginine at position 124 of SEQ ID NO:1 is substituted with a lysine. In some embodiments, the aspartate at position 147 of SEQ ID NO:1 is substituted with a glutamic acid.

In some embodiments, the tyrosine at position 122 (relative to SEQ ID NO:1) of SEQ ID NO: 2 is substituted with an amino acid selected from the group consisting of: aspartic acid and glutamic acid. In some embodiments, the arginine at position 124 (relative to SEQ ID NO:1) of SEQ ID NO:2 is substituted with a lysine. In some embodiments, the aspartate at position 147 (relative to SEQ ID NO:1) of SEQ ID NO:2 is substituted with a glutamic acid.

In some embodiments, a polypeptide as described herein comprises an amino acid sequence of SEQ ID NO:3. In some embodiments, a polypeptide as described herein comprises an amino acid sequence of SEQ ID NO:4. In some embodiments, a polypeptide as described herein comprises an amino acid sequence of SEQ ID NO:5. In some embodiments, a polypeptide as described herein comprises an amino acid sequence of SEQ ID NO:6.

In some embodiments, administration of a polypeptide described herein, or a pharmaceutical composition thereof, increases GluD1 expression. In some embodiments, a Clbn1 variant polypeptide as described herein increases GluD1 expression by about 1% to about 100% compared to a polypeptide of SEQ ID NO:1 or SEQ ID NO:2. For example, in some embodiments, a Clbn1 variant polypeptide as described herein can increase GluD1 expression by about 1% to about 25%, about 1% to about 50%, about 1% to about 75%, about 75% to about 100%, about 50% to about 100%, or about 25% to about 100% compared to a polypeptide of SEQ ID NO:1 or SEQ ID NO:2.

TABLE 3

Exemplary amino acid sequences for Cbln1 variants

| Description | SEQ ID NO. | Sequence |
|---|---|---|
| Cbln1Y122D | 3 | MLGVLELLLLGAAWLAGPARGQNETEPIV-LEGKCLVVCDSNPTSDPT GTALGISVRSGSAKVAFSAIRSTNHEPSEMSNRT-MIIYFDQVLVNIG NNFDSERSTFIAPRKGIYSFNFHVVKVDNRQ-TIQVSLMLNGWPVISA FAGDQDVTREAASNGVLIQMEKGDRAYLK-LERGNLMGGWKYSTFSGF LVFPL |
| Cbln1Y122E | 4 | MLGVLELLLLGAAWLAGPARGQNETEPIV-LEGKCLVVCDSNPTSDPT GTALGISVRSGSAKVAFSAIRSTNHEPSEMSNRT-MIIYFDQVLVNIG NNFDSERSTFIAPRKGIYSFNFHVVKVENRQ-TIQVSLMLNGWPVISA FAGDQDVTREAASNGVLIQMEKGDRAYLK-LERGNLMGGWKYSTFSGF LVFPL |
| Cbln1R124K | 5 | MLGVLELLLLGAAWLAGPARGQNETEPIV-LEGKCLVVCDSNPTSDPT GTALGISVRSGSAKVAFSAIRSTNHEPSEMSNRT-MIIYFDQVLVNIG NNFDSERSTFIAPRKGIYSFNFHVVKVENKQ-TIQVSLMLNGWPVISA FAGDQDVTREAASNGVLIQMEKGDRAYLK-LERGNLMGGWKYSTFSGF LVFPL |
| Cbln1D147E | 6 | MLGVLELLLLGAAWLAGPARGQNETEPIV-LEGKCLVVCDSNPTSDPT GTALGISVRSGSAKVAFSAIRSTNHEPSEMSNRT-MIIYFDQVLVNIG NNFDSERSTFIAPRKGIYSFNFHVVKVENRQ-TIQVSLMLNGWPVISA FAGDQEVTREAASNGVLIQMEKGDRAYLK-LERGNLMGGWKYSTFSGF LVFPL |

In some embodiments, a Clbn1 variant polypeptide as described herein increases GluD1-Clbn1 signaling compared to a polypeptide of SEQ ID NO:1 or SEQ ID NO:2. In some embodiments, a Clbn1 variant polypeptide as described herein increases GluD1-Clbn1 signaling by about 1% to about 200% compared to a polypeptide of SEQ ID NO:1 or SEQ ID NO:2. For example, in some embodiments, a Clbn1 variant polypeptide as described herein can increase GluD1-Clbn1 signaling by about 1% to about 25%, about 1% to about 50%, about 1% to about 75%, about 1% to about 100%, about 1% to about 125%, about 1% to about 150%, about 1% to about 175%, about 175% to about 200%, about 150% to about 200%, about 125% to about 200%, about 100% to about 200%, about 75% to about 200%, about 50% to about 200%, or about 25% to about 200% compared to a polypeptide of SEQ ID NO:1 or SEQ ID NO:2.

In some embodiments, administration of a polypeptide described herein, or a pharmaceutical composition thereof, reduces GluA1 expression. In some embodiments, a Clbn1 variant polypeptide as described herein reduces GluA1 expression by about 1% to about 200% compared to a polypeptide of SEQ ID NO:1 or SEQ ID NO:2. For example, in some embodiments, a Clbn1 variant polypeptide as described herein can reduce GluA1 expression by about 1% to about 25%, about 1% to about 50%, about 1% to about 75%, about 1% to about 100%, about 1% to about 125%, about 1% to about 150%, about 1% to about 175%, about 175% to about 200%, about 150% to about 200%, about 125% to about 200%, about 100% to about 200%, about 75% to about 200%, about 50% to about 200%, or about 25% to about 200% compared to a polypeptide of SEQ ID NO:1 or SEQ ID NO:2.

Also provided herein are methods of treating pain in a subject in need thereof, the methods including administering to the subject a therapeutically effective amount of a polypeptide that increases GluD1-Cbln1 signaling.

In some embodiments, a polypeptide that increases GluD1-Cbln1 signaling is from about 20 to about 300 amino acids in length. For example, a polypeptide that increases GluD1-Cbln1 signaling can be from about 20 to about 50, about 20 to about 100, about 20 to about 150, about 20 to about 200, about 20 to about 250, about 250 to about 300, about 200 to about 300, about 150 to about 300, about 100 to about 300, about 50 to about amino acids in length. In some embodiments, the polypeptide is from about 150 to about 200, about 160 to about 190, or about 170 to about 180 amino acids in length. In some embodiments, the polypeptide is a recombinant cerebellin 1 or a variant thereof, e.g., any of the variants described herein. In some embodiments, the recombinant cerebellin 1 or a variant thereof has at least 80% sequence identity to SEQ ID NO:1 and/or SEQ ID NO:2.

In some of any of the embodiments described herein, the polypeptide described herein is a recombinant polypeptide. For example, the polypeptides described herein can be recombinantly expressed in different commercially available and routinely used expression vectors.

In some of any of the embodiments described herein, the pain comprises neuropathic pain, inflammatory pain, or a combination thereof. Neuropathic pain can be associated with one or more of: nerve compression, nerve damage, and abnormal processing of pain signals. Non-limiting examples of syndromes associated with abnormal processing of pain signals include: phantom limb pain, postherpetic neuralgia, and complex regional pain syndrome.

Neuropathic pain can also be associated with surgery, trauma, a viral infection, cancer, a vascular malformation, alcoholism, a central nervous system disorder, a metabolic disorder, or a combination thereof. Non-limiting examples of trauma associated with neuropathic pain include brain trauma and spinal cord trauma. Non-limiting examples of central nervous system disorders that can be associated with neuropathic include multiple sclerosis, Parkinson's disease, Alzheimer's disease, stroke, and epilepsy. In some embodiments, the metabolic disorder is diabetes. In some embodiments, the neuropathic pain comprises central pain syndrome.

In some embodiments, neuropathic pain is associated with a systemic disease. Non-limiting examples of systemic diseases associated with neuropathic pain include: diabetic neuropathy, Herpes zoster (shingles)-related neuropathy, fibromyalgia, multiple sclerosis, stroke, spinal cord injury, chronic post-surgical pain, phantom limb pain, Parkinson's disease, uremia-associated neuropathy, amyloidosis neuropathy, HIV sensory neuropathies, hereditary motor and sensory neuropathies (HMSN), hereditary sensory neuropathies (HSNs), hereditary sensory and autonomic neuropathies, hereditary neuropathies with ulcero-mutilation, nitrofurantoin neuropathy, tomaculous neuropathy, neuropathy caused by nutritional deficiency, neuropathy caused by kidney failure, and complex regional pain syndrome.

In some embodiments, the neuropathic pain is associated with exposure to a chemical compound. For example, neuropathic pain can be associated with exposure to chemical compounds such as alcohol, lead, arsenic, mercury and organophosphate pesticides.

Non-limiting examples of viral infections associated with neuropathic pain include Guillain-Barré syndrome, HIV, and Herpes zoster.

In some embodiments, the neuropathic pain is associated with the use of a therapeutic agent. For example, in some embodiments, the neuropathic pain is a side effect of a therapeutic agent. Non-limiting examples of therapeutic agents associated with neuropathic pain include: antiretroviral drugs (e.g., zalcitabine and didanosine), antibiotics (metronidazole and isoniazid), gold compounds (e.g., those used for rheumatoid arthritis), and chemotherapies. In some embodiments, the therapeutic agent is a chemotherapy.

In some embodiments, provided herein are methods for treating pain associated with chemotherapy-induced peripheral neuropathy (CIPN). CIPN is a serious complication associated with chemotherapies that can lead to a lower quality of life and dysfunction of the sensory, motor, and autonomic system. Non-limiting examples of chemotherapies include taxanes, platinum-based agents, vinca alkaloids, epothilones, eribulin, thalidomide, and bortezomib. See also, e.g., Staff et al. *Ann Neurol.* 2017; 81(6): 772-781.

Non-limiting examples of a taxane include paclitaxel, docetaxel, cabazitaxel, nab-paclitaxel, larotaxel, ortataxel, BMS-184476, tesetaxel, milataxel, taxoprexin, and opaxio. See, for example, Ojima et al. Expert Opin Ther Pat. 2016; 26(1): 1-20. Non-limiting examples of a platinum-based agent include carboplatin, cisplatin, oxaliplatin, nedaplatin, lobaplatin, heptaplatin, satraplatin, picoplatin, liposomal cisplatin, and AP 5346. Non-limiting examples of a vinca alkaloid include vinblastine, vincristine, vindesine, and vinorelbine. Non-limiting examples of an epothilone include ixabepilone, epothilone A, epothilone B, epothilone C, epothilone D, epothilone E, and epothilone F.

In some embodiments, the pain comprises inflammatory pain. In some embodiments, the inflammatory pain is associated with surgery, trauma, arthritis, or a combination thereof. See also, e.g., Varrassi et al. *Adv Ther.* 2019; 36(10): 2618-2637.

In some embodiments, the pain is idiopathic.

In some embodiments of any of the methods described herein, the method further includes administering an opioid to the subject. In some embodiments, provided herein are methods for reducing an amount of opioid administered to a subject, the method comprising administering any of the polypeptides described herein. Also provided herein are methods of reducing a duration of time during which an opioid is administered to a subject the method comprising administering any of the polypeptides described herein.

For example, in some embodiments, prior to administration with a polypeptide described herein, the subject is administered one or more opioids to treat pain (e.g., the subject is on an opioid-regime), and following or concurrent with administration of a polypeptide described herein, the dosage of the opioid administered to the subject is decreased. In some embodiments, the subject's level of pain is substantially the same as or decreased after (i) administration of a polypeptide described herein and (ii) the decrease in the dosage of the opioid compared to before (i) administration of a polypeptide described herein and (ii) the decrease in the dosage of the opioid. In some embodiments, the subject is administered a lower dose of the opioid when administered in combination with the polypeptide compared to administration of the opioid alone.

Non-limiting examples of opioids include: opium alkaloids, esters of morphine, ethers of morphine, semi-synthetic alkaloid derivatives, and synthetic opioids. Synthetic opioids can include anilidopiperidines (e.g., fentanyl, alphamethylfentanyl, alfentanilm, sufentanil, remifentanil, carfentanyl, ohmefentanyl); phenylpiperidines (e.g., pethidine, ketobemidone, MPPP, allylprodine, prodine, PEPAP, promedol); diphenylpropylamine derivatives (e.g., propoxyphene, dextropropoxyphene, dextromoramide, bezitramide, piritramide, methadone, dipipanone, levomethadyl acetate, difenoxin, diphenoxylate, loperamide); benzomorphan derivatives (e.g., dezocine, pentazocine, phenazocine); oripavine derivatives (e.g., buprenorphine, dihydroetorphine, etorphine); morphinan derivatives (e.g., butorphanol, nalbuphine, levorphanol, levomethorphan, racemethorphan); lefetamine; menthol; meptazinol; mitragynine; tilidine; tramadol; tapentadol; eluxadoline; AP-237; and 7-hydroxymitragynine.

In some embodiments, the polypeptide or a pharmaceutical composition thereof and the opioid are administered as separate dosages sequentially in any order. In some embodiments, the polypeptide or a pharmaceutical composition thereof and the opioid are administered simultaneously as separate dosages.

In some of any of the embodiments described herein, the subject's pain (e.g., the level of the subject's pain) is measured. A decrease in the level of pain can be indicative of treatment of the pain (e.g., the neuropathic and/or inflammatory pain). Non-limiting examples of scales that can be used to measure pain include unidimensional scales (e.g., such as numerical rating scales (NRS), visual analog scales, and verbal rating scales) and multi-dimensional scales (e.g., the short-form McGill Pain Questionnaire, the Brief Pain Inventory short form, the West-Haven Multidimensional Pain Inventory, and the Treatment Outcome of Pain Survey). See, e.g., Younger et al. *Curr Pain Headache Rep.* 2009; 13(1): 39-43. In some embodiments, a NRS consists of scores from 0 to 10 (or 0-100) with higher numbers indicative of more pain. In some embodiments, the visual analog scale is the Visual Analog Scale (VAS) Pain Score as described in Delgado et al. *J. Am. Acad. Orthop. Surg. Glob. Res. Rev.* 2018; 2(3): e088).

In some embodiments, the pain of the subject is decreased after administration of a polypeptide described herein as compared to before administration of the polypeptide, e.g., as measured using any of the pain scales described herein. For example, in some embodiments, the VAS Pain Score of the subject is decreased after administration of a polypeptide described herein as compared to before administration of the polypeptide.

In some embodiments, treatment of pain can be measured by the Patient Global Impression of Change (PGIC) scale. The PGIC scale can provide a single, general estimate of improvement. In some embodiments, the PGIC includes asking the subject to rate their status as: 1) very much improved; 2) much improved; 3) minimally improved; 4) no change; 5) minimally worse; 6) much worse; or 7) very much worse.

In some embodiments, pharmaceutical compositions including a polypeptide as described herein are provided. In some embodiments, the pharmaceutical compositions described herein comprise a therapeutically effective amount of polypeptide described herein.

In some embodiments, the pharmaceutical composition further includes a pharmaceutically acceptable excipient. In some embodiments, the polypeptides described herein be can be formulated into a composition in a free base, neutral, or salt form.

In some embodiments, a polypeptide described herein be can be formulated into a pharmaceutical composition suitable for intracranial, oral, intravenous, intranasal, intramuscular, subcutaneous, intraperitoneal, spinal or other parenteral routes of administration, for example by injection or infusion (e.g., intravenous infusion). In some embodiments, the polypeptides, or compositions thereof, as described herein are administered to the central nervous system of the subject. For example, a polypeptide described herein or a pharmaceutical composition thereof can be administered intrathecally. In some embodiments, pharmaceutical compositions suitable for parenteral, e.g., intravenous, administration are provided.

In some embodiments, a polypeptide described herein or a pharmaceutical composition thereof is administered before surgery. In some embodiments, administration of a polypeptide described herein or a pharmaceutical composition thereof, to a subject before surgery decreases or prevents pain in the subject after the surgery compared to no administration of the polypeptide described herein or pharmaceutical composition thereof to the subject before surgery.

In some embodiments, a polypeptide described herein or a pharmaceutical composition thereof is administered during surgery. In some embodiments, administration of a polypeptide described herein or a pharmaceutical composition thereof to a subject during surgery decreases or prevents pain in the subject after the surgery compared to no administration of the polypeptide described herein or pharmaceutical composition thereof to the subject during surgery.

In some embodiments, a polypeptide described herein or a pharmaceutical composition thereof is administered after surgery. In some embodiments, administration of a polypeptide described herein or a pharmaceutical composition thereof, to a subject after surgery decreases pain in the subject after the surgery compared to no administration of the polypeptide described herein or pharmaceutical composition thereof to the subject after surgery.

In some embodiments, a polypeptide described herein or a pharmaceutical composition thereof is administered once every about 2 to about 4 weeks. For example, once every about 2 to about 3 or about 3 to about 4 weeks. In some embodiments, a polypeptide described herein or a pharmaceutical composition thereof is administered once every about 10 days, about 11 days, about 12 days, about 13 days, about 14 days, about 15 days, about 16 days, about 17 days, about 18, days, about 20 days, about 21 days, about 22, days, about 23 days, about 24 days, about 25 days, about 26 days, about 27 days, about 28 days, about 29 days, or about 30 days. In some embodiments, administration of a polypeptide described herein or a pharmaceutical composition thereof to a subject once is sufficient to treat the subject's pain (e.g. neuropathic and/or inflammatory pain).

Also provided herein are kits including any of the compositions (e.g., polypeptide compositions) described herein. In some embodiments, a kit can include a solid composition (e.g., a lyophilized composition including a polypeptide described herein) and a liquid for solubilizing the lyophilized composition. In some embodiments, a kit can include a pre-loaded syringe including any of the compositions described herein.

In some embodiments, the kit includes a vial comprising any of the compositions described herein (e.g., formulated as an aqueous composition, e.g., an aqueous pharmaceutical composition).

In some embodiments, the kits can include instructions for performing any of the methods described herein.

Also provided herein are viral vectors that encode any of the polypeptides described herein. The term "viral vector" as referred to herein includes any viral genetic element that is capable of replication when associated with the proper control elements and that can transfer gene sequences between cells. In some embodiments, useful vectors include those vectors in which the nucleic acid segment to be transcribed is positioned under the transcriptional control of a promoter. A viral vector can include, for example, sufficient cis-acting elements for expression; other elements for expression can be supplied by the host mammalian cell or in an in vitro expression system. Viral vectors include all those known in the art, such as, without limitation, adeno-associated viral (AAV) vectors, retroviral vectors, Herpes simplex vectors, alphavirus vectors, flavivirus vectors, rhabdovirus-based vectors, and chimeric viral vectors.

In some embodiments, the viral vector is an AAV vector (see, e.g., Asokan et al., Mol. Ther. 20: 699-7080, 2012). "Recombinant AAV vectors" or "rAAVs" are typically composed of, at a minimum, a transgene or a portion thereof and a regulatory sequence, and optionally 5' and 3' AAV inverted terminal repeats (ITRs). Such a recombinant AAV vector can be packaged into a capsid and delivered to a selected target cell (e.g., a neuronal cell). The AAV sequences of the vector typically comprise the cis-acting 5' and 3' inverted terminal repeat sequences (See, e.g., B. J. Carter, in "Handbook of Parvoviruses," ed., P. Tijsser, CRC Press, pp. 155 168 (1990)). The ITR sequences are about 145 to about 210 nucleotides in length. In some embodiments, substantially the entire sequences encoding the ITRs are used in the molecule, although some degree of minor modification of these sequences is permissible. The ability to modify these ITR sequences is within the skill of the art. (See, e.g., texts such as Sambrook et al. "Molecular Cloning. A Laboratory Manual," 2d ed., Cold Spring Harbor Laboratory, New York (1989); and K. Fisher et al., *J Virol.*, 70:520 532 (1996)). An example of such a molecule employed in the present invention is a "cis-acting" plasmid containing the transgene, in which the selected transgene sequence and associated regulatory elements are flanked by the 5' and 3' AAV ITR sequences. The AAV ITR sequences may be obtained from any known AAV, including presently identified mammalian AAV types. Non-limiting examples of an AAV vector include an AAV serotype 1 vector (AAV1), an AAV serotype 2 vector (AAV2), an AAV serotype 1 and 2 hybrid vector (AAV1/2), an AAV serotype 3 vector (AAV3), an AAV serotype 4 vector (AAV4), an AAV serotype 5 vector (AAV5), an AAV serotype 6 vector (AAV6), an AAV serotype 7 vector (AAV7), an AAV serotype 8 vector (AAV8), or an AAV serotype 9 vector (AAV9). In some embodiments, the AAV vector is an AAV1 vector, an AAV2 vector, an AAV1/2 vector, an AAV4 vector, an AAV5 vector, an AAV8 vector, or an AAV9 vector. In some embodiments, the AAV vector is an AAV1/2 vector.

In some embodiments, a viral vector (e.g., AAV vector) as described herein also includes one or more regulatory sequences that are operably linked to the transgene (e.g., a nucleic acid encoding a polypeptide described herein) in a manner which permits its transcription, translation, and/or expression in a cell transfected with the viral vector or infected with a virus containing the viral vector. The term "regulatory sequence" refers to a nucleic acid sequence that regulates expression of a gene product operably linked to the regulatory sequence. The precise nature of the regulatory sequences needed for gene expression in host cells may vary between species, tissues or cell types, but shall in general include, as necessary, 5' non-transcribed and 5' non-translated sequences involved with the initiation of transcription and translation respectively, such as a TATA box, capping sequence, CAAT sequence, enhancer elements, and the like. Such 5' non-transcribed regulatory sequences can include a promoter region that includes a promoter sequence for transcriptional control of the operably joined gene. The viral vectors described herein can also include regulatory sequences such as enhancer sequences, hybrid enhancer/promoter sequences, and upstream activator sequences as desired. See, e.g., Powell et al. *Discov Med.* 2015; 19(102): 49-57 and Hagedorn et al. *Hum Gene Ther.* 2017; 28(12): 1169-1179. The viral vectors described herein can optionally include 5' leader or signal sequences. The choice and design of an appropriate vector is within the ability and discretion of one of ordinary skill in the art.

As used herein, a nucleic acid sequence (e.g., coding sequence) and a regulatory sequence are said to be "operably" linked when they are covalently linked in such a way as to place the expression or transcription of the nucleic acid sequence under the influence or control of the regulatory sequences. If it is desired that the nucleic acid sequence be translated into a functional protein or peptide, two DNA sequences are said to be operably linked if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably linked to a nucleic acid sequence if the promoter region were capable of effecting transcription of that DNA sequence such that the resulting transcript might be translated into the desired protein or polypeptide. Similarly two or more coding regions are operably linked when they are linked in such a way that their transcription from a common promoter results in the expression of two or more proteins having been translated in frame.

The term "promoter" refers to a nucleic acid sequence that is operably linked to a nucleic acid sequence encoding a polypeptide (e.g., a Cbln1 polypeptide or variant thereof) that can increase the transcription of the nucleic acid sequence encoding the polypeptide. The phrases "operatively positioned," "under control" or "under transcriptional control" means that the promoter is in the correct location and orientation in relation to the nucleic acid to control RNA polymerase initiation and expression of the gene.

In some embodiments, a promoter is constitutive. Non-limiting examples of constitutive promoters include the retroviral Rous sarcoma virus (RSV) LTR promoter (optionally with the RSV enhancer), the cytomegalovirus (CMV) promoter (optionally with the CMV enhancer) (see, e.g., Boshart et al. *Cell.* 1985; 41:521-530), the SV40 promoter, the dihydrofolate reductase promoter, the β-actin promoter, the phosphoglycerol kinase (PGK) promoter, and the EF1α, promoter (Invitrogen).

In some embodiments, a promoter is inducible. Inducible promoters allow regulation of gene expression and can be regulated by a variety of conditions including, but not limited to, exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Non-limiting examples of inducible promoters regulated by exogenously supplied compounds include the zinc-inducible sheep metallothionine (MT) promoter, the dexamethasone (Dex)-inducible mouse mammary tumor virus (MMTV) promoter, the T7 polymerase promoter system (International Publication No. WO 1998/10088); the ecdysone insect promoter (No et al. *Proc. Natl. Acad. Sci. USA*, 1996; 93:3346-3351), the tetracycline-repressible system (Gossen et al. *Proc. Natl. Acad. Sci. USA*, 1995; 89:5547-5551), the tetracycline-inducible system (Gossen et al. *Science*, 1995; 268: 1766-1769), see also Harvey et al. *Curr. Opin. Chem. Biol.*, 1998; 2:512-518), the RU486-inducible system (Wang et al. *Nat. Biotech.*, 1997; 15:239-243 and Wang et al. *Gene Then*, 1997; 4:432-441) and the rapamycin-inducible system (Magari et al. *J. Clin. Invest.* 1997; 100:2865-2872). Certain types of inducible promoters which can be useful in this context are those that are regulated by a specific physiological state, e.g., temperature, acute phase, a particular differentiation state of the cell, or in replicating cells only.

In some embodiments, a regulatory sequence imparts tissue-specific gene expression capabilities. Such tissue-specific regulatory sequences (e.g., promoters, enhancers, etc.) are well known in the art. In some embodiments, the tissue-specific regulatory sequence is a tissue-specific promoter. The term "tissue-specific" promoter refers to a nucleotide sequence which, when operably linked to a polynucleotide that encodes a gene product, causes the gene product to be produced in a cell substantially only if the cell is a cell of the tissue type corresponding to the promoter. In some embodiments, a tissue-specific promoter binds a tissue-specific transcription factor that induces transcription in a tissue-specific manner. Non-limiting examples of tissue-specific promoters include: a liver-specific thyroxin binding globulin (TBG) promoter, an insulin promoter, a glucagon promoter, a somatostatin promoter, a pancreatic polypeptide (PPY) promoter, a synapsin-1 (Syn) promoter, a creatine kinase (MCK) promoter, a mammalian desmin (DES) promoter, a α-myosin heavy chain (α-MHC) promoter, or a cardiac Troponin T (cTnT) promoter.

Further exemplary promoters that can be used in accordance with the materials and methods provided herein include amylase promoter, cathepsin, MI muscarinic receptor promoter, retroviral LTR (e.g. human T-cell leukemia virus HTLV) promoter, AAV ITR promoter, interleukin-2 promoter, collagenase promoter, platelet-derived growth factor promoter, adenovirus 5 E2 promoter, stromelysin, murine MX gene promoter, glucose regulated proteins (GRP78 and GRP94) promoter, α-2-macroglobulin promoter, vimentin promoter, MEW class I gene H-2κ b promoter, HSP70 promoter, proliferin, tumor necrosis factor promoter, thyroid stimulating hormone a gene promoter, immunoglobulin light chain promoter, T-cell receptor promoter, HLA DQa and DQβ promoters, interleukin-2 receptor promoter, MHC class II promoter, WIC class II HLA-DRa promoter, muscle creatine kinase promoter, prealbumin (transthyretin) promoter, elastase I promoter, albumin gene promoter, c-fos promoter, c-HA-ras promoter, neural cell adhesion molecule (NCAM) promoter, H2B (TH2B) histone promoter, rat growth hormone promoter, β-glucuronidase (GUSB) promoter, GUSB minimal promoter (hGBp), methyl CpG-Binding Protein-2 (MECP2) promoter, human desmin (DES) promoter, human thyroxine binding globulin (TBG) promoter, promoter of HNRPA2B1-CBX3 (UCOE), muscle creatine kinase (MCK) promoter, synthetic muscle promoter C5-12, human alpha(1) antitrypsin (hAAT) promoters, human EFla promoter, human cytomegalovirus (CMV) promoter (U.S. Pat. No. 5,168,062), human ubiquitin C (UBC) promoter, mouse phosphoglycerate kinase 1 promoter, polyoma adenovirus promoter, simian virus 40 (SV40) promoter, β-globin promoter, β-actin promoter, γ-globin promoter, β-interferon promoter, γ-glutamyl transferase promoter, mouse mammary tumor virus (MMTV) promoter, Rous sarcoma virus promoter, rat insulin promoter, glyceraldehyde-3-phosphate dehydrogenase promoter, metallothionein II (MT II) promoter, human serum amyloid (SAA) promoter, troponin I (TN I) promoter, duchenne muscular dystrophy promoter, human immunodeficiency virus promoter, Gibbon Ape Leukemia Virus (GALV) promoters, bone osteocalcin promoter, bone sialoprotein promoter, hepatitis B virus core promoter, CD2 promoter, immunoglobulin heavy chain promoter; neurofilament light-chain gene promoter, the neuron-specific vgf gene promoter, mGluR2 promoter, NFL promoter, NFH promoter, nβ2 promoter, PPE promoter, Enk promoter, T cell receptor α-chain promoter, non-neuronal glial fibrillary acidic protein (GFAP) promoter, myelin basic protein (MBP) promoter, and neuronal promoters such as hSyn, neuron-specific enolase (NSE) promoter, excitatory amino acid transporter-2 (EAAT2) promoter, CaMKII promoter, B-chain (PDGF-beta) promoter, chicken β-actin (CBA) promoter, and cytomegalovirus (CMV) promoter. See, e.g., Doll et al. *Gene Ther.* 1996; 3(5):437-47; Sandig et al., *Gene Ther*, 3:1002-9 (1996); Arbuthnot et al., *Hum. Gene Ther.*, 7: 1503-14 (1996); Stein et al., *Mol. Biol. Rep.*, 24: 185-96 (1997); Chen et al., *J. Bone Miner. Res.*, 11:654-64 (1996); Hansal et al., *J. Immunol.*, 161:1063-8 (1998); Andersen et al., *Cell. Mol. Neurobiol.*, 13:503-15 (1993); Piccioli et al., *Proc. Natl. Acad. Sci. USA*, 88:5611-5 (1991); Piccioli et al., *Neuron*, 15:373-84 (1995); and Lodish, Molecular Cell Biology, Freeman and Company, New York 2007. Additional examples of promoters are known in the art.

The term "enhancer" refers to refers to a nucleotide sequence that can increase the level of transcription of a nucleic acid encoding a protein of interest (e.g., any of the polypeptides described herein). Enhancer sequences are typically 50-1500 basepairs in length, and generally increase the level of transcription by providing additional binding sites for transcription-associated proteins (e.g., transcription factors). In some embodiments, an enhancer sequence is found within an intronic sequence. Enhancer sequences can typically act at much larger distance from the transcription start site (e.g., as compared to a promoter) than can promoters. Non-limiting examples of enhancers include a RSV enhancer, a CMV enhancer, and a SV40 enhancer.

In some embodiments, a viral vector described herein includes a post-transcriptional regulatory sequence. Non-limiting examples of a post-transcriptional regulatory sequence include a Hepatitis B Virus post-transcriptional regulatory sequence and a Woodchuck post-transcriptional regulatory sequence.

In some embodiments, a viral vector described herein includes a polyadenylation (poly(A)) sequence. "Polyadenylation" refers herein to the covalent linkage of a polyadenyl moiety, or its modified variant, to a messenger RNA molecule.

In eukaryotic organisms, most messenger RNA (mRNA) molecules are polyadenylated at the 3' end. The 3' poly(A) tail is a long sequence of adenine nucleotides (often several hundred) added to the pre-mRNA through the action of an enzyme, polyadenylate polymerase. In higher eukaryotes, the poly(A) tail is added onto transcripts that contain a specific sequence, the polyadenylation signal. The poly(A) tail and the protein bound to it aid in protecting mRNA from degradation by exonucleases. Polyadenylation is also important for transcription termination, export of the mRNA from the nucleus, and translation. Polyadenylation can occur in the nucleus immediately after transcription of DNA into RNA, but it can also occur later in the cytoplasm. After transcription has been terminated, the mRNA chain is cleaved through the action of an endonuclease complex associated with RNA polymerase. The cleavage site is usually characterized by the presence of the base sequence AAUAAA near the cleavage site. After the mRNA has been cleaved, adenosine residues are added to the free 3' end at the cleavage site.

As used herein, a "polyadenylation signal sequence" or "poly(A) signal sequence" is a sequence that triggers the endonuclease cleavage of an mRNA and the addition of a series of adenosines to the 3' end of the cleaved mRNA. For AAV vectors that include transgene nucleic acids encoding proteins, a polyadenylation sequence generally is inserted following the transgene sequences and before the 3' AAV ITR sequence. In some embodiments, the poly(A) signal sequence is positioned 3' to the nucleic acid sequence encoding the C-terminus of a polypeptide described herein (e.g., the C-terminus of a Cbln1 polypeptide or variant thereof).

There are several poly(A) signal sequences that can be used in the vectors described herein including those derived from bovine growth hormone (bgh) (Woychik et al., Proc. Natl. Acad. Sci. U.S.A. 81(13):3944-3948, 1984; U.S. Pat. No. 5,122,458), human growth hormone (hGH), mouse-p-globin, mouse-a-globin (Orkin et al., EMBO J. 4(2):453-456, 1985), human collagen, polyoma virus (Batt et al., Mol. Cell Biol. 15(9):4783-4790, 1995), the Herpes simplex virus thymidine kinase gene (HSV TK), IgG heavy-chain gene polyadenylation signal (U.S. Publication No. 2006/0040354), human growth hormone (hGH) (Szymanski et al., Mol. Therapy. 15(7): 1340-1347, 2007), and SV40 poly(A) signal sequence, such as the SV40 late and early poly(A) signal sequence (Schek et al., Mol. Cell Biol. 12(12):5386-5393, 1992). In some embodiments, the poly(A) signal sequence is the sequence AATAAA. The AATAAA sequence can be substituted with other hexanucleotide sequences with homology to AATAAA which are capable of signaling polyadenylation, including ATTAAA, AGTAAA, CATAAA, TATAAA, GATAAA, ACTAAA, AATATA, AAGAAA, AATAAT, AAAAAA, AATGAA, AATCAA, AACAAA, AATCAA, AATAAC, AATAGA, AATTAA, or AATAAG (see, e.g., WO 06/12414).

In some embodiments, the poly(A) signal sequence can be a synthetic polyadenylation site (see, e.g., the pCl-neo expression vector of Promega which is based on Levitt el al, Genes Dev. 3(7): 1019-1025, 1989). In some embodiments, the poly(A) signal sequence is the polyadenylation signal of soluble neuropilin-1 (AAATAAAATACGAAATG) (see, e.g., International Publication No. WO 2005/073384). Additional examples of poly(A) signal sequences are known in the art.

In some embodiments, the vectors described herein can further include an upstream enhancer element (USE) that is placed upstream of a poly(A) signal sequence. Non-limiting examples of such USEs include: human immunodeficiency virus 1 (HIV-1) USE, SV40 late 2×USE, ground squirrel hepatitis virus (GHV) USE, Adenovirus (L3) USE, human prothrombin (hTHGB) USE, and human C2 complement gene (hC2) USE.

An AAV construct useful in the present disclosure can also contain an intron, e.g., located between the promoter/enhancer sequence and the transgene. See, e.g., Powell et al. Discov Med. 2015; 19(102): 49-57.

In some embodiments, any of the viral vectors provided herein can include a scaffold attachment region (SAR). As used herein, a "scaffold attachment region" refers to an AT-rich DNA sequence that binds specifically to one or more components of the nuclear scaffold. See, e.g., Boulikas. J. Cell. Biochem. 52:14 (1993).

Another vector element that may be used is an internal ribosome entry site (IRES). An IRES sequence is used to produce more than one polypeptide from a single gene transcript. An IRES sequence would be used to produce a protein that contains more than one polypeptide chain. Selection of these and other common vector elements is conventional, and many such sequences are available (see, e.g., Sambrook et al. "Molecular Cloning. A Laboratory Manual," 2d ed., Cold Spring Harbor Laboratory, New York (1989), and references cited therein at, for example, pages 3.18 3.26 and 16.17 16.27 and Ausubel et al., Current Protocols in Molecular Biology, John Wiley & Sons, New York, 1989).

In some embodiments, a viral vector described herein encodes one or more polypeptides comprising at least 80% (e.g., at least 85%, 90%, 91%, 92%, 93%, 94%, 95%, 96%, 97%, or 98%) sequence identity to SEQ ID NO:1, SEQ ID NO:2, SEQ ID NO:3, SEQ ID NO:4, SEQ ID NO:5, SEQ ID NO:6, or a combination thereof. In some embodiments, a viral vector described herein has or includes one or more nucleic acid sequences as shown in Table 4.

TABLE 4

Exemplary Nucleic Acid Sequences Encoding a Cbln1 Polypeptide

| Description | SEQ ID NO. | Sequence |
|---|---|---|
| Cbln1 | 7 | ATGCTGGGCGTCCTGGAGCTGCTGCTGCTGGGGGCTGCGTGGC TGGCGGGCCCGGCCCGCGGGCAGAATGAGACGGAGCCCATCGT GCTGGAGGGCAAGTGCCTGGTGGTGTGCGACTCCAACCCCACG TCCGACCCCACGGGCACTGCCCTGGGCATCTCTGTGCGCTCTG GCAGCGCCAAGGTGGCTTTCTCTGCCATCAGGAGCACCAACCA CGAGCCGTCCGAGATGAGTAATCGCACCATGATCATCTACTTC GACCAGGTACTAGTGAACATTGGGAACAACTTTGATTCAGAAC GCAGCACTTTCATCGCCCCGCGCAAAGGGATCTACAGTTTTAA CTTCCACGTGGTAAAAGTCTACAACAGACAAACCATACAGGTG AGCCTCATGCTAAACGGGTGGCCGGTGATTTCAGCCTTCGCTG GTGACCAGGACGTGACCCGGGAGGCCGCCAGCAACGGAGTCCT AATCCAAATGGAGAAAGGCGACCGAGCATACCTCAAGCTGGAG CGGGGAAACTTGATGGGGGGCTGGAAGTACTCGACCTTCTCCG GATTCCTGGTGTTTCCTCTCTGA |

TABLE 4 -continued

Exemplary Nucleic Acid Sequences Encoding a Cbln1 Polypeptide

| Description | SEQ ID NO. | Sequence |
|---|---|---|
| Mature Cbln1 | 8 | CAGAATGAGACGGAGCCCATCGTGCTGGAGGGCAAGTGCCTGG<br>TGGTGTGCGACTCCAACCCCACGTCCGACCCCACGGGCACTGC<br>CCTGGGCATCTCTGTGCGCTCTGGCAGCGCCAAGGTGGCTTTC<br>TCTGCCATCAGGAGCACCAACCACGAGCCGTCCGAGATGAGTA<br>ATCGCACCATGATCATCTACTTCGACCAGGTACTAGTGAACAT<br>TGGGAACAACTTTGATTCAGAACGCAGCACTTTCATCGCCCCG<br>CGCAAAGGGATCTACAGTTTTAACTTCCACGTGGTAAAAGTCT<br>ACAACAGACAAACCATACAGGTGAGCCTCATGCTAAACGGGTG<br>GCCGGTGATTTCAGCCTTCGCTGGTGACCAGGACGTGACCCGG<br>GAGGCCGCCAGCAACGGAGTCCTAATCCAAATGGAGAAAGGCG<br>ACCGAGCATACCTCAAGCTGGAGCGGGGAAACTTGATGGGGGG<br>CTGGAAGTACTCGACCTTCTCCGGATTCCTGGTGTTTCCTCTC<br>TGA |
| Cbln1Y122D | 9 | ATGCTGGGCGTCCTGGAGCTGCTGCTGCTGGGGGCTGCGTGGC<br>TGGCGGGCCCGGCCCGCGGGCAGAATGAGACGGAGCCCATCGT<br>GCTGGAGGGCAAGTGCCTGGTGGTGTGCGACTCCAACCCCACG<br>TCCGACCCCACGGGCACTGCCCTGGGCATCTCTGTGCGCTCTG<br>GCAGCGCCAAGGTGGCTTTCTCTGCCATCAGGAGCACCAACCA<br>CGAGCCGTCCGAGATGAGTAATCGCACCATGATCATCTACTTC<br>GACCAGGTACTAGTGAACATTGGGAACAACTTTGATTCAGAAC<br>GCAGCACTTTCATCGCCCCGCGCAAAGGGATCTACAGTTTTAA<br>CTTCCACGTGGTAAAAGTCGACAACAGACAAACCATACAGGTG<br>AGCCTCATGCTAAACGGGTGGCCGGTGATTTCAGCCTTCGCTG<br>GTGACCAGGACGTGACCCGGGAGGCCGCCAGCAACGGAGTCCT<br>AATCCAAATGGAGAAAGGCGACCGAGCATACCTCAAGCTGGAG<br>CGGGGAAACTTGATGGGGGGCTGGAAGTACTCGACCTTCTCCG<br>GATTCCTGGTGTTTCCTCTCTGA |
| Cbln1Y122E | 10 | ATGCTGGGCGTCCTGGAGCTGCTGCTGCTGGGGGCTGCGTGGC<br>TGGCGGGCCCGGCCCGCGGGCAGAATGAGACGGAGCCCATCGT<br>GCTGGAGGGCAAGTGCCTGGTGGTGTGCGACTCCAACCCCACG<br>TCCGACCCCACGGGCACTGCCCTGGGCATCTCTGTGCGCTCTG<br>GCAGCGCCAAGGTGGCTTTCTCTGCCATCAGGAGCACCAACCA<br>CGAGCCGTCCGAGATGAGTAATCGCACCATGATCATCTACTTC<br>GACCAGGTACTAGTGAACATTGGGAACAACTTTGATTCAGAAC<br>GCAGCACTTTCATCGCCCCGCGCAAAGGGATCTACAGTTTTAA<br>CTTCCACGTGGTAAAAGTCGAGAACAGACAAACCATACAGGTG<br>AGCCTCATGCTAAACGGGTGGCCGGTGATTTCAGCCTTCGCTG<br>GTGACCAGGACGTGACCCGGGAGGCCGCCAGCAACGGAGTCCT<br>AATCCAAATGGAGAAAGGCGACCGAGCATACCTCAAGCTGGAG<br>CGGGGAAACTTGATGGGGGGCTGGAAGTACTCGACCTTCTCCG<br>GATTCCTGGTGTTTCCTCTCTGA |
| Cbln1R124K | 11 | ATGCTGGGCGTCCTGGAGCTGCTGCTGCTGGGGGCTGCGTGGC<br>TGGCGGGCCCGGCCCGCGGGCAGAATGAGACGGAGCCCATCGT<br>GCTGGAGGGCAAGTGCCTGGTGGTGTGCGACTCCAACCCCACG<br>TCCGACCCCACGGGCACTGCCCTGGGCATCTCTGTGCGCTCTG<br>GCAGCGCCAAGGTGGCTTTCTCTGCCATCAGGAGCACCAACCA<br>CGAGCCGTCCGAGATGAGTAATCGCACCATGATCATCTACTTC<br>GACCAGGTACTAGTGAACATTGGGAACAACTTTGATTCAGAAC<br>GCAGCACTTTCATCGCCCCGCGCAAAGGGATCTACAGTTTTAA<br>CTTCCACGTGGTAAAAGTCGAGAACAAACAAACCATACAGGTG<br>AGCCTCATGCTAAACGGGTGGCCGGTGATTTCAGCCTTCGCTG<br>GTGACCAGGACGTGACCCGGGAGGCCGCCAGCAACGGAGTCCT<br>AATCCAAATGGAGAAAGGCGACCGAGCATACCTCAAGCTGGAG<br>CGGGGAAACTTGATGGGGGGCTGGAAGTACTCGACCTTCTCCG<br>GATTCCTGGTGTTTCCTCTCTGA |
| Cbln1D147E | 12 | ATGCTGGGCGTCCTGGAGCTGCTGCTGCTGGGGGCTGCGTGGC<br>TGGCGGGCCCGGCCCGCGGGCAGAATGAGACGGAGCCCATCGT<br>GCTGGAGGGCAAGTGCCTGGTGGTGTGCGACTCCAACCCCACG<br>TCCGACCCCACGGGCACTGCCCTGGGCATCTCTGTGCGCTCTG<br>GCAGCGCCAAGGTGGCTTTCTCTGCCATCAGGAGCACCAACCA<br>CGAGCCGTCCGAGATGAGTAATCGCACCATGATCATCTACTTC<br>GACCAGGTACTAGTGAACATTGGGAACAACTTTGATTCAGAAC<br>GCAGCACTTTCATCGCCCCGCGCAAAGGGATCTACAGTTTTAA<br>CTTCCACGTGGTAAAAGTCGAGAACAGACAAACCATACAGGTG<br>AGCCTCATGCTAAACGGGTGGCCGGTGATTTCAGCCTTCGCTG<br>GTGACCAGGAGGTGACCCGGGAGGCCGCCAGCAACGGAGTCCT<br>AATCCAAATGGAGAAAGGCGACCGAGCATACCTCAAGCTGGAG<br>CGGGGAAACTTGATGGGGGGCTGGAAGTACTCGACCTTCTCCG<br>GATTCCTGGTGTTTCCTCTCTGA |

Also provided herein are compositions including any of the viral vectors described herein. In some embodiments, the viral vector is capable of expressing a polypeptide that increases GluD1-Cbln1 signaling in a target cell of a human subject to whom the therapeutic composition is administered. In some embodiments, the GluD1-Cbln1 signaling is increased at a synapse. In some embodiments, the GluD1-Cbln1 signaling is increased at a parabrachio-central laterocapsular amygdala glutamatergic synapse.

In some embodiments, the viral vector is formulated in a pharmaceutical composition. In some embodiments, the pharmaceutical composition can include one or a plurality of AAV vectors, as described herein, in combination with one or more pharmaceutically acceptable carriers, diluents or excipients.

Upon formulation, solutions can be administered in a manner compatible with the dosage formulation and in such amount as is therapeutically effective. The formulations can be easily administered in a variety of dosage forms such as injectable solutions, injectable gels, drug-release capsules, and the like.

In some embodiments, a composition described herein is formulated for parenteral administration. In some embodiments, a composition described herein is formulated for intracranial administration. In some embodiments, a composition described herein is formulated for intravenous administration. See, e.g., Lykken et al. *J Neurodev Disord.* 2018; 10(1):16.

Also provided herein are kits including any of the compositions (e.g., viral vector compositions) described herein. In some embodiments, a kit can include a solid composition (e.g., a lyophilized composition including a viral vector described herein) and a liquid for solubilizing the lyophilized composition. In some embodiments, a kit can include a pre-loaded syringe including any of the compositions described herein.

In some embodiments, the kit includes a vial comprising any of the compositions described herein (e.g., formulated as an aqueous composition, e.g., an aqueous pharmaceutical composition).

In some embodiments, the kits can include instructions for performing any of the methods described herein.

EXAMPLES

Example 1. Structural Synaptic Changes in the Amygdala Caused by Impaired GluD1-Cbln1 Signaling can be Targeted to Mitigate Pain Pain related functional changes such as increase in PB-CeLC neurotransmission and CeLC neuron hyperexcitability are well documented in different pain models, including acute inflammatory pain and more persistent models such as neuropathic pain (see, e.g., Thompson et al. Pain Res Manag. 2017; 2017:8296501; Bird et al. *J Physiol.* 2005; 564(Pt 3): 907-921; Cheng et al. J Neurosci. 2011; 31(6): 2258-70; and Ikeda et al. *Pain.* 2007; 127(1-2):161-72). CeLC neurons can be classified into neurochemically distinct subsets, whose roles in pain processing are beginning to emerge. Two major non-overlapping cell populations are defined by their expression of PKCδ or SOM. Evidence suggests that PKCδ(+) neurons are the main targets of synapses from PB-CGRP terminals (see, e.g., Kruger et al. Brain Res. 1988 Nov. 1; 463(2):223-44; de Lacalle and Saper. Neuroscience. 2000; 100(1):115-30; Dobolyi et al. J Comp Neurol. 2005 Aug. 15; 489(1):92-119; Schwaber et al. J Comp Neurol. 1988 Apr. 15; 270(3):416-26, 398-9; and Han et al. Cell. 2015 Jul. 16; 162(2):363-374), while SOM (+) neurons receive inputs from primarily CGRP-negative PB cells (Wilson et al. Cell Rep. 2019 Oct. 8; 29(2):332-346.e5; Li and Sheets. Pain. 2020 January; 161(1):166-176; and Ye and Veinante. Brain Struct Funct. 2019 April; 224 (3):1067-1095). In a neuropathic pain model hyperexcitability was noted specifically in the CeLC PKCδ(+) neuron subtype that shows late firing pattern (Wilson et al. Cell Rep. 2019 Oct. 8; 29(2):332-346.e5). Late firing neurons also showed increased PB-CeLC neurotransmission in an inflammatory pain model, (Sugimura et al. J Neurophysiol. 2016 Jun. 1; 115(6):2721-39) and an increase in synaptic efficacy of presumable PKCδ(+) neurons was observed in a neuropathic pain model (Li and Sheets. Pain. 2020 January; 161(1):166-176). In contrast, no change in the neuronal excitability (Wilson et al. Cell Rep. 2019 Oct. 8; 29(2):332-346.e5), but a decrease in synaptic efficacy was found in CeLC SOM(+) neurons in neuropathic pain models (Li and Sheets. Pain. 2020 January; 161(1):166-176). Despite these advances, a significant knowledge gap remains in the understanding of the structural synaptic signaling under normal conditions and in pain conditions associated with dysfunction of PB-CeLC neurotransmission.

GluD1 and GluD2 form the delta family of ionotropic GluRs (iGluRs). Unlike other iGluRs, they do not exhibit typical agonist-induced currents (Naur et al. Proc Natl Acad Sci USA. 2007 Aug. 28; 104(35):14116-21; Yaday. Brain Res. 2011; 1382:1-8). Instead of functioning as typical iGluRs, GluDs are involved in synapse formation and maintenance through interactions with presynaptic Neurexin via Cbln1, released from presynaptic terminals (see, e.g., Uemura et al. Cell. 2010 Jun. 11; 141(6):1068-79). Together, the GluD-Cbln1-Neurexin forms a trans-synaptic complex that regulates synapse formation and maintenance (see, e.g., Uemura et al. Cell. 2010 Jun. 11; 141(6):1068-79). Recently a role of GluD1 has been established at thalamostriatal synapses as well as hippocampal synapses (Liu et al. Neurobiol Dis. 2020; 137:104746; Tao et al. Proc Natl Acad Sci USA. 2018; 115(23):E5373-E5381). Neuroanatomical studies have found strong expression of GluD1 in the CeA (Konno et al. J. Neurosci. 2014; 34:7412-7424; Hepp et al. Brain. Struct. Funct. 2014), but no Cbln1 mRNA or other Cblns (Miura et al. Eur. J. Neurosci. 2006; 24:750-760; Otsuka et al. J. Neurosci. 2016; 36:11801-11816). However, Cbln1 is heavily expressed in PB neurons, known a major source of glutamatergic inputs to CeLC (Miura et al. Eur. J. Neurosci. 2006; 24:750-760; Otsuka et al. J. Neurosci. 2016; 36:11801-11816), suggesting that the GluD1-Cbln1 complex may be involved in the formation/maintenance of PB-CeLC glutamatergic synapses. Furthermore, GluD1 KO and Cbln1 KO mice display impaired fear acquisition and altered anxiety-like behaviors (Otsuka et al. J. Neurosci. 2016; 36:11801-11816; Yadav et al. PLoS One. 2018; e60785), which are amygdala-dependent behaviors. The specific role of GluD1-Cbln1 structural signaling in regulating PB-CeLC synapses and pain-related behaviors is unknown.

Here, it was found that the synaptic organizer glutamate delta 1 receptor (GluD1) is expressed postsynaptically at parabrachio-central laterocapsular amygdala (PB-CeLC) glutamatergic synapses at axo-somatic and punctate locations on protein kinase C δ-positive (PKCδ+) neurons. In inflammatory and neuropathic pain models, GluD1 and its partner cerebellin 1 (Cbln1) are downregulated while AMPA receptor is upregulated. A single infusion of recombinant Cbln1 into the central amygdala led to sustained mitigation of behavioral pain parameters and normalized synaptic dysfunction pointing to its therapeutic potential. This Cbln1 effect was GluD1-dependent and showed lateralization to right central amygdala. In normal animals, GluD1-Cbln1 signaling was necessary for averse and fear learning. Thus, GluD1-Cbln1 signaling in the central amygdala is a teaching signal for aversive behavior but its sustained dysregulation underlies persistence of pain. See Ghandi, P.; Gawande, D. Y; Shelkar, G. P.; Gakare, S. G.; Kiritoshi, T.; Ji, G.; Misra, B.; Pavuluri, R.; Liu, J.; Neugebauer, V; and Dravid, S. M. A central amygdala trans-synaptic signaling mechanism of chronic pain. *Neuron*. 2021.

Methods

Animals

Wildtype and GluD1 knockout (KO) male and female mice were group housed in the animal house facility at a constant temperature (22±1° C.) and a 12-hour (hr) light-dark cycle with free access to food and water. Behavioral testing was performed between 9:00 a.m and 4:00 p.m. GluD1 KO mice were obtained from Dr. Jian Zuo (Gao, et al. *Mol. Cell. Biol.* 2007; 27(12):4500-12). These were on >95% C57BL/6 and remaining 129SvEv background. GluD1$^{flox/flox}$ mice on congenic C57BL/6 background were obtained from Dr. Pei Lung-Chen with loxP sites in intron 10 and 12. PKCδ Cre mice (on congenic C57BL/6 background) were obtained from Dr. David Anderson with GluClα-ires-Cre cassette inserted into PKCδ gene. These mice were crossed with GluD1$^{flox/flox}$ to selectively ablate GluD1 from PKCδ cell type. In animals without any surgical manipulation, electrophysiology and immunohistochemical studies were carried out at 4-6 weeks of age and 2-3 months of age for behavioral studies. For mice with surgical manipulation all studies were carried out at 3-4 months of age. In this study strict measures were taken to minimize pain and suffering to animals in accordance with the recommendations in the Guide for Care and Use of Laboratory Animals of the National Institutes of Health. All experimental protocols were approved by the Creighton University Institutional Animal Care and Use Committee Policies and Procedures.

Adult male Sprague-Dawley rats, 250 g to 350 g at time of testing, were housed 3 per cage on a 12-hr light-dark cycle (lights on at 7:00 am) with unrestricted access to food and water. On the day of the experiment, animals were transferred from the animal facility to the laboratory and acclimated for at least 1 hr. All procedures were approved by the Institutional Animal Care and Use Committees (IACUC) of Texas Tech University Health Sciences Center. All studies were conducted in accordance with the policies and recommendations of the National Institutes of Health Guide for the Care and Use of Laboratory Animals. Experiments were done in a blinded fashion and reproduced by several investigators.

Immunohistochemistry

Mice or rats were transcardially perfused with 4% paraformaldehyde (PFA) in 0.1 M phosphate buffer (PB) pH 7.4, and brains collected and stored overnight in the same fixative at 4° C. Brains were then transferred successively into solutions of 10%, 20% and 30% sucrose in 0.1 M PB and thereafter frozen at −30° C. to −40° C. using isopentane. For immunohistochemistry, 20-µm-thick coronal sections were cut using a cryostat (LEICA® CM 1900). After washing, sections were incubated in blocking solution containing 10% normal goat serum (Jackson ImmunoResearch Laboratories Inc. Catalog #005-000-121) or chicken serum (Jackson ImmunoResearch Laboratories Inc. Catalog #003-000-120) or normal donkey serum in 0.25% Triton-X in 0.1 M PB (PBT) for 1 hr at room temperature. Following blocking, sections were incubated overnight at 4° C. in primary antibodies at appropriate concentrations in PBT guinea pig GluD1 primary antibody (1:500, GluD1C-GP-Af860, Frontier Institute Co., Ltd, Japan), rabbit vGlut1 (1:10000, VGT1-3, Mab technologies), chicken vGlut2 (1:1000, Synaptic systems), rabbit CGRP (1:500, Millipore sigma), mouse PKCδ (1:500, BD Biosciences, #10397), rabbit SST (1:500, BMA Biomedicals/Penninsula Laboratories, #T-4103), rabbit PSD93 (1:500, Frontier Institute Co., Ltd, Japan, #AF 769), rabbit PSD95 (1:500, Invitrogen, #51-690. For primary antibodies rabbit Cbln1 (1:500, Cbln1-Rb-Af270, Frontier Institute Co., Ltd, Japan) and GluA1 (1:500, GluA1-Rb-Af690, Frontier Institute Co., Ltd, Japan), 100 µm thick coronal sections were cut and epitope retrieval was performed using pepsin and citrate treatment, respectively before blocking. For pepsin treatment, sections were incubated for 3 mins in 1 mg/mL pepsin in 0.9N HCl at 37° C. For citrate treatment, sections were incubated in sodium citrate buffer (10 mM sodium citrate acid, 0.05% Tween 20, pH 6.0) at 90° C. for 20 mins. The following day, sections were washed and thereafter incubated with the appropriate secondary antibodies goat anti-guinea pig conjugated to AlexaFluor 488 (1:500, A-11073, Life Technologies, Eugene), or goat anti-rabbit secondary antibody conjugated to AlexaFluor 594 (1:500, A-11012, Life Technologies) or goat anti-rabbit marina blue (1:500, M10992, Molecular probe), or donkey anti-rabbit conjugated to AlexaFluor 488 (1:500, A-21206, Life Technologies), or goat anti-chicken conjugated to DyLight 488 (1:500, 072-03-24-06, KPL USA), or goat anti-mouse secondary antibody conjugated to AlexaFluor 594 (1:500, A-11032, Life Technologies) for 2 hr at room temperature.

Sections were then washed and mounted with Fluoromount-G (Southern Biotech, AL, USA). Widefield images were acquired using Infinity camera (Lumenera Co., Ontario, Canada) and epifluorescence microscope (Nikon Eclipse Ci) with the Lumenera Infinity Analyze software (Lumenera Co.). For confocal images equivalent regions, 1024×1024 pixels, were captured using a Leica TCS SP8 MP confocal microscope using a 20× or 40× objective at 2× zoom. The region of interest was scanned at 0.3 µm intervals along the z-axis and an optical section (3.88 µm thick) was taken from each tissue section. Co-localization of GluD1 with vGluT1, vGluT2 and Cbln1 and the quantification of puncta number of vGluT1, vGluT2, Cbln1 and GluA1 were analyzed by Volocity (PerkinElmer Inc. Coventry, United Kingdom). The number of puncta per image was filtered based on intensity and size range (>0.1-0.3 µm$^3$). Changes in GluD1 levels in WT mice as well as in rats were measured as surface volume around the PKCδ cell type. Three or more images were analyzed from three or more sections per animal. Quantification of synaptic puncta was performed using a coding system for blinding to genotype or treatment. Image acquisition for representatives as well as 3-D reconstruction was done using surface module of Imaris software 8.4.1, a 3-D imaging software (Bitplane, South Windsor, CT, USA). The video representing the close apposition of GluD1 on PKCδ cell surface was done using animation mode of Imaris software.

Whole-Cell Electrophysiology

Mice: Whole-cell electrophysiology was performed as previously described (Liu et al. *Neurobiol Dis*. 2020; 137: 104746) with minor modifications. After isoflurane anesthesia, mice were decapitated and brains were removed rapidly and placed in ice-cold artificial cerebrospinal fluid (ACSF) of the following composition: 130 mM NaCl, 24 mM NaHCO$_3$, 3.5 mM KCl, 1.25 mM NaH$_2$PO$_4$, 0.5 mM CaCl$_2$, 3 mM $MgCl_2$ and 10 mM glucose saturated with 95% $O_2$/5% $CO_2$. 300-350 µm thick coronal sections were prepared using vibrating microtome (Leica VT1200, Buffalo Grove, IL, USA). Whole-cell patch recordings were obtained from neurons in latero capsular region of CeA (CeLC) in voltage-clamp configuration with an AXOPATCH™ 200 B (Molecular Devices, Sunnyvale, CA, USA). Glass pipette with a resistance of 4-6 MΩ were filled with an internal solution consisting of: 110 mM cesium gluconate, 30 mM CsCl, 5 mM HEPES, 4 mM NaCl, 0.5 mM $CaCl_2$, 2 mM $MgCl_2$, 5 mM BAPTA, 2 mM $Na_2$ATP, and 0.3 mM $Na_2$GTP (pH 7.35). QX314 was added to the internal solution to block voltage-gated sodium channels. The recording artificial cerebrospinal fluid (ACSF) contained (in mM) 1.5 $CaCl_2$ and 1.5 $MgCl_2$. Neurons were held at a holding potential of −70 mV for miniature excitatory postsynaptic currents (mEPSCs) and 0 mV for miniature inhibitory postsynaptic currents (mIPSCs). mEPSCs were recorded in the presence of 0.5 µM tetrodotoxin and 100 µM picrotoxin. mIPSCs were recorded in the presence of 0.5 µM tetrodotoxin, 10 µM cyanquixaline (CNQX) and 100 µM DL-APS. Whole-cell recordings with a pipette access resistance less than 20 MΩ and that changed less than 20% during the duration of recording were included. Signal was filtered at 2 kHz and digitized at 10 kHz using an AXON™ DIGIDATA® 1440A analog-to-digital board (Molecular Devices, CA). The mEPSC and mIPSC recordings were analyzed using Mini-analysis software (Synaposoft, Atlanta, GA, USA) with an amplitude threshold set at 5 pA. Frequency and amplitude of the miniature and spontaneous currents were determined. For evoked responses a bipolar stimulating electrode (World precision instruments, FL, USA) was placed on the fiber tract dorsomedial to the CeLC, which carries afferents from parabrachial (PB) (Neugebauer et al. *J. Neurosci.* 2003; 23(1): 52-63; Ikeda et al. *Pain.* 2007; 127(1-2):161-72). Evoked EPSCs were recorded from CeLC neurons at a holding potential of −70 mV in the presence of picrotoxin (100 µM). Thirty consecutive trials were recorded at 0.1 Hz for each condition. Amplitudes of AMPA receptor-EPSCs were calculated by averaging 30 EPSCs at each condition. For recording cell excitability current-clamp recordings were conducted as previously described (Liu et al. *Mol Pharmacol.* 2019; 96(2):193-203).

Rats: Coronal (400 µm) brain slices containing the CeA of the right hemisphere were obtained as described previously (Thompson et al. *Neuropharmacology.* 2018; 138: 219-231; Navratilova et al. *Pain.* 2020; 161(3):609-618). The right hemisphere was selected because of evidence for lateralized amygdala function in pain (see Allen et al. *Prog Neurobiol.* 2021; 196:101891). Brains were immerged in ice-cold oxygenated physiological solution (87 mM NaCl, 75 mM sucrose, 25 mM glucose, 5 mM KCl, 21 mM $MgCl_2$, 0.5 mM $CaCl_2$, and 1.25 mM $NaH_2PO_4$). Brain slices were prepared using a Vibratome (VT1200S, Leica Biosystems, Nussloch, Germany) and incubated in oxygenated ACSF at 35° C. for 20 min, and then at room temperature (21° C.) for at least 40 min. One slice was transferred to the recording chamber and superfused by ACSF (31±1° C.) at ~2 ml/min. Only one or two brain slices per animal were used. Only one or two neurons were recorded in each slice. Whole-cell voltage- and current-clamp recordings were made from visually identified CeLC neurons using DIC-IR videomicroscopy as described previously (Thompson et al. *Neuropharmacology.* 2018; 138: 219-231; Navratilova et al. *Pain.* 2020; 161(3):609-618). Borosilicate glass electrodes had tip resistances of 6-8 MΩ and were filled with a potassium gluconate based internal solution containing: 122 mM K-gluconate, 5 mM NaCl, 0.3 mM $CaCl_2$), 2 mM $MgCl_2$, 1 mM EGTA, 10 mM HEPES, 5 mM Na2-ATP, and 0.4 mM Na3-GTP; pH was adjusted to 7.2-7.3 with KOH and osmolarity to 280 mOsm/kg with sucrose. For data acquisition and analysis, a low-noise Digidata 1322A interface (Axon Instruments, Molecular Devices, San Jose, CA), a dual 4-pole Bessel filter (Warner Instruments, Hamden, CT), Axoclamp-2B amplifier (Axon Instruments), and pClamp10 software (Axon Instruments) were used. If series resistance (monitored with pClamp10 software) changed >20%, the neuron was discarded. In current clamp mode, action potentials were evoked from a holding potential of −60 mV using 0.5 s depolarizing current steps of increasing amplitude. Rheobase was defined as the minimal depolarizing current (0.5 s, 10 pA steps) that induces an action potential.

Synaptoneurosome Preparation and Western Blot Analysis

For synaptoneurosomal preparation, mice were anesthetized using isoflurane anesthesia, mice were then decapitated and thereafter all experimental procedures were conducted on ice. The right central amygdala were punched out separately and put into ice cold synaptoneurosomal buffer (10 mM HEPES, 1 mM EDTA, 2 mM EGTA, 0.5 mM DTT, 10 µg/ml leupeptin, and 50 µg/ml soybean trypsin inhibitor, pH 7.0) additionally containing 5 mg/ml pepstatin, 50 mg/ml aprotonin and 0.5 mM phenylmethanesulfonylfluoride (PMSF). The tissue was thoroughly homogenized. The homogenate was diluted further with the same volume of synaptoneurosome buffer and briefly and gently sonicated delivering 3 pulses using an output power of 1 Sonic dismembrator Model 100 (Fischer Scientific, NJ, USA). The sample was loaded into a 1.0 ml Luer-lock syringe (BD syringes) and filtered twice through three layers of a pre-wetted 100 µm pore nylon filter CMN-0105-D (Small Parts Inc., Logansport, IN, USA) held in a 13 mm diameter filter holder XX3001200 (Milipore, MA, USA). The resulting filtrate was loaded into a 1 ml Luer-lock syringe and filtered through a pre-wetted 5 µm pore hydrophilic filter CMN-0005-D (Small Parts Inc., Logansport, IN, USA) held in a 13 mm diameter filter holder. The resulting filtrate was centrifuged at 1000×g for 10 min. The pellet obtained corresponded to the synaptoneurosome fraction. Isolated synaptoneurosomes were resuspended in 75 µl of buffer solution containing 0.32 M sucrose, and 1 mM $NaHCO_3$ (pH 7.0).

For western blotting, synaptoneurosomes were loaded on 10% Sodium dodecyl sulfate gel in equal amount (15-30 µg/well). The samples were run at 114 volts for a duration of 1 hr. Gels were transferred to nitrocellulose membrane (GE Healthcare, Piscataway, NJ, USA), a wet transfer was carried out. The voltage for transfer was kept at 114 volts, and the duration for which transfer was carried out was 1 hr 15 min. Electrophoresis and transfer apparatuses used were the Biorad mini protean tetra cell (Bio-Rad Laboratories, Inc., Hercules, California, USA). Transfer was followed by blocking with 5% milk in Tris-buffered Saline with 1% Tween 20 (TBST) for 1 hr at room temperature. The primary antibodies; rabbit anti-GluD1 (AGC-038, Alomone labs), 1:1000; guinea pig anti-pan-AMPAR (Af580, Frontier Institute Co., Ltd) were used and kept overnight for incubation at 4° C. After primary antibody incubation, the blots were washed and incubated with horse-radish peroxidase (HRP) conjugated anti-rabbit secondary antibody, 1:5000 (Cell Signaling Technology, Danvers, MA, USA) or HRP conjugated anti-guinea pig (#AP108P, Sigma-Aldrich), 1:10000, for 1 hr at room temperature followed by washing with TBST. Blots were developed using enhanced chemiluminescent (ECL) Plus Western Blotting Detection System kit RPN2132 (GE Healthcare, Piscataway, NJ, USA). Blots were analyzed using X-ray film processor or FluorChem Q (Proteinsimple) or Chemidoc (Biorad). For analysis of protein expression the arbitrary optical density of each sample was normalized to β-actin.

Stereotaxic Surgery

Stereotaxic AAV Administration

Administration of AAV was conducted as previously described (Liu et al. *Mol Pharmacol.* 2019; 96(2):193-203). Briefly, mice were anesthetized with isoflurane and placed in a stereotaxic frame (51733U, Stoelting, Wood Dale, IL, USA). The skull was exposed, and small hole was drilled through the skull at the coordinates for central amygdala (AP:−1.22 mm, ML: ±2.9 mm, DV: −4.6 mm). The virus particles AAV-hSyn-DIO-hM3D(Gq) or AAV-hSyn-DIO-hM4D(Gi)-mCherry (Neurophotonics, Canada) or AAV9.hsyn. eGFP/AAV9.hsyn. eGFP-Cre (University of Pennsylvania vector core) were injected by using microliter syringe (NanoFil, World Precision Instruments, Sarasota, FL, USA) with 33-gauge beveled needle (NF33BV-2, World Precision Instruments). The injection needle was lowered, and virus particles were delivered at a rate of 1 nl/sec using a UMP3 micro-syringe pump (World Precision Instruments). The volume of injections was kept at 150 nl to obtain the precise local infection and to avoid the leak into other brain regions. The needle was left in place for additional 10 min at the injection site and was slowly withdrawn over the period of 5 min. The incision was sealed with surgical tissue adhesive (1469SB, 3M, Maplewood, MN, USA). Only mice that had virus injection restricted to the CeA were included in the study.

Cannulation

Cannulation surgery was performed similar to as previously described (Liu et al. *Mol Pharmacol.* 2019; 96(2): 193-203). Mice were anesthetized with isoflurane and placed in a stereotaxic frame. The skull was exposed, a small hole was drilled through the skull, and the 26-gauge stainless steel guide cannula was implanted unilaterally above the lateral ventricle for ICV administration at the stereotaxic coordinates (AP: −0.22 mm, ML: +0.8 mm, DV: −2.3 mm). For bilateral CeA cannulation, guide cannula was implanted at the stereotaxic coordinates (AP: −1.22 mm, ML: ±2.75 mm, DV: −4.0 mm). The guide cannulae were secured to the skull with stainless steel screws and dental acrylic cement. The animals were allowed 10 days of recovery period before being used for any experiments. Cannula and viral injection locations were verified after the end of behavioral experiments by examining the fixed brain tissue from these animals under light or fluorescent microscope.

Pain Induction Models

CFA Inflammatory Pain Model

Inflammation was induced by intraplantar injection of 10 µl of complete Freund's adjuvant (CFA; 0.5 mg/ml heat-killed *M. tuberculosis*; Sigma, St. Louis, MO) intraplantarly in the hind paw. Saline (pH 7.4) served as control. CFA usually takes 4-5 hours to elicit its effect. Hence, behavioral assessment was conducted 6 hours onwards after induction of CFA injection. Mechanical sensitivity was measured using electronic Von Frey filament.

Spinal Nerve Ligation Pain Model

The spinal nerve ligation (SNL) model of chronic neuropathic pain was induced as previously described (Watabe et al. *Mol. Brain.* 2013; 6:11; Kim et al. *Pain.* 1992; 50(3): 355-363). Surgical procedure was conducted under isoflurane anesthesia. L5 spinal nerve was isolated and tightly ligated with 6-0 silk thread. The muscles were sutured, closed and the skin was clipped together. Antibiotic bacitracin was applied, and animals were monitored post-surgery for any signs of distress. In sham operated control animals, same surgical procedure was performed without spinal nerve ligation or irritation.

Drug Administration

Recombinant cerebellin 1 (Cbln1) administration. Recombinant Cbln1 (6934-CB-025, R&D systems or 00361-03-100, Aviscera Bioscience) was administered in the CeA (through cannula) at a dose of 250 ng in 500 nl per side in sterile PBS. For intracerebroventricular injection a dose of 1.5 µg in 1.5 µl was used. Changes in mechanical hypersensitivity was observed up to a week after Cbln1 administration. In rats with neuropathic pain, Cbln1 (500 ng in 1 µl) was administered unilaterally in right CeA (coordinates: 2.5 mm caudal to bregma, 4.0 mm lateral to midline, and 7.5 mm deep) using a 5 µl Hamilton syringe (33 gauge) while the animals were anesthetized with isoflurane (5%, induction; 2%, maintenance; precision vaporizer, Harvard Apparatus, Holliston, MA) and placed in a stereotaxic frame (David Kopf Instruments, Tujunga, CA) and changes in vocalization, averse and affective behaviors was recorded up to a week after drug administration. The right CeA was selected because previous reports have shown right hemisphere lateralization of amygdala function in the modulation of tactile hypersensitivity in rodents (see Allen et al. *Prog. Neurobiol.* 2021; 196:101891). To determine if the restoration is mediated through GluD1-Cbln1 complex, recombinant Cbln2 (7044-CB-050, R&D systems) at the same dose was used as control.

Chemogenetics. Clozapine-N-oxide (CNO; Hello Bio Inc., Princeton, NJ) was dissolved in saline and injected i.p. at 1 mg/kg body weight as we have previously described (Liu et al. *Mol Pharmacol.* 2019; 96(2):193-203). Mechanical hypersensitivity was tested at 48 hrs after intraplantar CFA/saline injection. CNO/saline was then intraperitoneally injected and mechanical hypersensitivity was measured 1 hr and 24 hrs after CNO/saline injection.

Behavioral Assessment Tests in Mouse

Von Frey filament test: Von Frey filament test in mice was performed using electronic Von Frey (IITC systems). Animals were habituated and testing chambers with a penetrable mesh beneath. A rigid filament (from IITC systems) was applied perpendicularly to the plantar surface of the hind paw, and a constant pre-determined force was delivered for 2-5 s. Animals were habituated to the filament application and baseline reading were taken. Paw withdrawal threshold was measured as the force at which the animal exhibits any of the nocifensive responses like brisk paw withdrawal, licking, or shaking of the paw, either during or immediately after application of the stimulus. Average of 3 readings were taken.

Tail flick test: In tail flick test heat stimulus was applied to the tail of mice and rats, and the latency at which the tail "flicks" or twitches was recorded.

Hotplate test: Mouse was placed in the chamber, on a metal surface maintained at a constant temperature between 50° C. and 55° C. The response latency for paw licking or jumping behavior was recorded. The animal was removed from the hot plate if no nocifensive responses are observed, after pre-determined cut-off latency of 20 s to prevent tissue burn.

Gabapentin induced conditioned place preference: Conditional place preference (CPP) apparatus consisting of two equally sized chambers (20 cm×20 cm×20 cm) with distinct contextual characteristics was used for CPP study. On day 1, mice were habituated for 30 minutes with free access to both the chambers. On day 2, the baseline preference for each chamber was recorded for 15 minutes (pretest). After pretest readings were determined, gabapentin was paired with the non-preferred chamber, and saline was paired with the preferred chamber. On the conditioning day, day 3, mice received an intraperitoneal injection of saline and after 10 mins were restricted in preferred chamber for 30 minutes in morning. At least 4 hours after the saline was injected, the same mice were injected with gabapentin (100 mg/kg) and after 10 minutes were placed in nonpreferred chamber. On day 5, for post-test, mice were placed in the CPP box with the door open to have free access to both the chambers for 15 minutes and the number of entries and time spent was noted. CPP score was calculated by subtracting the time spent in gabapentin paired chamber on the pretest day from that of the posttest (CPP score=Posttest−Pretest).

Formalin test: The formalin test was carried out in a square plexiglass chamber, 10 µl of 5% formalin was administered into the plantar surface of the right hind paw. The control mice were injected with 10 µl of saline. Each mouse was immediately placed in the observation chamber after injection, and the time licking the injected hind paw was recorded during the early (0 to 15 minutes) and delay (15 to 30 minutes) phases. These results were expressed as the means±S.E.M. of licking time in seconds.

Fear conditioning: Fear conditioning was performed as previously described (Yadav et al. *PLoS One.* 2013; 8(4): e60785) with some modifications. For fear conditioning, mice were placed in a plexiglas rodent conditioning chamber (chamber A; model 2325-0241 San Diego Instruments, San Diego, CA, USA) with a metal grid floor, enclosed in a sound-attenuating chamber and illuminated with white light. On day 0, mice were habituated to chamber for 30 min. On the day of conditioning (day 1) mice were placed in chamber for 3 min followed by five CS-US pairings (5 CS-US). The CS was a tone (85 db, 3 kHz) delivered for 30 sec with a 1 min inter-trial interval (ITT). The US was a 0.5 mA footshock delivered for 2 sec that terminated together with the CS. Mice were removed from chamber 1-2 min after the final CS-US pairing. On testing day 2 (post-test), mice were placed in the novel Plexiglas chamber with different olfactory and visual cues and the metal grid is replaced with solid Plexiglass floor. Behavioral freezing response was measured as absence of all non-respiratory movements every five seconds before and after presentation of the US for conditioning (day 1) and during post-test (day 2). Percent freezing was calculated by averaging scores of 0 for immobility and 1 for movement and divided by the total number of readings.

Behavioral Assessment Tests in Rats

Vocalization: Rats vocalizations in the audible and ultrasonic (25±4 kHz) ranges were measured using a condenser microphone and a bat detector, respectively, which were placed in front of the animal at a fixed distance in a in a custom designed recording chamber (U.S. Pat. No. 7,213, 538; Ji et al. *J. Neurosci.* 2017; 37(6):1378-1393; Ji et al. *Mol. Pain.* 2018; 14: 1744806918804441). Animals were anesthetized briefly with isoflurane (2%) and placed in a custom-designed recording chamber with openings for head and limbs. After recovery and habituation to the chamber, mechanical stimuli of innocuous (100 g/6 mm2) and noxious (500 g/6 mm2) intensities were applied to the hindpaw (15 s) using calibrated forceps with a force transducer to monitor the applied force (in g). Durations of audible and ultrasonic vocalizations were analyzed for 1 min using Ultravox 2.0 software (Noldus Information Technology).

Von Frey test: von Frey test in rats was performed with a series of von Frey filaments (Touch Test sensory evaluators; Stoelting, Wood Dale, IL), and withdrawal threshold was calculated using the Dixon up-down method (Dixon. *Neurosci. Biobehav. Rev.* 1991; 15(1):47-50). Hindpaw withdrawal threshold was tested by perpendicular application of the filaments to the plantar surface of the left (ipsilateral to SNL) paw; the cutoff filament was 15 g.

Elevated plus maze: Elevated plus maze (EPM, Columbus Instruments, (arm length, 50 cm; arm width, 10 cm; and wall height, 40 cm) was used to test for anxiety-like behaviors. After habituation to the behavior room for 1 hr, the animal was placed in the central area of the EPM, facing an open arm. Movement in the open and closed arms of EPM were measured as number of entries into the respective arm, for 15 min using a computerized analysis system (Multi-Varimex software; Columbus Instruments). The ratio of open-arm entries to the total number of entries calculated as percentage during the first 5 min is reported (Ji et al. *Mol. Pain.* 2018; 14:1744806918804441).

Statistics

All data are presented as mean±SEM. Data were analyzed using Student's parametric two-tailed unpaired t-test, one-way ANOVA or two-way ANOVA with post-hoc multiple comparisons test. Differences were considered significant if $p<0.05$. Prism 7 (GraphPad Software Inc., San Diego, CA, USA) was used for analysis. Sample sizes were based on our previous analysis using similar methods. All data points are biological replicates, i.e., they represent different animals in behavior and immunohistochemistry or different neurons or brain sections (from several animals) in a brain slice for electrophysiology or immunohistochemical analysis. Blinding was employed for immunohistochemical and behavioral tests using a coding system.

Results

Unique Cell- and Input-Specific Expression of GluD1 in the Central Amygdala

Figure 2:
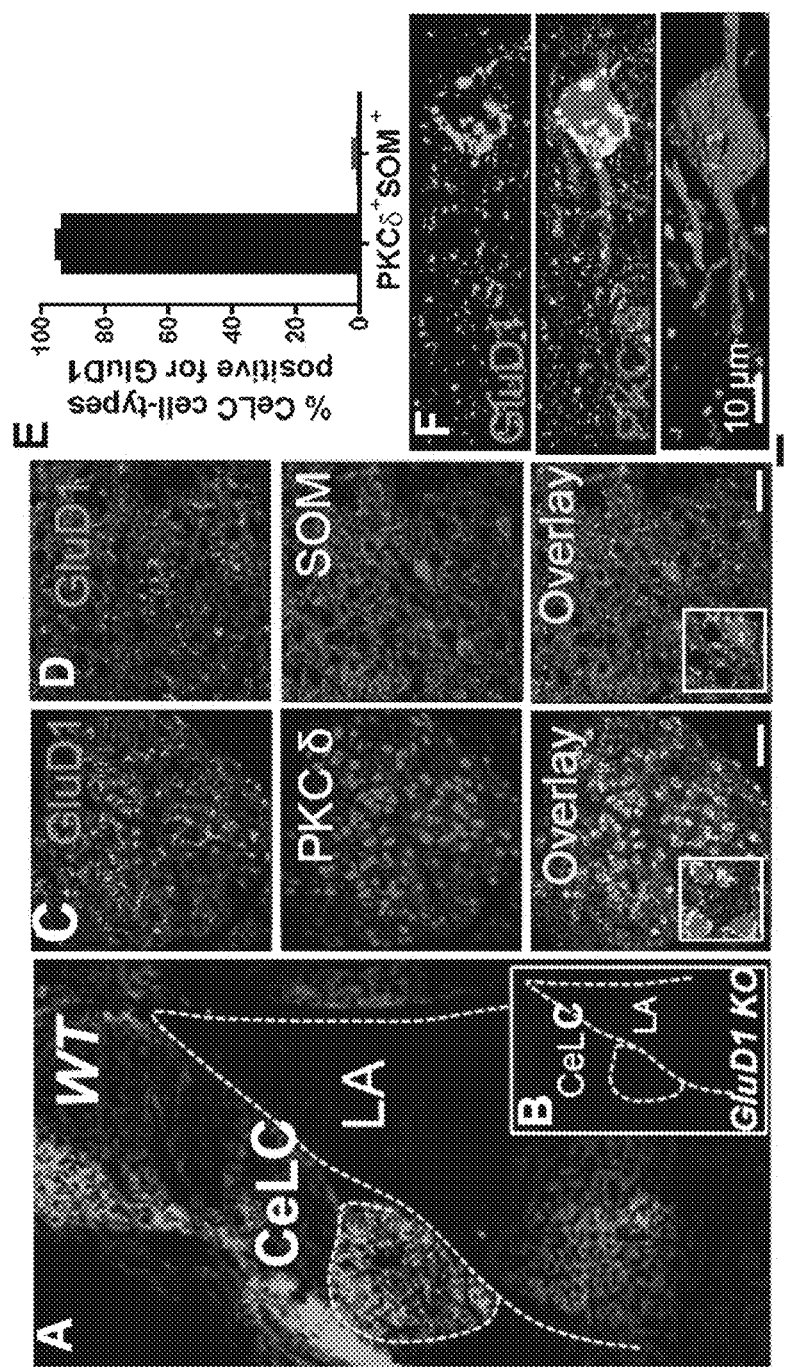
FIG. 2 has plots showing GluD1 expression.
Figures 2A, 2B:
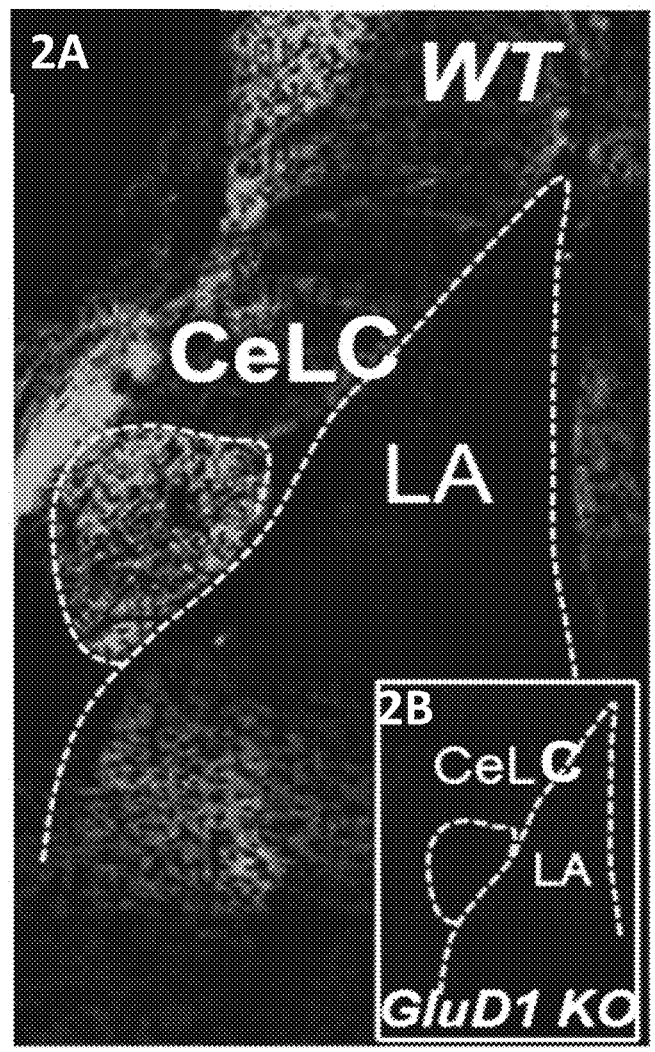
FIG. 2A is a plot showing immunohistochemical analysis of GluD1 in CeLC.
FIG. 2B is a plot showing antibody specificity.
Figure 2C:
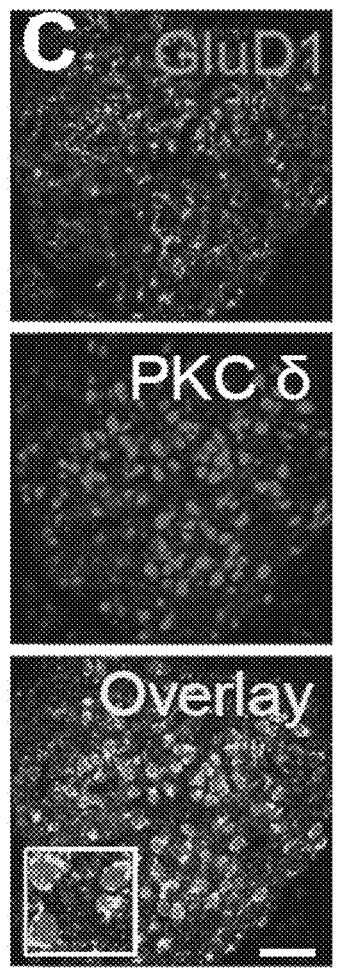
FIG. 2C is a plot showing GluD1 shows labeling on PKCδ+ neurons.
Figure 2D:
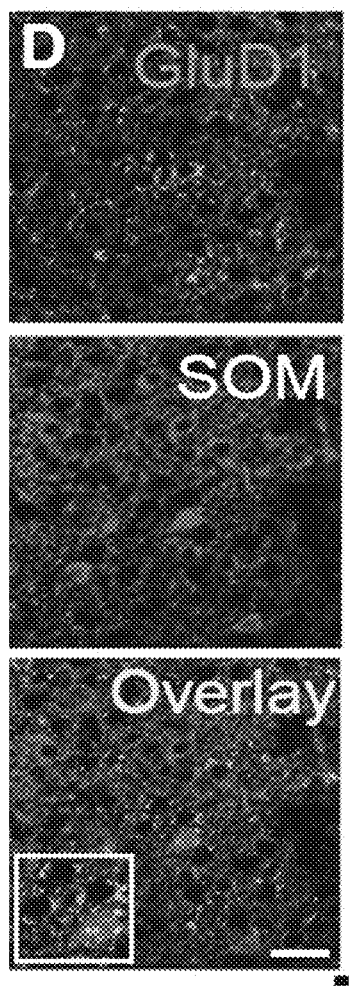
FIG. 2D is plot showing negligible colabeling with SOM+ neurons.
Figure 2E:
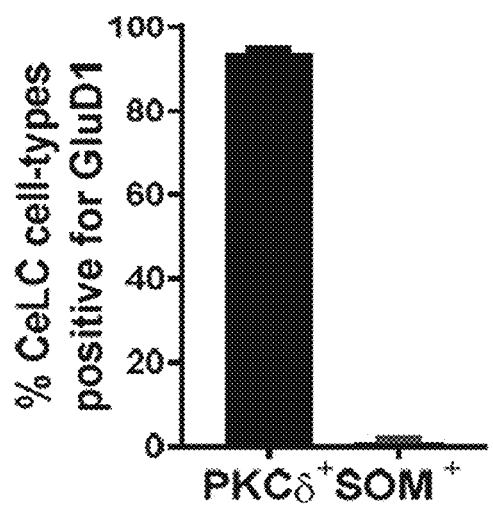
FIG. 2E is a plot showing quantification of GluD1 colocalization in both neuronal populations reveals 93.49±1.104% were PKCδ+ whereas only 0.788±0.572% were SOM+(n=5 mice).
Figure 2F:
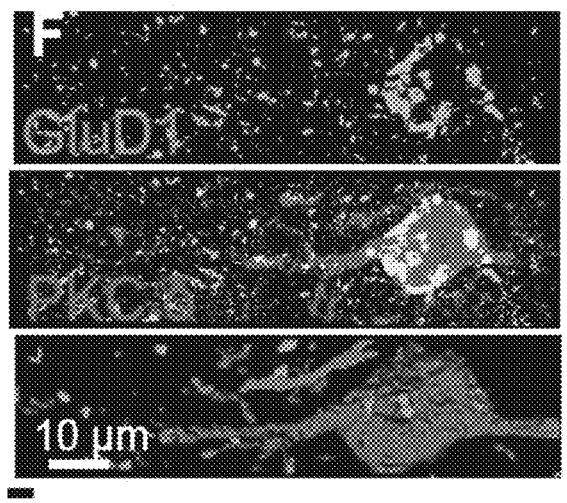
FIG. 2F is a plot showing a 3-D reconstruction of GluD1 puncta on PKCδ+ neurons.
Figure 3A:
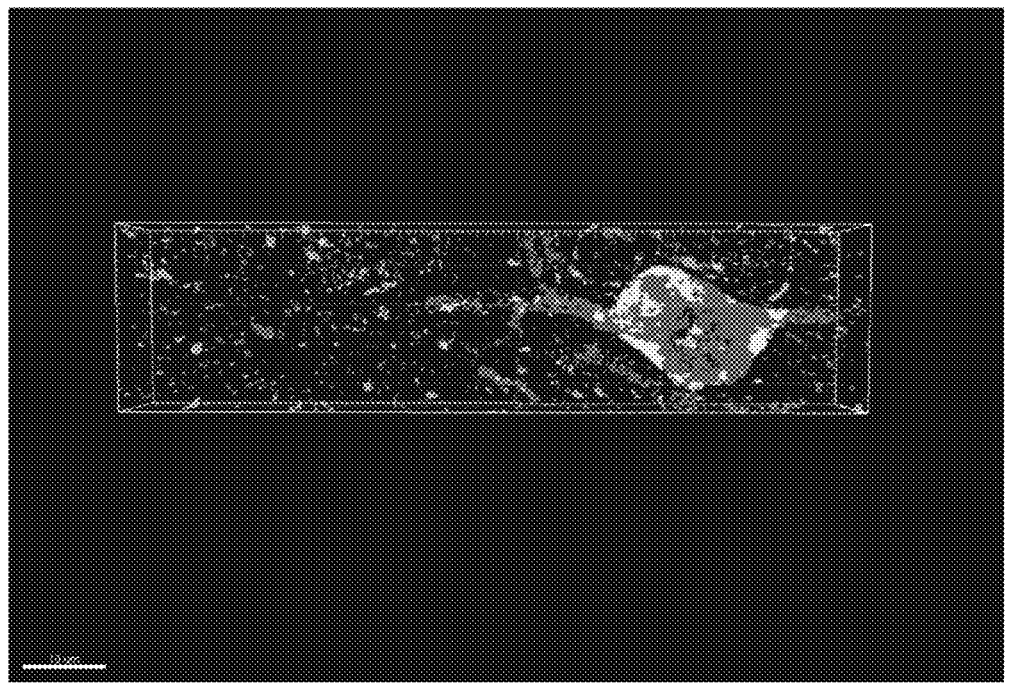
FIG. 3A is a plot showing a snapshot from a 3D reconstruction video of GluD1 (green) localization on PKCδ+ neurons (red) in the CeA.
Figure 3B:
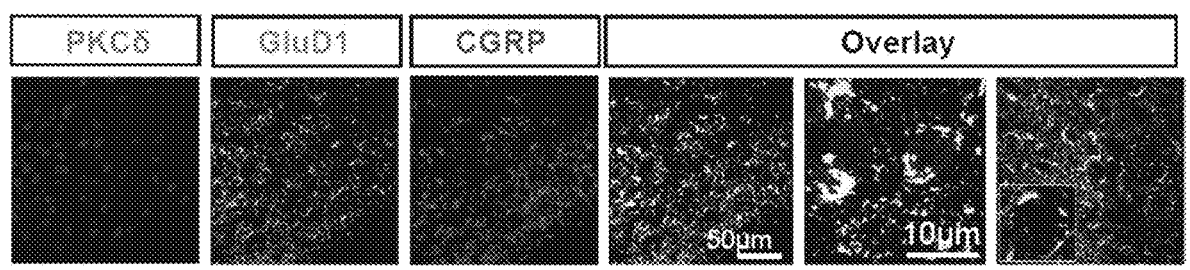
FIG. 3B is a plot showing Colocalization of GluD1, CGRP and PKCδ in the CeA.

The expression of GluD1 in the CeA along the spino-parabrachio-amygdala pathway was examined (FIG. 1) which comprises of glutamatergic PB neurons including CGRP+ cells projecting to CeLC. Strong expression of GluD1 was observed in CeA consistent with previous reports. The expression was found to be both punctate as well as perisomatic (FIG. 2*i*, vi). The expression was observed in CeC and CeL regions but not in CeM region. Predominant CeA cell types include two non-overlapping populations expressing PKCδ or somatostatin (SOM). Majority of perisomatic and punctate GluD1 was found to localize with PKCδ+ neurons. This was also evident from the 3D-reconstruction constructed images (FIG. 2*iii-vi*, FIG. 3A). GluD1 did not localize to either the soma or the dendritic elements of SOM neurons.

Figure 4:
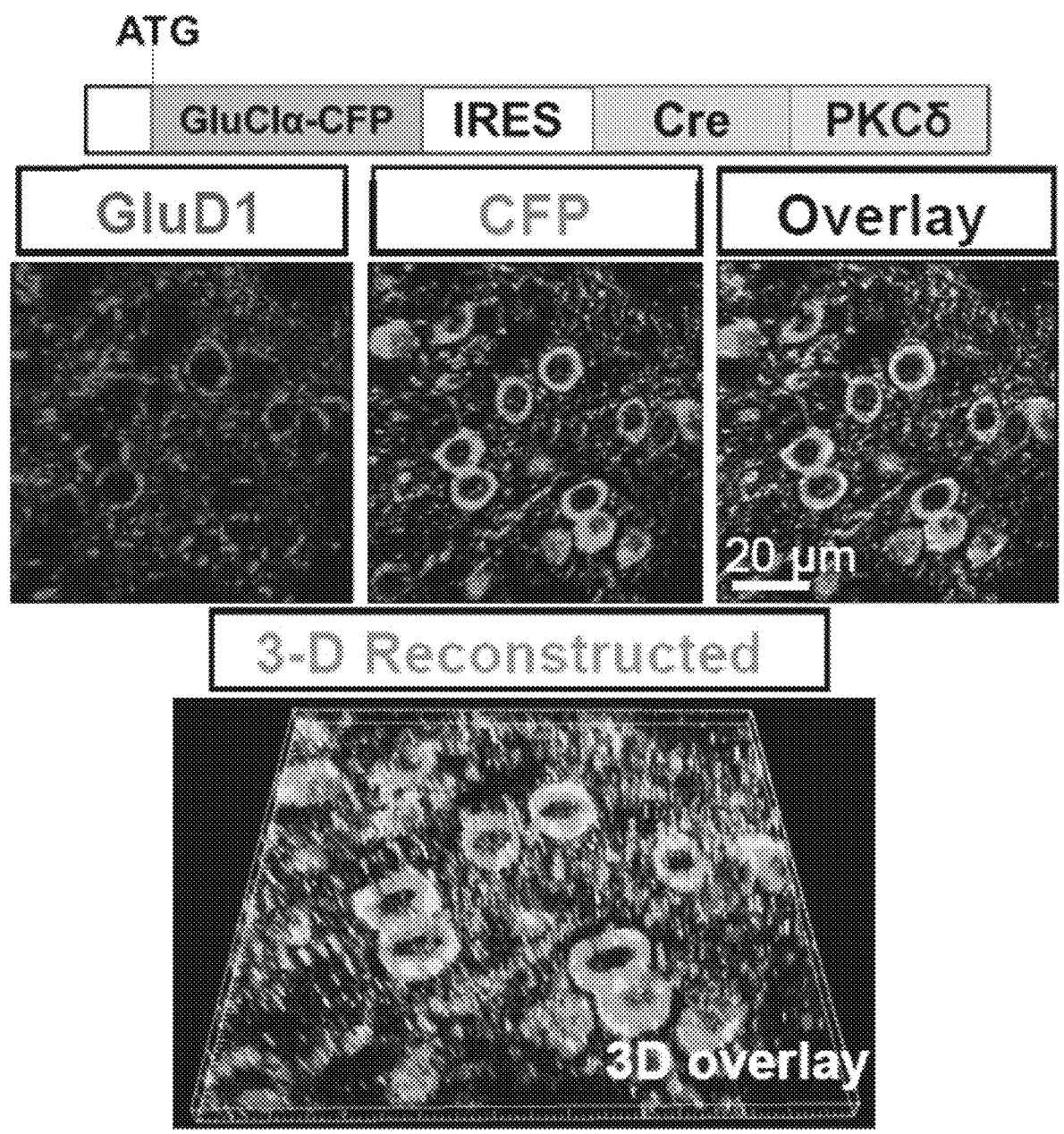
FIG. 4 is a plot showing GluD1 localization to PKCδ+ neurons using the PKCδ- CFP-Cre reporter mouse line.

Localization of GluD1 on PKCδ+ neurons was also confirmed in a PKCδ reporter model (FIG. 4). This reporter model expresses GluC1-CFP under the PKCδ promoter. Labeling for CFP together with GluD1 revealed co-localization further demonstrating localization of GluD1 with PKCδ+ neurons.

Figure 3C:
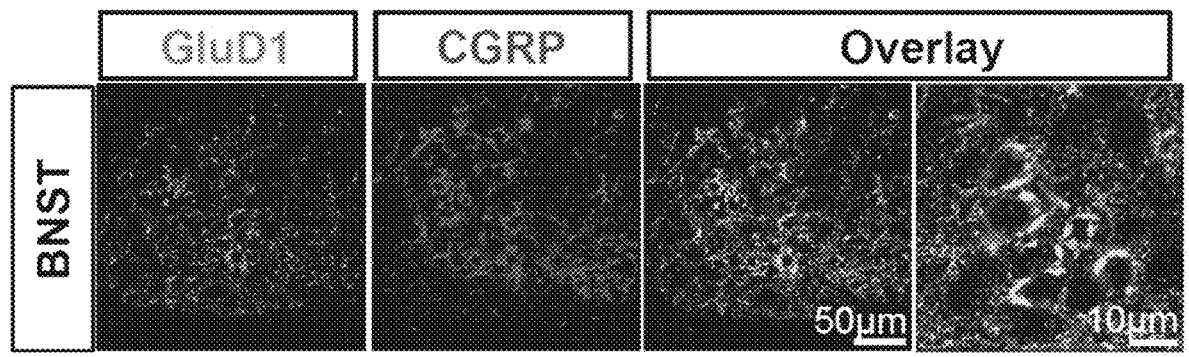
FIG. 3C is a plot showing GluD1 and CGRP show colocalization in BNST. Immunohistochemistry for GluD1 and CGRP in BNST demonstrate that CGRP ensheathes perisomatic. GluD1 with basket like structure, similar to the pattern observed in CeLC.
Figure 3D:
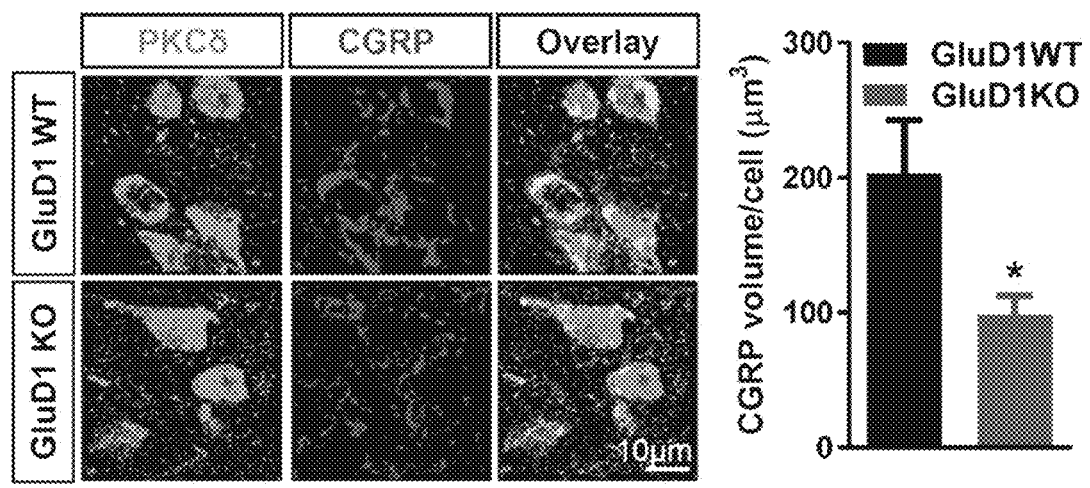
FIG. 3D is a plot showing GluD1 deletion leads to significant reduction in CGRP projection in CeLC. Immunohistochemistry for CGRP in WT and GluD1 KO exhibit significant reduction in CGRP in CeLC suggesting an impairment in PB inputs. (WT vs GluD1 KO: 203.0±39.46 vs. 97.86±14.54, p<0.05, Unpaired t-test, n=7-10 neurons from 3 mice per 10 genotype).
Figure 5:
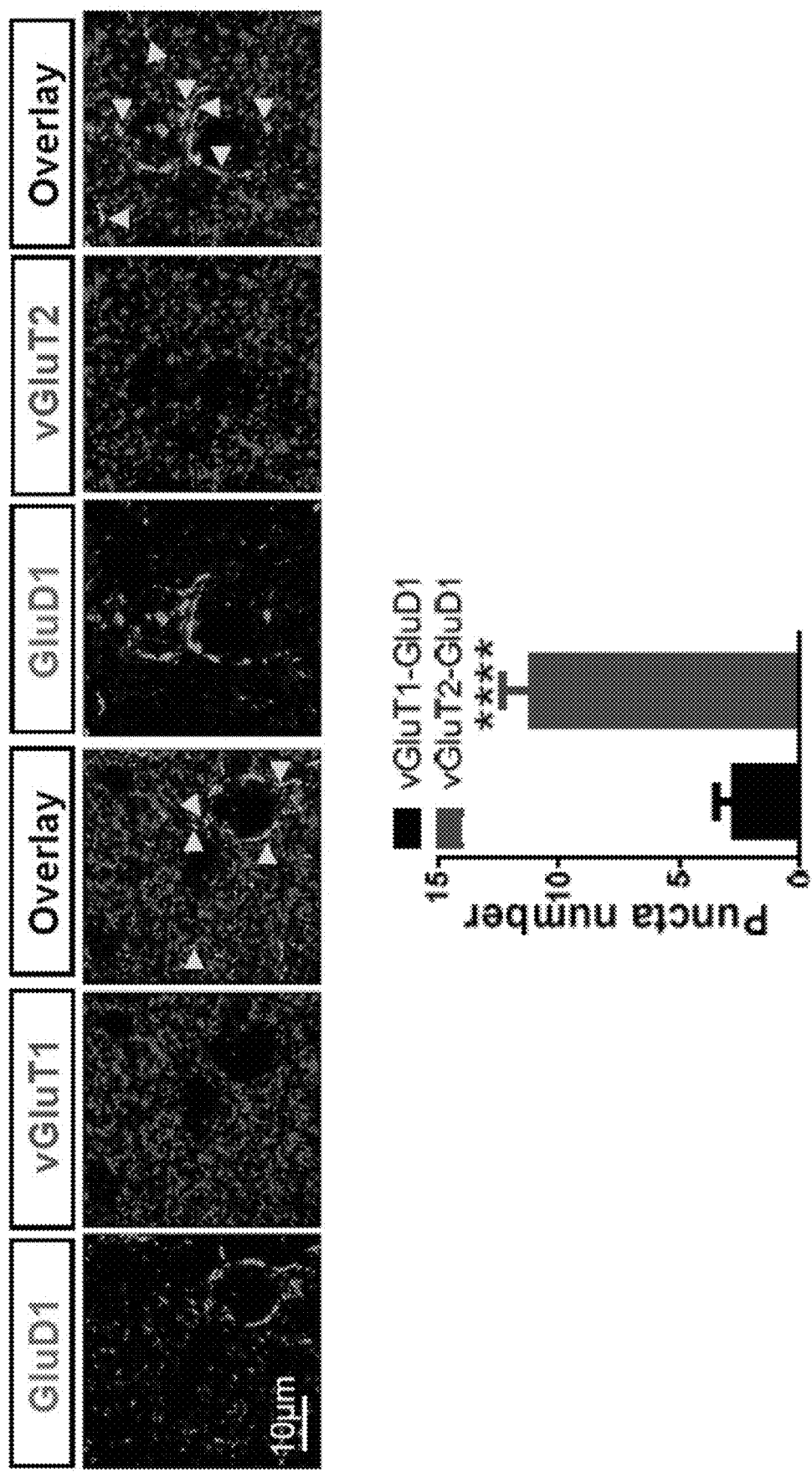
FIG. 5 has plots showing higher colocalization (arrows) of GluD1 with PB marker vGluT2 vs BLA marker vGluT1 (vGluT1-GluD1: 2.857±0.6521, n=21; vGluT2-GluD1 11.22±1.14, n=9 images from 3 mice per group, ****p<0.0001, two-tailed unpaired t-test).
Figure 6:
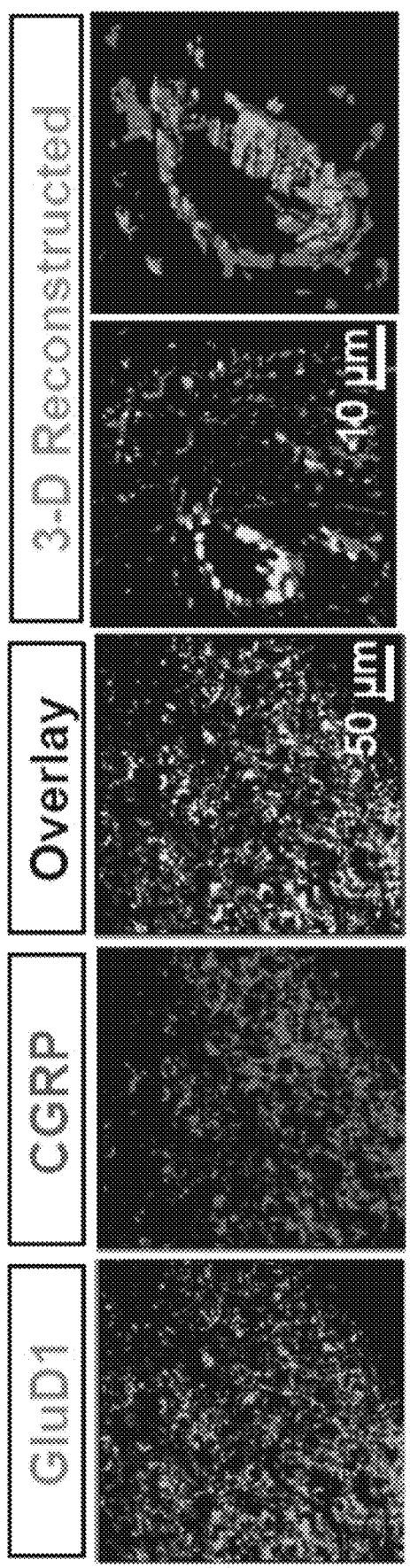
FIG. 6 has plots showing GluD1 is postsynaptic to CGRP terminals. Confocal analysis and 3-D reconstruction reveal close apposition of GluD1 with CGRP.

Whether GluD1 is localized to specific projections to CeA, which may further suggest its functioning as a synaptic organizer, was also examined. CeA receives major projections from PB and basolateral amygdala (BLA) which can be distinguished by their expression of vGluT2 and vGluT1 respectively (Lein et al. 2007; Nature. 445:168-176). GluD1 was found to primarily localize with PB projections as evidenced by stronger vGluT2 co-localization compared to BLA projections which are vGluT1+(FIG. 5). Evidence suggests that PKCδ+ neurons are the main targets of synapses from PB-calcitonin gene-related peptide (CGRP)+ neurons (see, e.g., de Lacalle & Saper. Neuroscience. 2000; 100:115-130; D'Hanis et al. J. Comp. Neurol. 2007; 505:

268-291), while SOM+ neurons receive inputs from primarily PB-CGRP-cells (see, e.g., de Lacalle & Saper. *Neuroscience.* 2000; 100:115-130). GluD1 was found to exist on the cell soma in close apposition with CGRP elements and 3D-reconstruction suggested the localization of CGRP to be presynaptic (FIG. 6, 3B). Similar pattern was observed in the extended amygdala bed nucleus of the stria terminalis (BNST) region (FIG. 3C).

GluD1 is Necessary for Normal Excitatory Neurotransmission at the Parabrachio-Amygdala Synapses.

Figure 7:
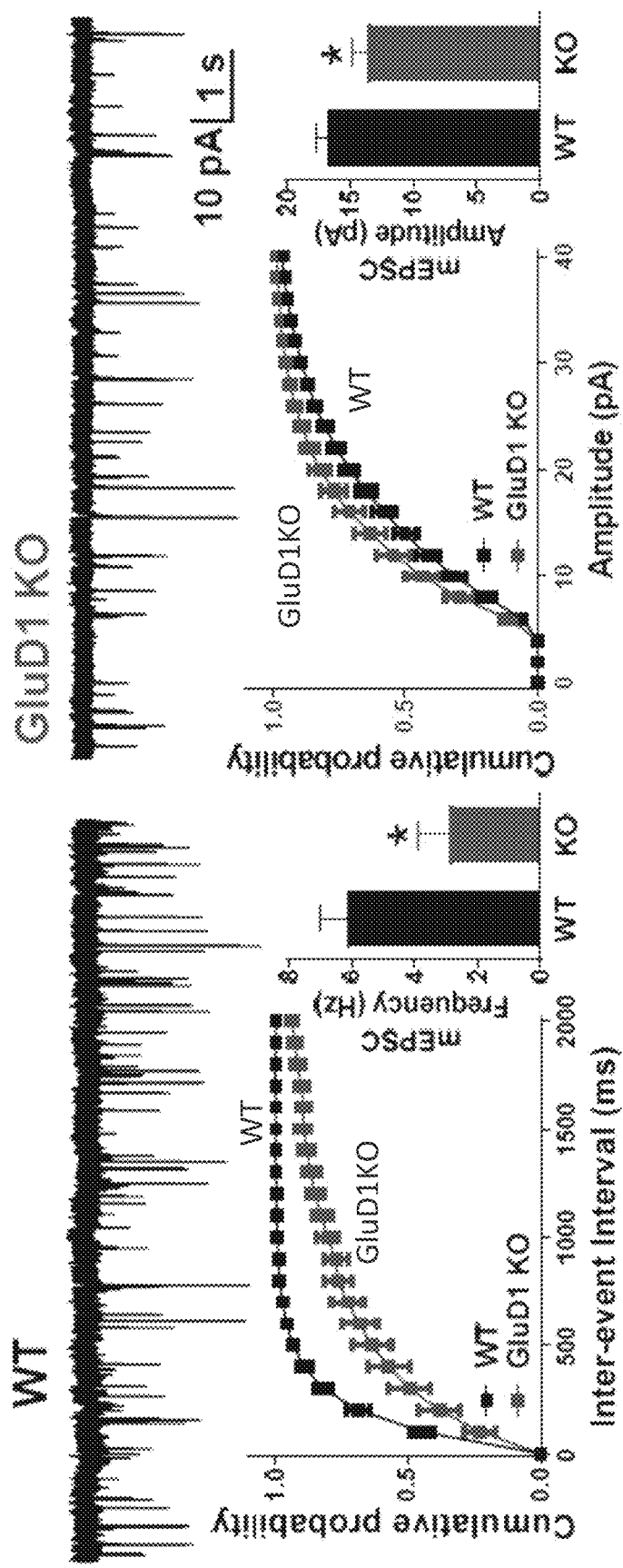
FIG. 7 has plots showing whole-cell mEPSC recordings at –70 mV (in the presence of picrotoxin and tetrodotoxin) from CeC neurons demonstrate significantly lower mEPSC frequency and amplitude in GluD1 KO (WT vs. GluD1 KO: Frequency: 6.17±0.8331 Hz vs. 2.914±0.9627 Hz, p=0.0233, unpaired t-test; Amplitude: 16.78±0.869 pA vs. 13.66±1.124 pA, p=0.0478, unpaired t-test, n=8-9 neurons from 3 mice in each genotype).
Figure 8A:
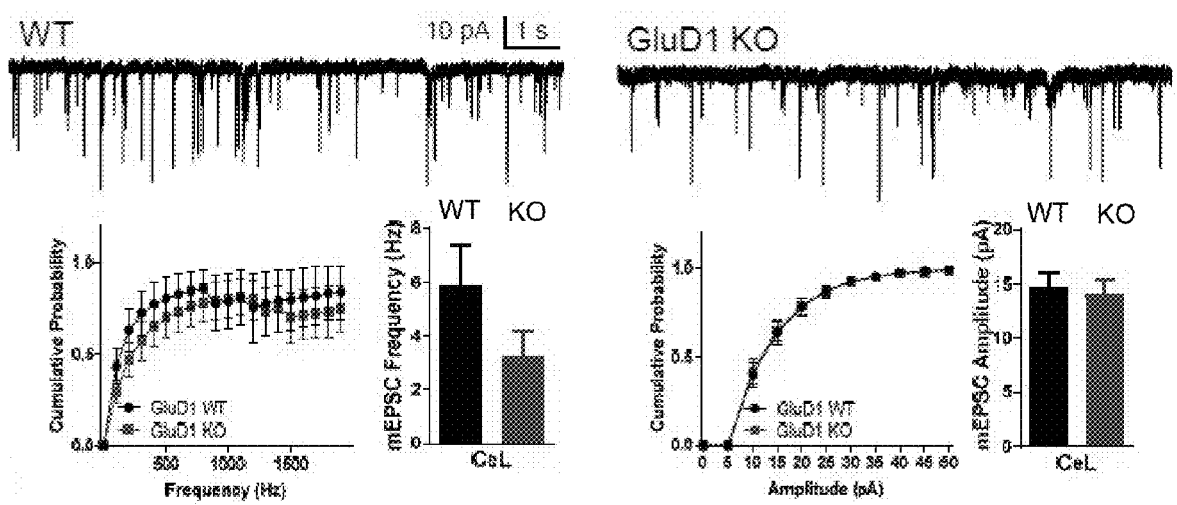
FIG. 8A is a plot showing a modest but no significant effect of GluD1 deletion on excitatory neurotransmission in CeL neurons (p=0.1566, Unpaired t-test, n=8 neurons from 3 mice per genotype). The reduction in mEPSC frequency in CeL is less compared to CeC (FIG. 7).
Figure 8B:
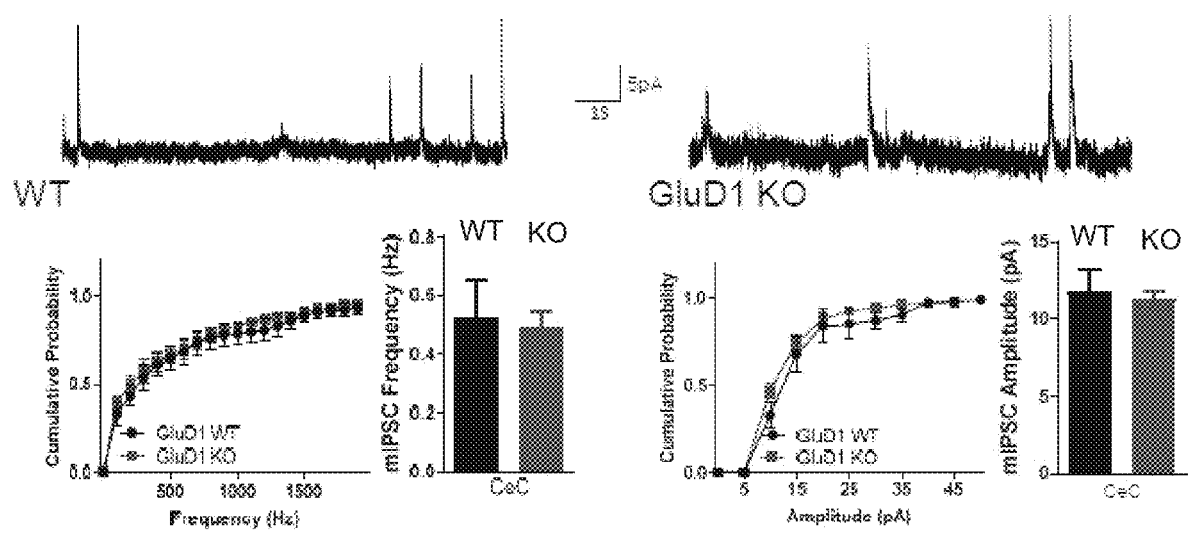
FIG. 8B is a plot showing no change in mIPSC frequency and amplitude in CeC due to deletion of GluD1 (p=0.7438, Unpaired t-test, n=8 neurons from 3 mice per genotype).
Figure 8C:
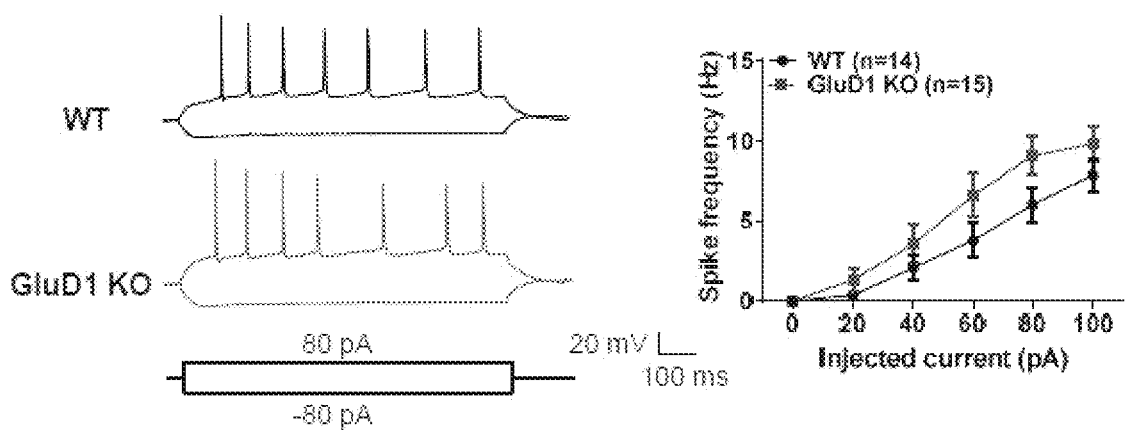
FIG. 8C is a plot showing no significant change in excitability of CeC neurons in GluD1 KO mice (80 pA: p:0.1419, Two-way ANOVA with Bonferroni's post-hoc test, n=14-15 neurons from 3 mice per genotype).
Figure 9:
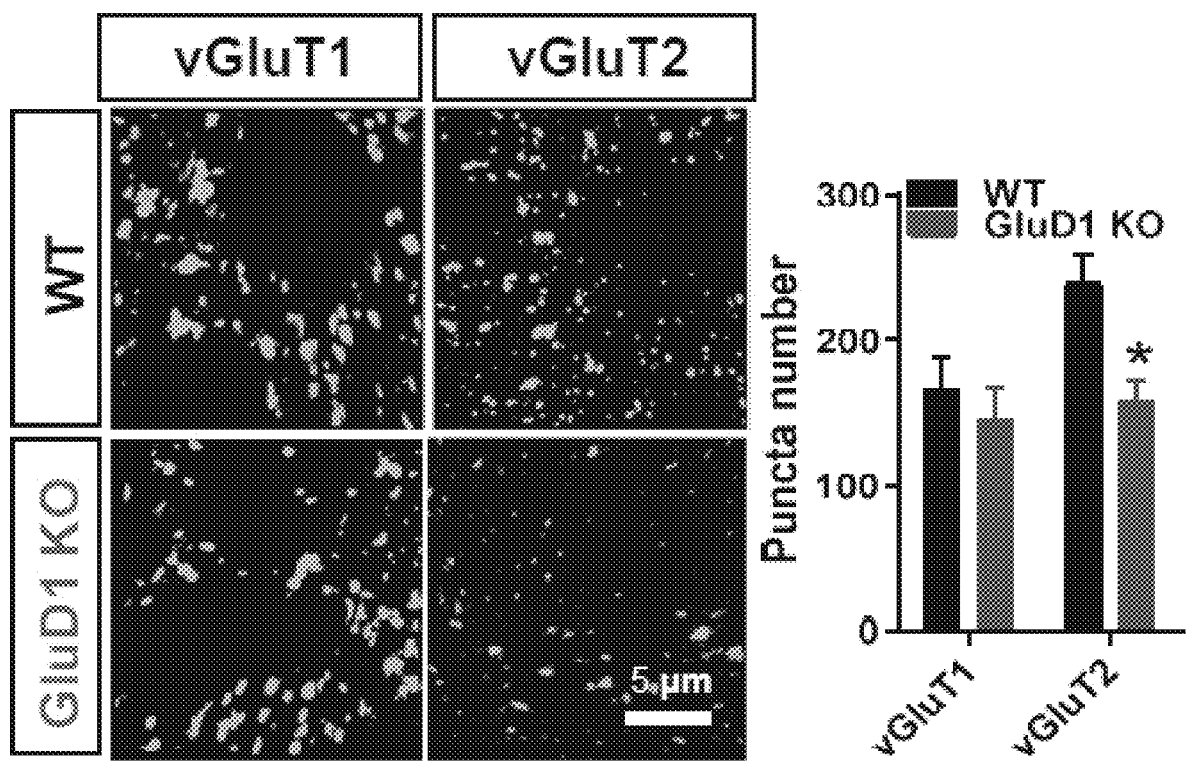
FIG. 9 has plots showing selective reduction in vGluT2 puncta in CeLC in GluD1 K mice (vGluT1: WT vs. GluD1 KO: 166.750±21.379 vs. 145.5±22.29; vGluT2: WT vs. GluD1 KO: 239±19.759 vs. 158.25±13.665, p=0.0249, Two-way ANOVA with Bonferroni's multiple comparisons test, n=4 mice per group).
Figure 10:
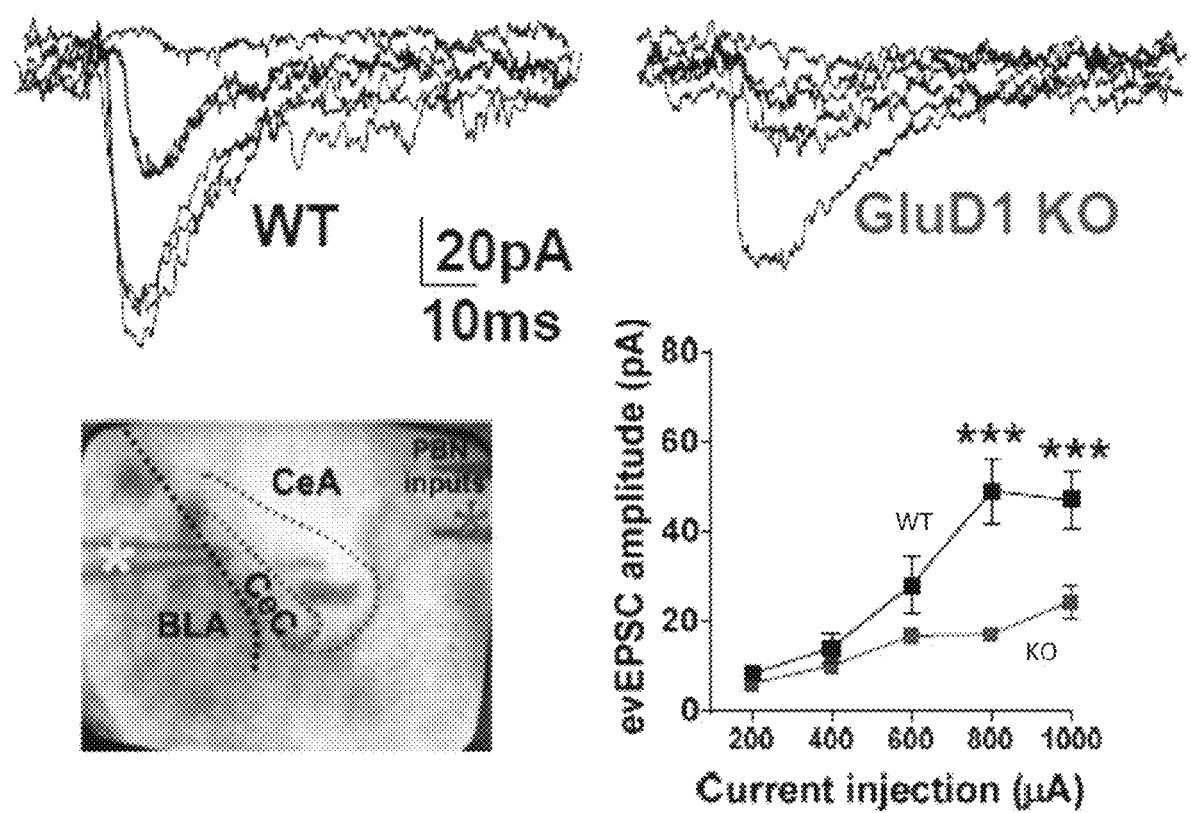
FIG. 10 has plots showing whole-cell evoked EPSCs from CeC neurons at –70 mV in the presence of picrotoxin with recording electrode in CeC (yellow asterisk) and stimulating electrode on PB fibers (red asterisk). Input-output curve shows significant reduction in evoked EPSC amplitude in GluD1 KO mice. (WT vs. GluD1 KO; 800 µA current injection: 48.966±7.389 vs. 17.164±1.43, p<0.0001; 1 mA current injection: 47.003±6.404 vs. 24.467±3.585, p=0.0002; n=15-25 neurons from 3 mice per genotype; Two-way ANOVA with Bonferroni's multiple comparisons test).

Whether GluD1 is obligatory for normal excitatory neurotransmission in the CeA was also examined. GluD1 deletion led to a reduction in mEPSC frequency as well as amplitude in CeLC neurons (FIG. 7). This effect was more robust in the CeC compared to CeL (FIG. 8A), which corresponds to the distribution of CGRP+ projections. No change in inhibitory neurotransmission (FIG. 8B) or excitability (FIG. 8C) of CeC neurons was observed in GluD1 KO mice. Whether there are changes in excitatory terminals in the CeA of GluD1 KO mice was also examined. A reduction in vGluT2 puncta and CGRP+ terminals but not vGluT1 puncta was found with GluD1 KO suggesting reduced PB- but not BLA-projection synapses (FIG. 9, 8D). Excitatory neurotransmission at the PB-CeLC synapses was also reduced in GluD1 KO condition when evoked responses were studied (FIG. 10). These results suggest an important role of GluD1 for structural and functional integrity of the PB-CeLC synapse.

Figure 11A:
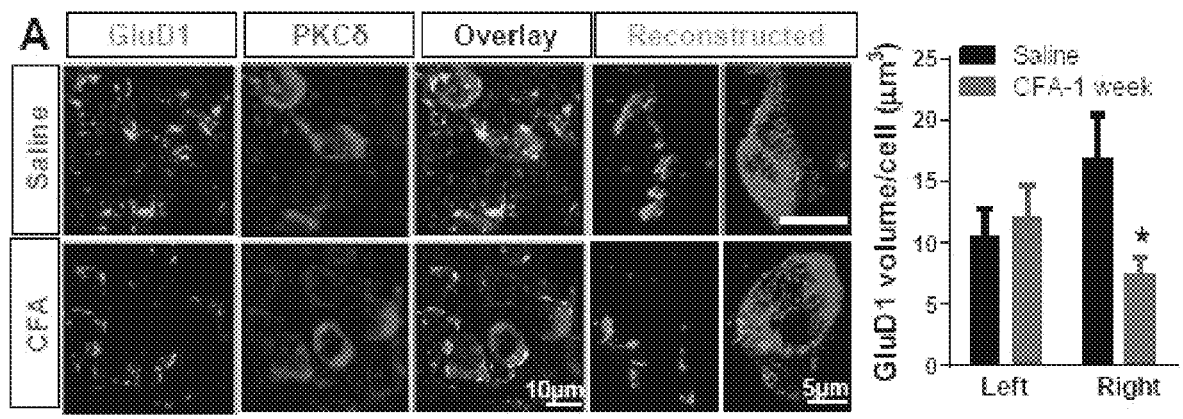
FIG. 11A has plots showing GluD1 and PKCδ staining in CeLC was performed at different timepoints after intraplantar CFA administration. 3-D reconstruction and volume analysis of GluD1 elements in apposition with PKCδ+ soma was performed. Significant reduction in somatic GluD1 volume specifically in the right CeA in CFA mice (Saline vs. CFA: left CeA: 10.521±2.212 vs. 12.161±2.563; right CeA: 16.628±3.536 vs. 7.437±1.464, p=0.0428, Two-way ANOVA with Bonferroni's post hoc test, n=16-24 neurons from 3 mice per group).
Figure 11B:
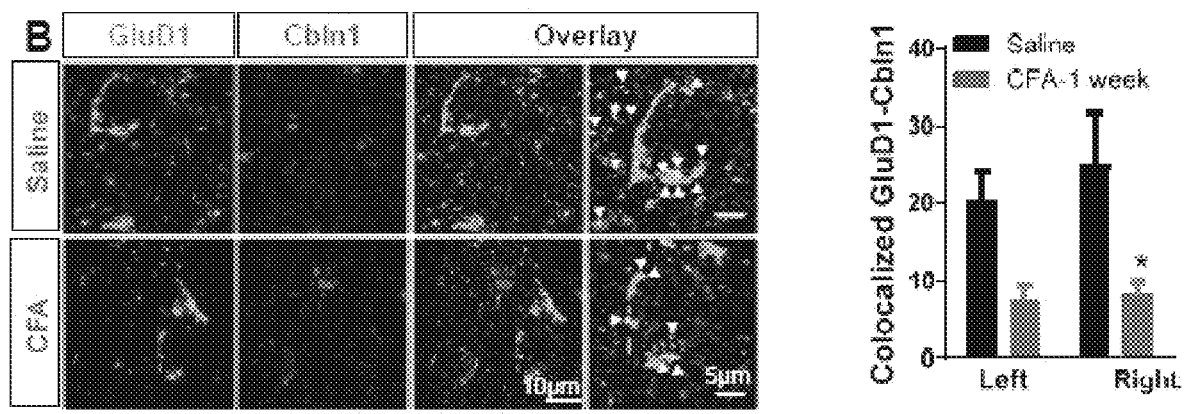
FIG. 11B has plots showing GluD1 and Cbln1 co-labeling in CeLC performed 1 week after intraplantar CFA administration. A substantial reduction in GluD1-Cbln1 colocalized puncta number in right CeA (Saline: 25.0±6.754 vs. CFA: 8.250±1.612, p=0.0111, Two-way ANOVA with Bonferroni's post hoc test) is observed. Close to significant changes are also seen in left CeA (Saline: 20.250±3.936 vs. CFA: 7.625±1.812, p=0.0525, Two-way ANOVA with Bonferroni's post hoc test, n=8 images from 3 mice in each group).
Figure 12A:
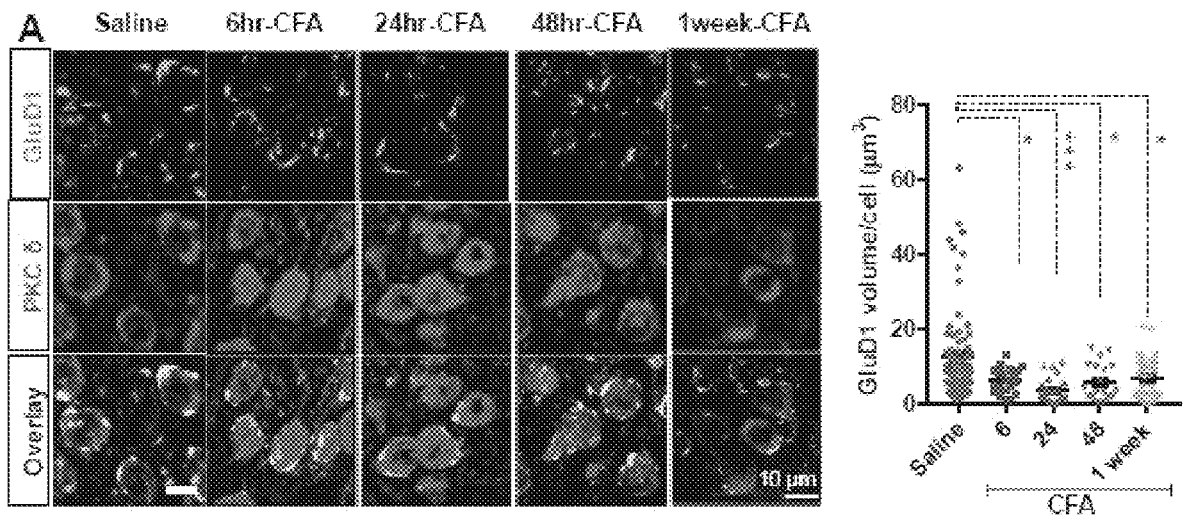
FIG. 12A is a plot showing immunohistochemistry analysis indicating the trajectory of GluD1 volume reduction around PKCδ cell at 6, 24, 48 hrs and 1-week timepoints after intraplantar CFA administration (Saline vs. CFA: 6 hrs: 12.57±1.358 vs 6.355±0.7023, p=0.0408; 24 hrs: 12.57±1.358 vs 3.557±0.7198, p=0.0003; 48 hrs: 12.57±1.358 vs 5.874±1.143, p=0.0352; 1 week: 12.57±1.358 vs 6.973±1.017, p=0.0328, One-way ANOVA with Bonferroni's post hoc test, n=19-79 neurons from 3-6 mice per group).

Downregulation of GluD1-Cbln1 in the CeLC in Inflammatory and Neuropathic Pain Models The contribution of transsynaptic GluD1-Cbln1 signaling in inflammatory and neuropathic pain was examined using complete Freund's adjuvant (CFA) in mice and spinal nerve ligation (SNL) in rats, respectively. GluD1 volume in cell soma on PKCδ+ neurons was measured along with punctate GluD1. Perisomatic and punctate expression of GluD1 was reduced in the inflammatory pain model (FIG. 11A, 12A). Interestingly, GluD1 downregulation was observed in the right CeLC but not in the left CeLC consistent with the known lateralization of pain neuroplasticity to the right amygdala (Allen et al. Prog. Neurobiol. 2020; 101891). Expression levels of GluD1 binding partner Cbln1 were also reduced in the inflammatory pain model, and the change was more significant/pronounced in the right CeA but was also observed in the left CeA (FIG. 11B).

Figure 11C:
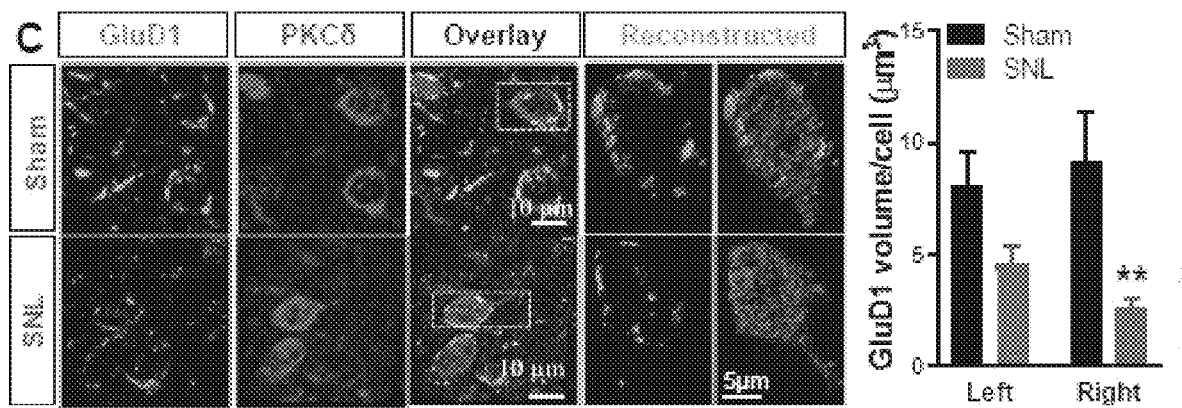
FIG. 11C has plots showing GluD1 and PKCδ co-labeling in CeLC performed 4 weeks after sham or SNL surgery in rats along with 3-D reconstruction. Significant reduction is observed in perisomatic GluD1 volume in right CeA (Sham: 9.144±2.184 vs. SNL: 2.548±0.486, p=0.0031, Two-way ANOVA with Bonferroni's post hoc test, n=19-22 neurons from 3 mice in each group). A trend but no significant change in left CeA GluD1 volume. (Left CeA: Sham: 8.069±1.534 vs. SNL: 4.538±0.802, p=0.1529; Two-way ANOVA with Bonferroni's post hoc test).
Figure 11D:
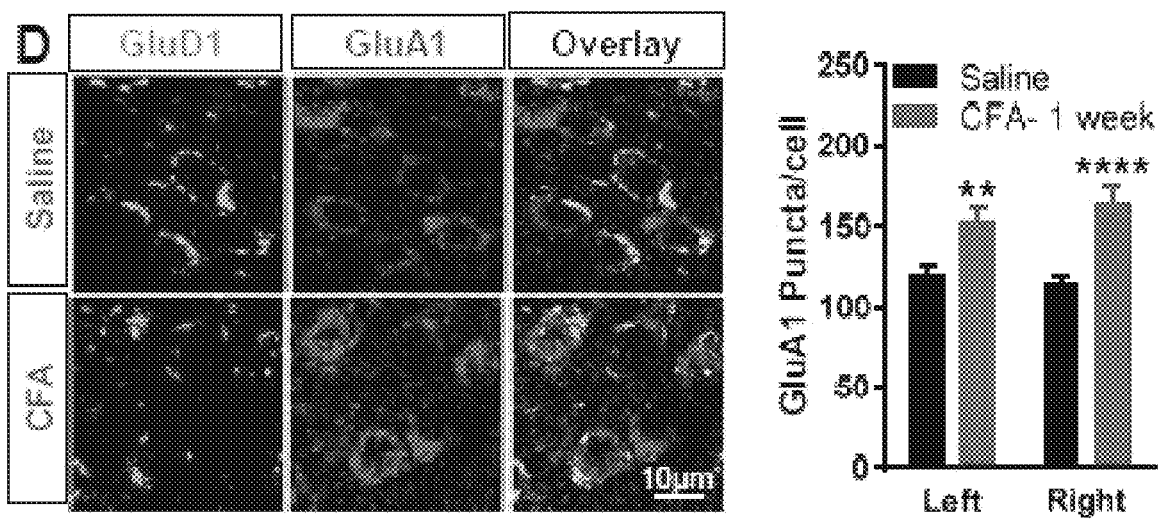
FIG. 11D has plots showing GluD1 and AMPA receptor subunit GluA1 co-labeling in CeLC performed 1 week after intraplantar CFA administration. An upregulation of surface GluA1 is observed after CFA treatment (Saline vs CFA: Left CeA: 119.173±6.134 vs. 153.159±8.098, p=0.0019; Right CeA: 115.033±4.544 vs. 164.144±9.988, p<0.0001, Two-way ANOVA with Bonferroni's post hoc test, n=38-46 neurons from 3 mice per group).
Figure 11E:
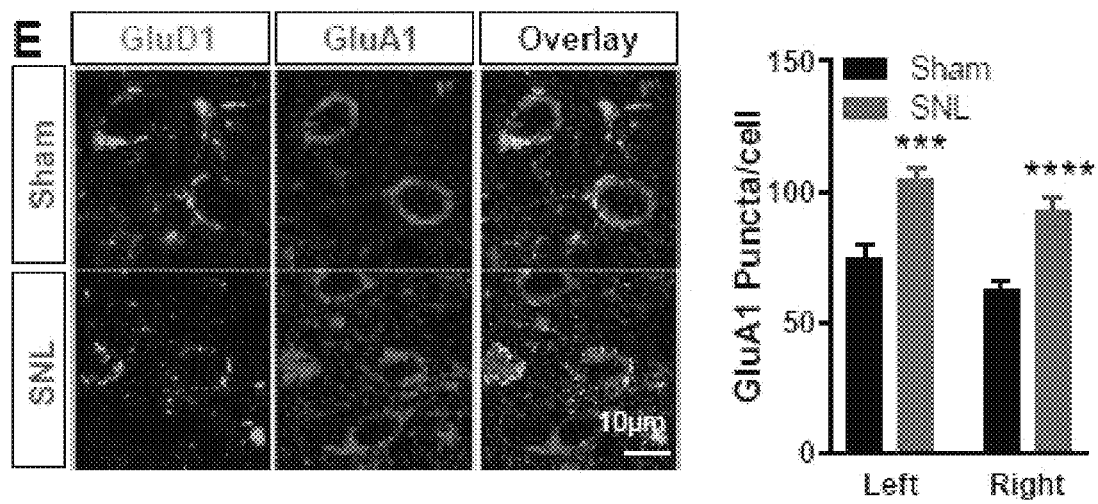
FIG. 11E Upregulation of GluA1 subunit in CeLC of SNL mice (Sham vs. SNL: Left CeA: 74.541±5.674 vs. 104.558±4.610, p=0.0002, Right CeA: 62.199±3.636 vs. 92.613±5.597, p<0.0001; Two way ANOVA with Bonferroni's multiple comparison's post hoc test, n=29-46 neurons from 3 rats per group.
Figure 11F:
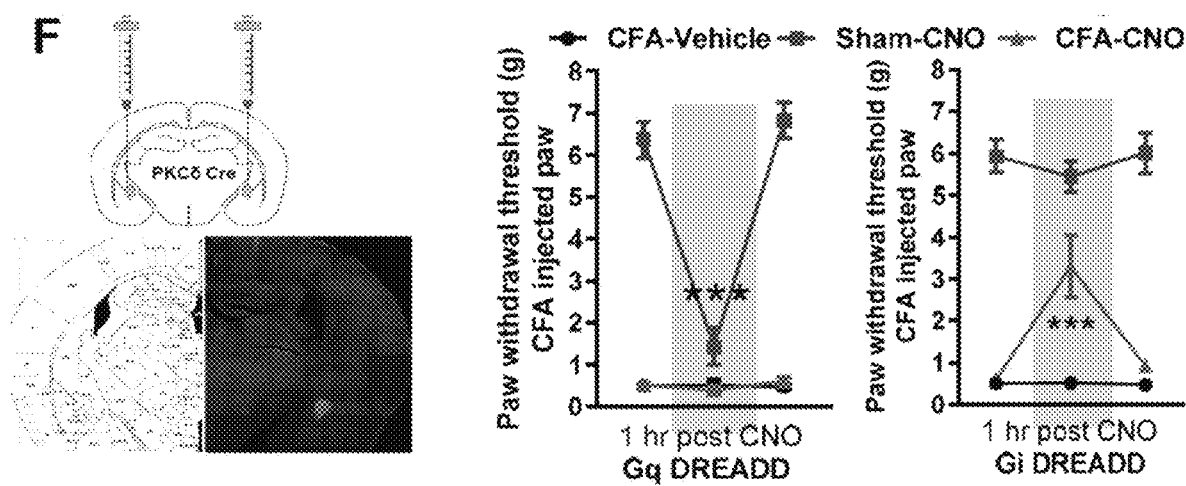
FIG. 11F has plots showing chemogenetic modulation of PKCδ neurons using PKCδ-Cre mouse line. Representative image for site verification of DREADD injection. Activation of PKCδ+ neurons in GqDREADD injected normal animals using CNO (Sham-CNO) led to an increase in mechanical sensitivity (Sham-CNO; pre-CNO vs. 1 hr post-CNO vs. 24 hrs post-CNO:6.373±0.428 vs. 1.429±0.447 vs. 6.821±0.430, p<0.0001, One-way ANOVA with Bonferroni's post hoc test, n=4-6 mice per group). In contrast, in CFA injected mice, inhibition of PKCδ+ neurons in GiDREADD injected animals using CNO (CFA-CNO) significantly rescued mechanical hypersensitivity (CFA-CNO; pre-CNO vs. 1 hr post-CNO vs. 24 hrs post-CNO: 0.591±0.040 vs. 3.289±0.748 vs. 0.925±0.129, p=0.0005, One-way ANOVA with Bonferroni's post hoc test, n=4-6 mice per group).
Figure 12B:
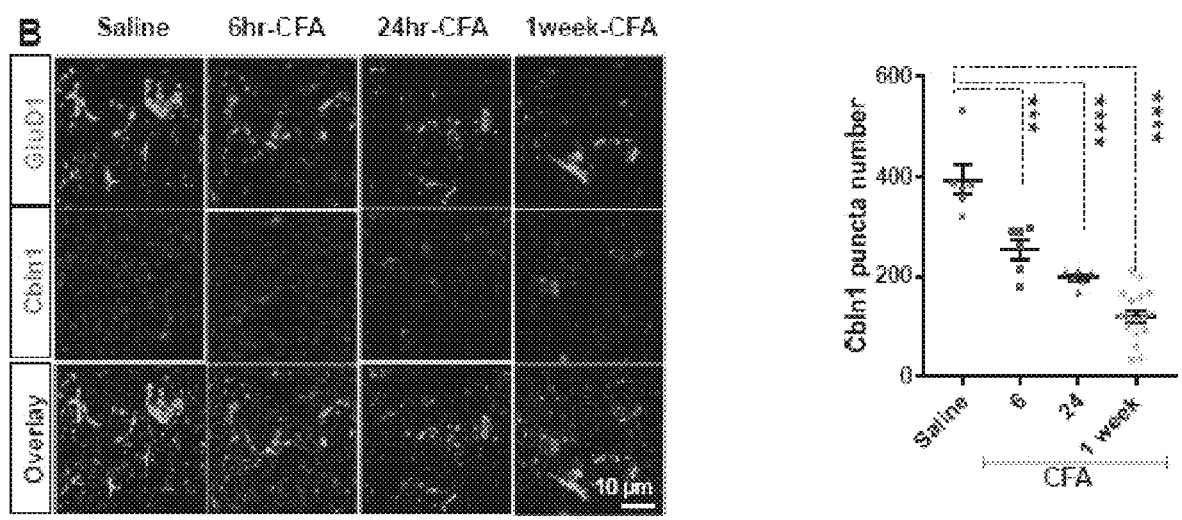
FIG. 12B is a plot showing immunohistochemistry analysis indicating the trajectory of Cbln1 puncta number reduction at 6, 24, 48 hrs and 1-week timepoints after intraplantar CFA administration (WT-Saline vs. WT-CFA: 6 hrs: 391.833±29.71 vs 254.833±19.45, p=0.0002; 24 hrs: 391.833±29.71 vs 196.500±6.791, p<0.0001; 1 week: 391.833±29.71 vs 119.8±12.4, p<0.0001, One-way ANOVA with Bonferroni's post hoc test; n=6-17 images from 3 mice per group).
Figure 12C:
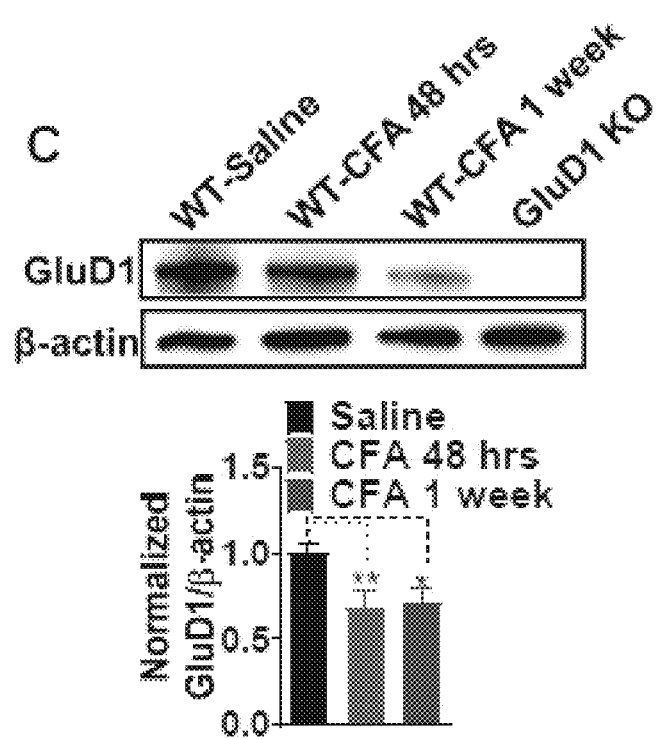
FIG. 12C is a Western blot analysis showing downregulation of GluD1 in synaptoneurosomal preparation of CeA. Induction of inflammatory pain lead to a downregulation of GluD1 in the CeA at 48 h and 1 week after CFA injection (Saline vs. CFA: 48 hrs: 1.016±0.049 vs. 0.692±0.084, p=0.0094; 1 week: 1.016±0.049 vs. 0.713±0.080, p=0.0191, one-way ANOVA with Dunnett's multiple comparison, n=6-7 mice/treatment).
Figure 12D:
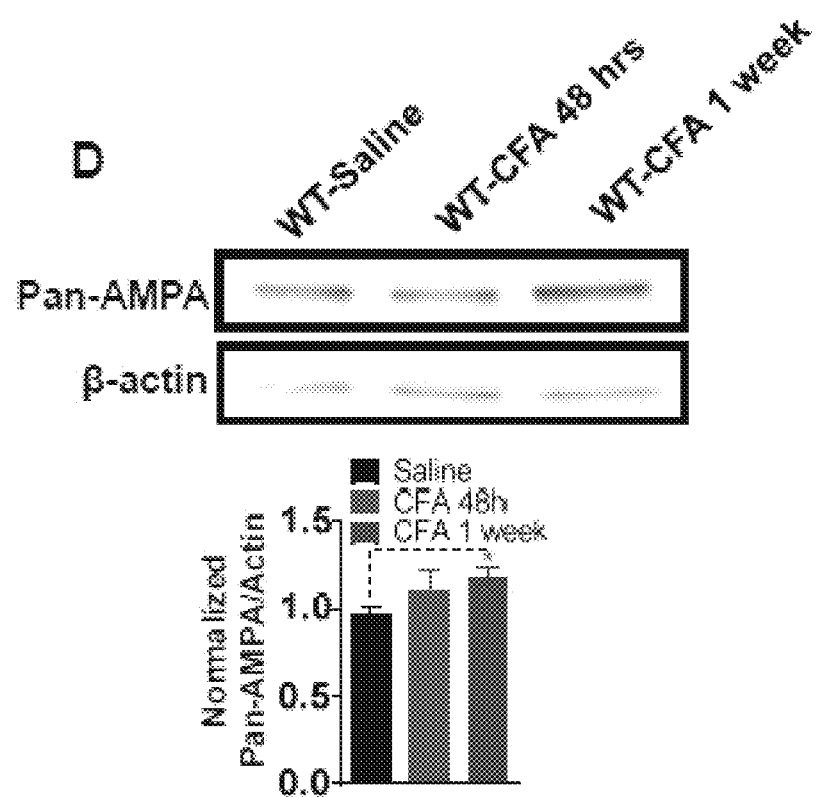
FIG. 12D is a plot showing an upregulation of AMPA receptors is observed in the model of inflammatory pain in the CeA 1 week after CFA injection (Saline vs. CFA: 1 week time point-0.975±0.032 vs. 1.169±0.066, p=0.0401, Unpaired t-test, n=4 mice/treatment).

Downregulation of perisomatic GluD1 volume around cell soma of PKCδ+ neurons was also observed in the neuropathic pain model and was more prominent in the right CeA (FIG. 11C). Examination of time-dependent changes in the GluD1 and Cbln1 expression in the right CeA in the CFA model revealed that downregulation begins as early as 6 hours and persists for at least 1 week (FIG. 12A, 12B). Changes in the distribution of AMPA receptor subunit GluA1 were examined in the pain models as a potential consequence of changes in GluD1. GluD1 downregulation was associated with an upregulation of AMPA receptor GluA1 subunit in the CFA and SNL models (FIG. 11D and FIG. 11E). Downregulation of GluD1 and upregulation of AMPA receptors was confirmed in synaptoneurosomal preparation from right CeA (FIG. 12C, 12D). To link changes in GluD1 to pain behaviors, used a chemogenetic approach was used. Because GluD1 is localized to PKCδ+ neurons, the function of PKCδ+ neurons were selectively modulated to determine its effect on inflammatory pain behaviors. Clozapine-N-oxide (CNO)-induced activation of PKCδ+ neurons expressing Gq DREADD in normal mice that received intraplantar saline injections induced mechanical hypersensitivity ("Sham-CNO", FIG. 11F left). Inhibition of PKCδ+ neurons with Gi DREADD activation did not affect mechanical thresholds in normal mice but reduced mechanical hypersensitivity in the inflammatory pain model (FIG. 11F right) confirming observations by the Carrasquillo group that overactivation of PKCδ+ contributes to inflammatory pain behaviors (see Wilson et al. Cell. Rep. 2019; 29:332-346.e5).

Figure 13:
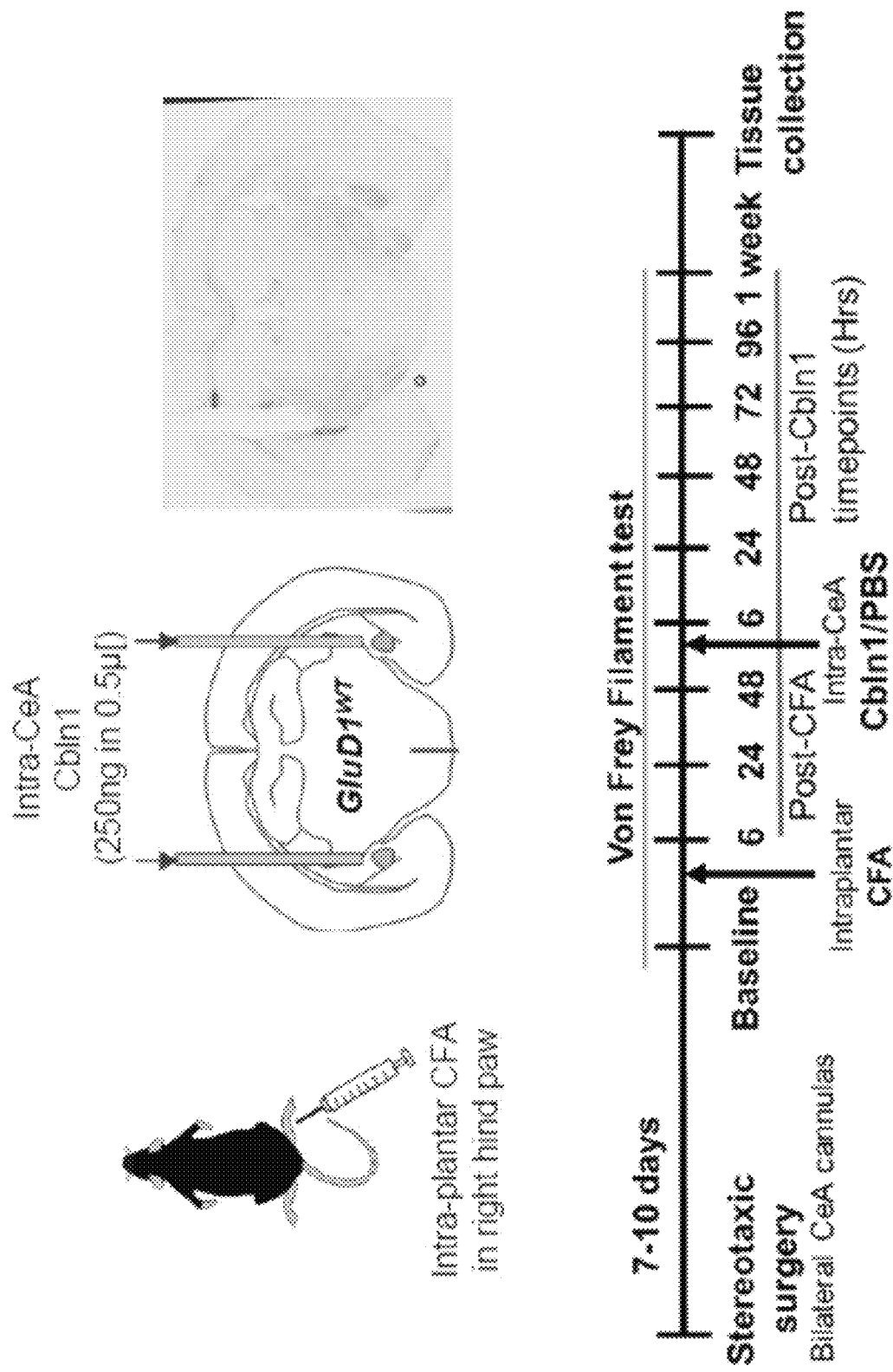
FIG. 13 has plots showing a schematic of experimental interventions.
Figure 14:
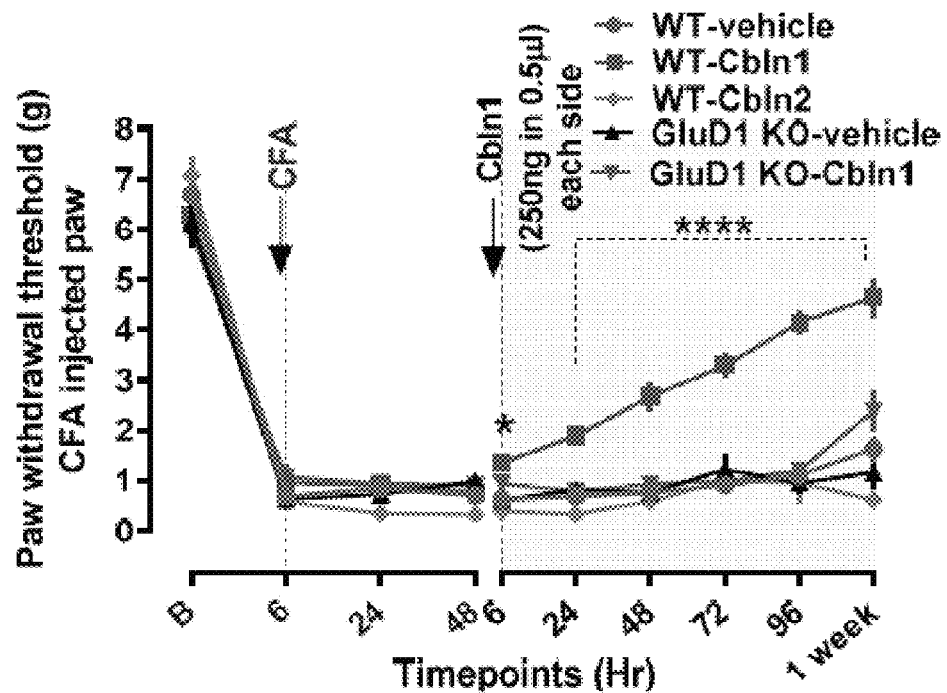
FIG. 14 has a plots showing alleviation of pain sensitivity after bilateral intra-CeA Cbln1 administration. Paw withdrawal threshold increased after a single Cbln1 injection and lasted up to a week; WT CFA-vehicle vs. WT CFA-Cbln1; 6 hrs: 0.633±0.051 vs. 1.361±0.079, p=0.0423; 24 hrs: 0.698±0.0701 vs. 1.897±0.193, p<0.0001; 48 hrs: 0.762±0.086 vs. 2.682±0.271, p<0.0001; 72 hrs: 0.908±0.0650 vs. 3.299±0.248, p<0.0001; 96 hrs: 1.113±0.121 vs. 4.156±0.213, p<0.0001 and 1 week: 1.631±0.260 vs. 4.65±0.384 p<0.0001; Two way ANOVA with Tukey's multiple comparisons, n=3-7 mice per group. This improvement was not observed in GluD1 KO (n=6 mice). Cbln2 was not able to reverse the CFA-induced mechanical hypersensitivity (n=3 mice).
Figure 15:
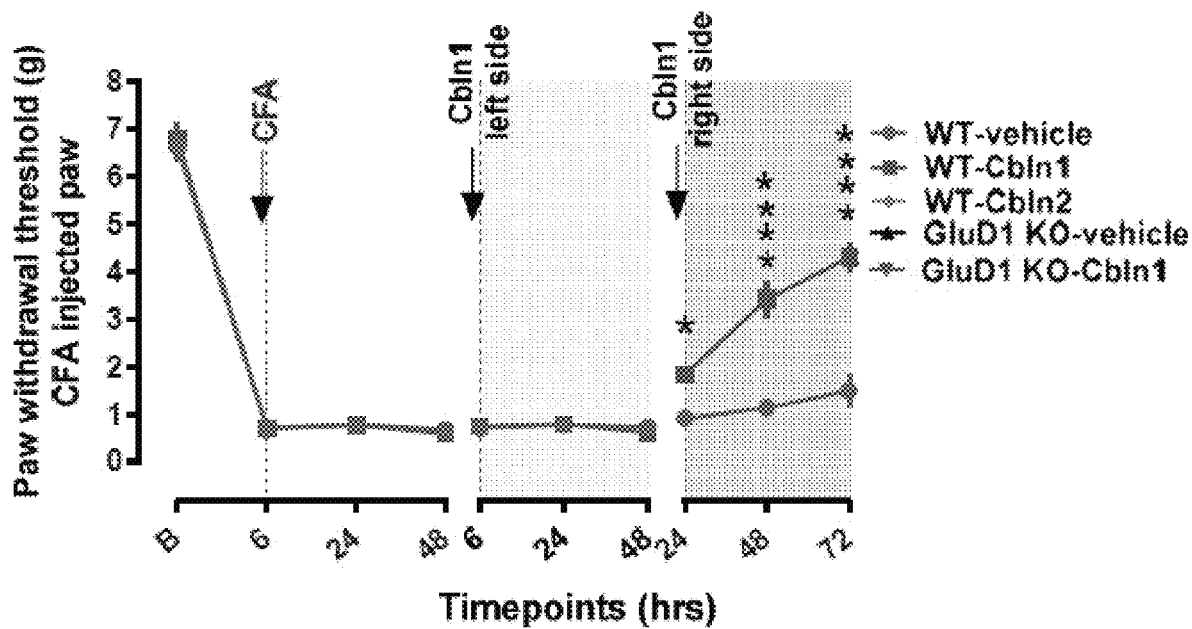
FIG. 15 is a plot showing rescue of inflammatory pain by Cbln1 injection is lateralized. Recombinant Cbln1 first injected into the left CeA did not show any rescue in mechanical hypersensitivity. However, injection into the right CeA was able to rescue mechanical hypersensitivity; WT CFA-vehicle vs. WT CFA-Cbln1; 24 hrs: 0.908±0.115 vs. 1.841±0.088, p=0.0359; 48 hrs: 1.138±0.157 vs. 3.415±0.366, p<0.0001; 72 hrs: 1.489±0.331 vs. 4.297±0.297, p<0.0001, Two way ANOVA with Bonferroni's multiple comparisons, n=3-7 mice per group.
Figure 16:
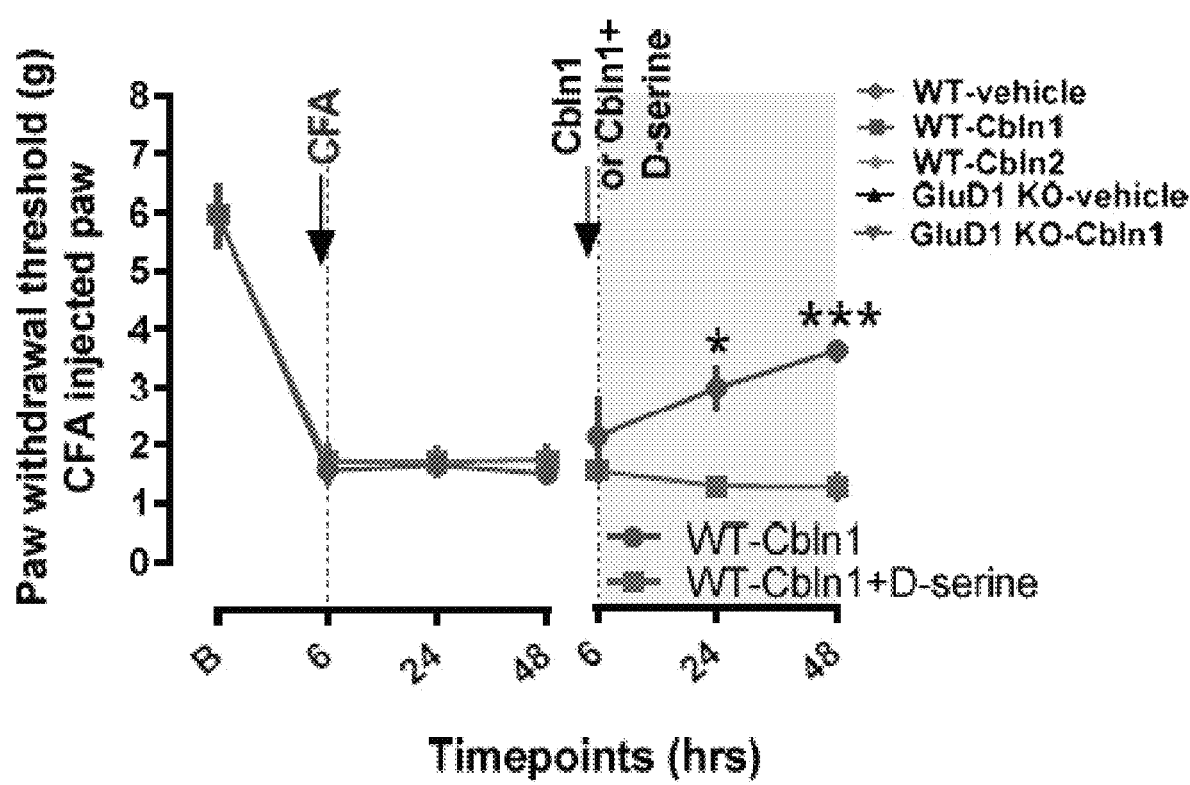
FIG. 16 is a plot showing D-serine (30 µg in 0.5 µl) opposes the anti-nociceptive effect of recombinant Cbln1 (250 ng in 0.5 µl). WT-Cbln1 vs. WT-Cbln1+D-serine; 24 hrs: 2.974±0.392 vs. 1.287±0.171, p=0.0112; 48 hrs: 3.627±0.190 vs. 1.266±0.234, p=0.0006; Two way ANOVA with Bonferroni's post hoc test, n=4 mice per group.

Recombinant Cbln1 Rescues Mechanical Hypersensitivity in an Inflammatory Pain Model with a Unique Time Course Whether restoring the GluD1-Cbln1 signaling using recombinant Cbln1 could mitigate chronic pain was tested. FIG. 13 has a schematic of experimental interventions. Mice underwent intracranial surgery for implantation of bilateral CeA cannulae. After recovery mechanical sensitivity was tested using Von Frey test for paw withdrawal threshold under baseline condition followed by intraplantar injection of CFA. Effect of intra-CeA administration of Cbln1 (250 ng in 0.5 µl per side) was assessed. Paw withdrawal threshold following Cbln1 injection was measured at 6, 24, 48, 72, 96 hrs and 1-week timepoints. Thereafter, the CFA model of inflammatory pain was induced. Bilateral injection of recombinant Cbln1 into the CeA mitigated mechanical hypersensitivity (FIG. 14). The antinociceptive effect gradually increased over the course of one week. Cbln1 was ineffective in mitigating hypersensitivity in GluD1 KO demonstrating the requirement for GluD1-Cbln1 signaling (FIG. 14). Cbln2 is another member of the cerebellin family of proteins with synaptogenic activity (Yuzaki. Curr. Opin. Neurobiol. 2017; 45:9-15). Intra-CeA Cbln2 administration was ineffective in producing antinociceptive effects demonstrating selectivity and a unique role of Cbln1 versus Cbln2 in the modulation of PB-CeLC synapses (FIG. 14). Whether rescue by recombinant Cbln1 shows lateralization was also examined. Injection of Cbln1 into the right, but not the left, CeA was sufficient to mitigate mechanical hypersensitivity in the inflammatory pain model (FIG. 15). D-serine binds to the ligand-binding domain of GluDs and induces conformational changes (Naur et al. Proc. Natl. Acad. Sci. U.S.A. 2007; 104:14116-14121; Yadav et al. Brain Res. 2011; 1382:1-8). When administered together with Cbln1, it was found that D-serine reduced the anti-nociceptive effect of recombinant Cbln1 (FIG. 16), suggesting that D-serine-induced conformational changes may oppose the association of Cbln1 with GluD1.

Figure 17A:
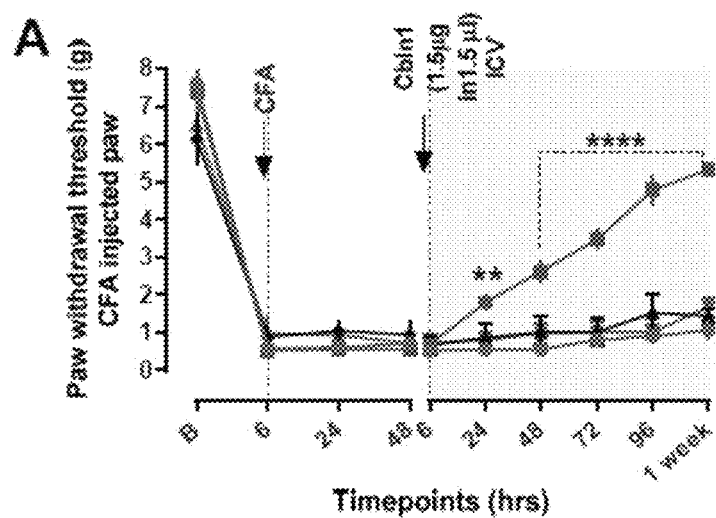
FIG. 17A is a plot showing intracerebroventricular administration of Cbln1 (1.5 in 1.5 µL PBS) 48 hrs after CFA also attenuated mechanical hypersensitivity for at least one week. WT CFA-vehicle vs. WT CFA-Cbln1; 24 hrs: 0.536±0.086 vs. 1.790±0.198, p=0.0014; 48 hrs: 0.544±0.112 vs. 2.623±0.294, p<0.0001; 72 hrs: 0.790±0.121 vs. 3.469±0.270, p<0.0001; 96 hrs: 0.890±0.022 vs. 4.788±0.401, p<0.0001 and 1 week: 1.059±0.254 vs. 5.331±0.177 p<0.0001; Two way ANOVA with Bonferroni's post hoc test, n=3-6 mice per group. No effect of Cbln1 was observed in GluD1 KO.
Figure 17B:
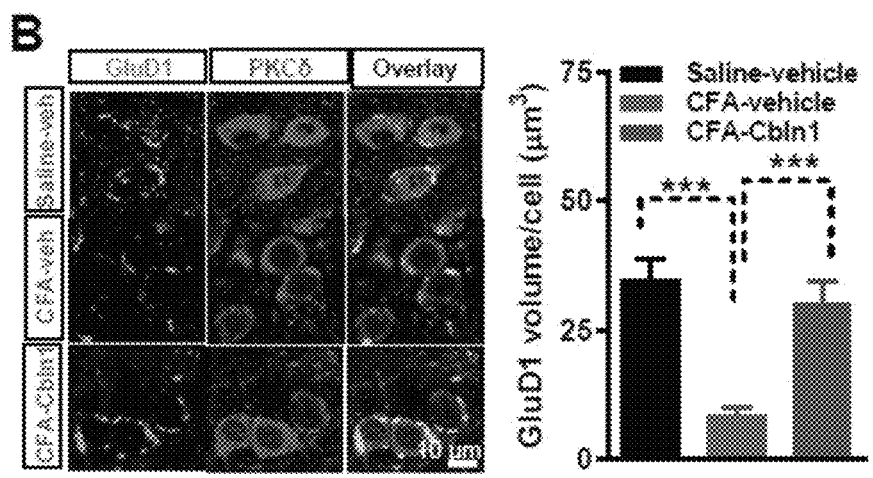
FIG. 17B is a plot showing immunohistochemical analysis of right CeLC for the effect of ICV administration of recombinant Cbln1 on perisomatic GluD1 volume in the CFA pain model. Recombinant Cbln1 restored GluD1 levels in CFA mice compared to mice injected with PBS (One-way ANOVA p<0.0001; Saline-vehicle: 34.82±4.065, vs. CFA-vehicle: 8.577±1.307, p<0.0001; CFA-vehicle: 8.577±1.307 vs. CFA-Cbln1: 30.35±4.112, p=0.0002, Unpaired t-test, n=11-31 neurons from 3-4 mice per group.
Figure 17C:
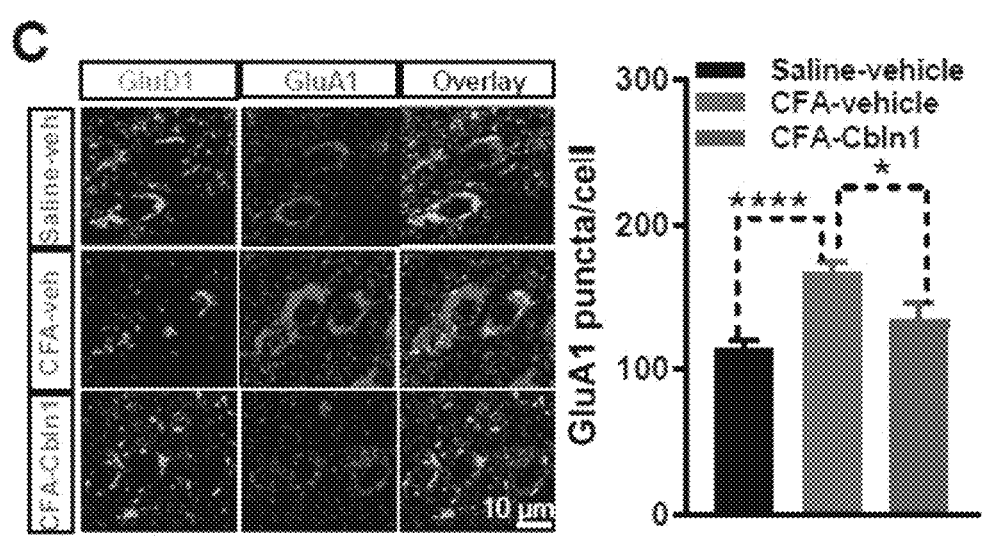
FIG. 17C is a plot showing recombinant Cbln1 normalized surface GluA1 upregulation in the right CeLC in CFA pain model (One-way ANOVA p<0.0001; Saline-vehicle vs. CFA-vehicle: 115.033±4.544 vs. 166.3±7.624, p<0.0001 and CFA-vehicle vs. CFA-Cbln1: 166.3±7.624 vs. 134.0±12.18, p=0.0412, Unpaired t-test, n=16-54 neurons from 3-4 mice per group).
Figure 18:
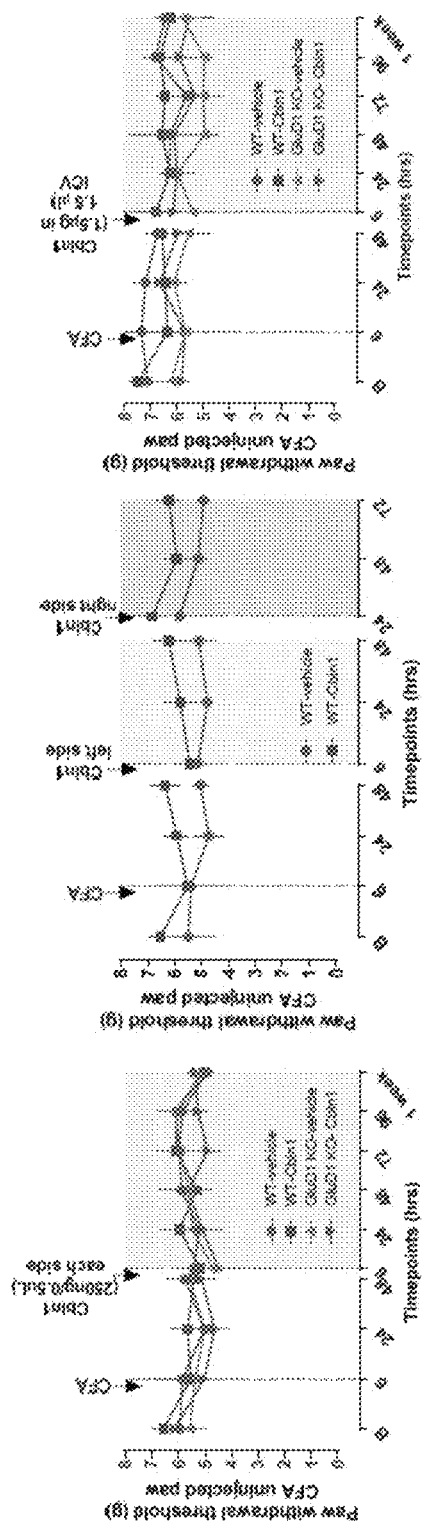
FIG. 18 is a plot
Figure 19:
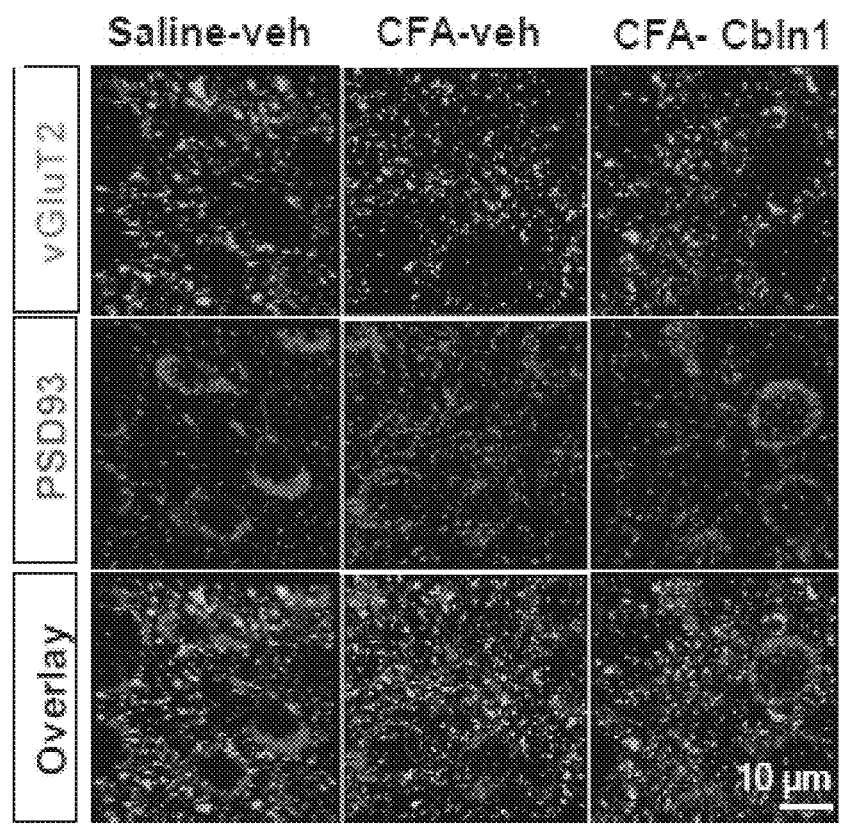
FIG. 19 has plots showing no change in number of excitatory synapse markers vGluT2 with PSD93 as assessed by immunohistochemistry (vGluT2: Saline-vehicle vs CFA-vehicle: 741.333±37.381 vs. 707.5±45.656, p=0.9226; CFA-vehicle vs. CFA-Cbln1: 707.5±45.656 vs. 861.333±86.426, p=0.2071; n=6 per group; Two way ANOVA with Bonferroni's multiple comparisons test; PSD93: Saline-vehicle vs CFA-vehicle: 261.833±36.981 vs. 167.833±62.437, p=0.5437; CFA-vehicle vs. WT-CFA-Cbln1: 167.833±62.437 vs. 287.667±84.987, p=0.3765; Two way ANOVA with Bonferroni's multiple comparisons test).
Figure 19:
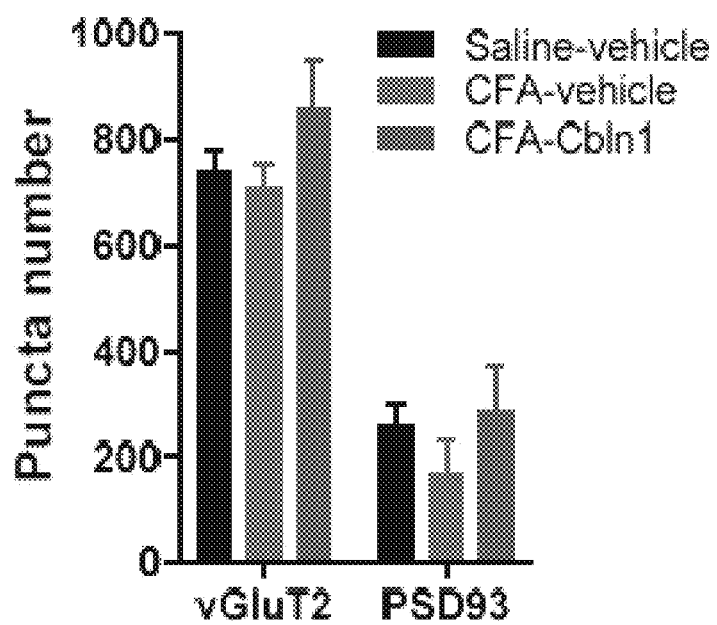
Figure 20:
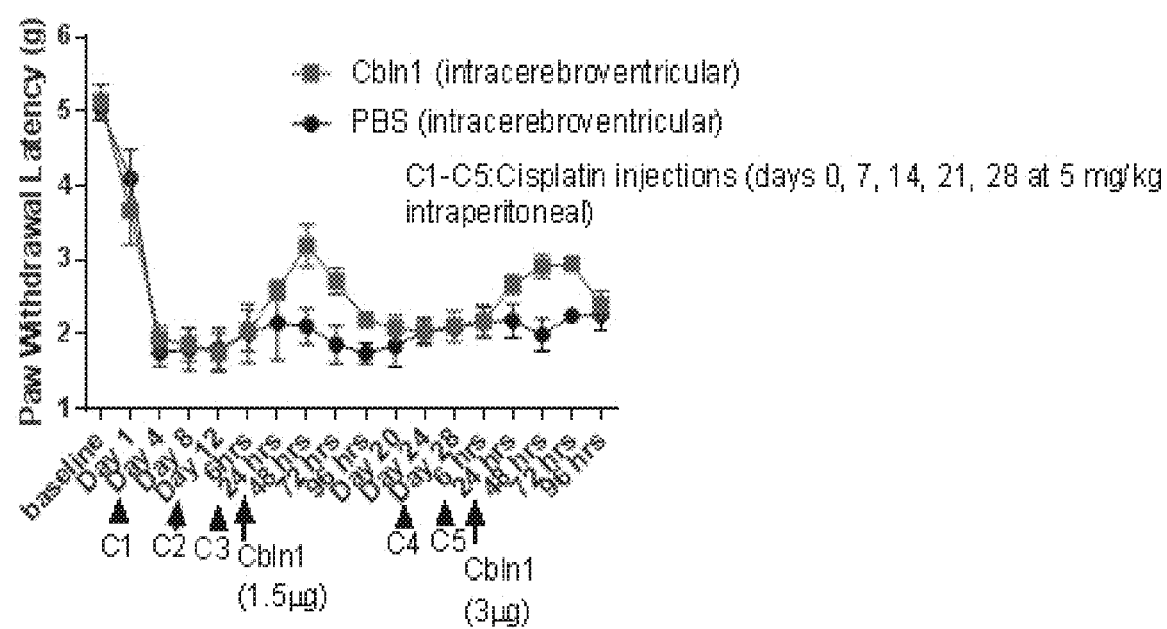
FIG. 20 is a plot showing the effect of recombinant Cbln1 on cisplatin-induced neuropathy.

Recombinant Cbln1 Normalizes Synapse Structure in the CeLC in Inflammatory Pain Model The effect of intracerebroventricular (ICV) injection of Cbln1 on mechanical hypersensitivity in the inflammatory pain model was examined since this may be relevant to clinical application as protein therapeutics. ICV injection of Cbln1 mitigated pain behavior in wildtype but not in GluD1 KO with a similar temporal profile as intra-CeA administration of Cbln1, pointing to the CeA as a major site of action (FIG. 17A). Furthermore, we found that recombinant Cbln1 was able to restore the downregulated GluD1 in the CeLC in the CFA model to levels similar to normal animals (FIG. 17B). Cbln1 also normalized the upregulated GluA1 in the CeLC in the pain model (FIG. 17C). No change in number of pre- and post-synaptic markers was observed in any of these groups (FIG. 19). These results demonstrate that recombinant Cbln1 is able to restore normal synaptic composition in the CeA in inflammatory pain conditions.

Discussion

The amygdala and its central nucleus has been identified as a key brain structure important for both the nocifensive and averse-affective behaviors in various pain conditions.

Pain-related neuroplasticity involving glutamatergic and neuropeptide systems has been observed consistently (see, e.g., Neugebauer et al. J. Neurosci. 2003; 23:52-63). More recently, cell-type specific details of the CeA circuitry and their roles in nociception have been emerging (see, e.g., Li et al. Pain; 2019). The results described here reveal a novel structural mechanism mediated by the GluD1-Cbln1 trans-synaptic signaling complex in the functional integrity of the PB-CeLC pathway; its dysregulation was found to underlie pain-related behaviors. The PB-CeLC synapses are structurally unique in that they have basket-like perisomatic organization in addition to the punctate elements. It was found that GluD1 expresses as perisomatic structures in the CeCL and is absent in CeM. Consistent with the expression of the GluD1's tripartite partner Cbln1 in PB neurons, GluD1 was found to localize preferentially at vGluT2 terminals, which primarily arise from PB as opposed to vGluT1 terminals which primarily arise from BLA (Lein et al. Nature. 2007; 445:168-176). Moreover, GluD1 localized postsynaptically to CGRP terminals, which are known to arise from PB. In addition to input-specificity, GluD1 also showed cell-type specificity with expression in PKCδ+ neurons compared to SOM+ neurons. The perisomatic and punctate elements of GluD1 were found on cell soma and punctate elements of PKCδ+ neurons. Previous studies have demonstrated that the GluDs have important roles in the organization of postsynaptic proteins via their C-terminal interactions (Yuzaki et al. Trends Neurosci. 2017; 40:138-150; Yuzaki. Annu. Rev. Physiol. 2017). Thus, the input- and cell-type specificity of GluD1 may impart unique characteristics to these synapses relevant to normal physiology as well as pain condition. Here, it was found that GluD1 is critical for the normal functioning of PB-CeLC synapses. CeC neurons in GluD1 KO mice had lower mEPSC frequency and amplitude and the neurotransmission at PB-CeC was reduced. In addition, there was a significant reduction in the vGluT2+ and CGRP+ terminals in the CeLC of GluD1 KO suggesting reduced number of PB-CeLC synapses.

In both inflammatory and neuropathic pain conditions, a reduction in the perisomatic as well as punctate GluD1 was found. Furthermore, a reduction in Cbln1 puncta was also found. The reduced expression was observed at 6 hours, the earliest time point tested, and sustained for 1 week in the inflammatory pain model. The reduction in GluD1 was more prominent in the right CeLC and the reduction was strong at the 6 hour time point and sustained thereafter. In contrast, reduction in Cbln1 puncta co-localized with GluD1 steadily declined over the 1 week period, and although the reduction was significant in the right CeLC, a trend in reduction was also observed in the left CeLC. The downregulation of GluD1 was also observed in a neuropathic pain model and was more prominent in the right CeLC. In contrast, AMPA receptor subunit GluA1 increased in both inflammatory and neuropathic pain models consistent with previous findings of neuroplasticity of PB-CeLC pathway. However, this effect did not show lateralization. Pain related changes in molecules regulating synapse structure has not been studied previously in the amygdala. However, in the spinal cord, pain related changes in neurexin and neuroligin complexes have been observed (see, e.g., Zhao et al. Neuroscience. 2018; 388:1-10). An increase in these molecules is observed in inflammatory and neuropathic pain. It has previously been shown that there is a switch in the neurexin splice variant in response to synaptic activity (Iijima et al. Cell. 2011; 147:1601-1614; Iijima et al. J. Neurosci. 2009; 29:5425-5434). Specifically, an increase in synaptic activity was found to reduce the S4+ splice variant which interacts with Cbln1. Thus, it is conceivable that pain related changes in the neurexin splice variants may contribute to changes in Cbln1 and GluD1 expression.

It was found that a single intra-CeA injection of recombinant Cbln1 reversed mechanical hypersensitivity in the inflammatory pain model. This effect had a time course of several days and the reversal persisted for at least 1 week. This time course supports a model in which recombinant Cbln1 normalizes the synapse structure rather than producing only an acute effect. In the GluD1 KO, Cbln1 was ineffective in reversing mechanical hypersensitivity, demonstrating a requirement for GluD1-Cbln1 signaling in this behavioral effect. Cbln2 did not produce similar effect as Cbln1, which is consistent with lower affinity of Cbln2 for GluD1 (Wei et al. J. Neurochem. 2012; 121:717-729). Consistent with the lateralization of downregulation of GluD1, recombinant Cbln1 effect on mechanical hypersensitivity in the inflammatory pain model showed right side lateralization. Furthermore, injection of recombinant Cbln1 into the right CeA was effective in mitigating audible and vocalization, mechanical hypersensitivity and anxiety-like behavior in a neuropathic pain model. It was also found that D-serine prevented the antinociceptive effect of Cbln1 in the inflammatory pain model. Although GluDs do not exhibit typical ligand-gated ion channel currents, binding of D-serine to GluDs is known to induce conformational changes (Naur et al. Proc Natl Acad Sci USA. 2007 Aug. 28; 104(35):14116-21; Yaday. Brain Res. 2011; 1382:1-8). Further, we found that exogenous Cbln1 restored the downregulated GluD1 and the upregulated GluA1 in both inflammatory and neuropathic pain models. This finding together with the absence of behavioral effect of Cbln1 in GluD1 KO mice demonstrates that Cbln1 acts by restoring GluD1 expression. It was also found that recombinant Cbln1 restored the hyperexcitability of CeC neurons in the neuropathic pain model, suggesting that normalization of GluD1 also restores intrinsic property of CeC neurons, supporting a structural role and ability to organize postsynaptic proteins.

The potential role of PKCδ+ neurons was addressed, which showed expression of GluD1 and downregulation of GluD1 in pain condition. Recently, the roles of PKCδ+ and SOM+ neurons were addressed in a neuropathic pain model (Wilson et al. Cell Rep. 2019 Oct. 8; 29(2):332-346.e5). In the pain state, hyperexcitability was noted specifically in the CeLC PKCδ+ neuron subtype that shows a late firing pattern (Wilson et al. Cell Rep. 2019 Oct. 8; 29(2):332-346.e5). Furthermore, in late firing and presumable PKCδ+ neurons an increase in PB-CeLC neurotransmission (Sugimura et al. J Neurophysiol. 2016 Jun. 1; 115(6):2721-39) and presynaptic release probability was noted (Li and Sheets. Pain. 2019). In contrast, no change in the excitability (Wilson et al. Cell Rep. 2019 Oct. 8; 29(2):332-346.e5), but a decrease in synaptic efficacy (Li and Sheets. Pain. 2019) was found in CeLC SOM+ neurons. Chemogenetic inhibition of PKCδ+ neurons mitigated pain behaviors, whereas activation of these neurons produced pain-like behaviors in normal animals (Wilson et al. Cell Rep. 2019 Oct. 8; 29(2):332-346.e5). In agreement with these findings, it was found that inhibition of PKCδ+ neurons mitigated mechanical hypersensitivity in an inflammatory pain model. Pain behaviors in GluD1 KO mice and in mice with partial ablation of GluD1 from PKCδ+ neurons were also evaluated. No difference in basal pain sensitivity was observed in these models. GluD1 KO mice also did not exhibit differences in CFA-induced mechanical hypersensitivity, suggesting that GluD1 is not critical for the acute stage or induction of pain. Instead, the loss of antinociceptive effects of Cbln1 in GluD1 KO suggests a requirement of GluD1 for recovery from pain progression. It was also found that GluD1-Cbln1 signaling in the CeA is critical for averse learning. Deletion of GluD1 from CeA reduced fear learning, which is consistent with the fear-conditioning deficit observed in GluD1 KO mice (Yadav et al. PLoS One, 2013; e60785). In addition, conditional deletion of Cbln1 also results in fear learning deficit (Otsuka et al. J. Neurosci. 2016; 36:11801-11816). Thus, Cbln1 release and binding to GluD1 may initiate fear learning. Interestingly, injection of recombinant Cbln1 in the CeA induced mechanical hypersensitivity in normal animals, which was absent in GluD1 KO. Intra-CeA Cbln1 also induced place aversion behavior and led to a downregulation of GluD1 similar to changes observed in pain models. Thus, GluD1-Cbln1 complex initiates a unique structural signaling in normal animals that may lead to bidirectional changes in postsynaptic composition, neuronal responsiveness and behavior. GluD1-Cbln1 signaling may serve as a survival mechanism in normal animals and dysregulation of this signaling induces chronic pain. This study has identified recombinant Cbln1 and GluD1-Cbln1 signaling as a novel mechanism of pain-related amygdala plasticity that can be targeted to restore synaptic function in chronic pain.

Example 2. Effect of Recombinant Cbln1 on Cisplatin-Induced Neuropathy

Effect of intracerebroventricular injection of recombinant Cbln1 on anticancer drug cisplatin induced neuropathic pain. Baseline readings of mechanical sensitivity were taken using Von Frey filament test. Thereafter, cisplatin (5 mg/kg, intraperitoneally) was injected on day 0, day 7 and day 14. Cisplatin-induced neuropathy was evident as a reduction in paw withdrawal threshold. Thereafter, the effect of intracerebroventricular injection of recombinant Cbln1 (1.5 µg in 1.5 µl of PBS, N=5) or vehicle (PBS, N=4) was evaluated. Cbln1 reduced mechanical hypersensitivity as evident by an increase in threshold for paw withdrawal in the Von Frey test for up to 3 days of injection. A higher dose of Cbln1 was tested after cisplatin injections on day 21 and 28. Cbln1 (3 µg in 1.5 µl of PBS) also reduced mechanical hypersensitivity for up to 3 days in the cisplatin-induced neuropathy model (FIG. 31). Thus, Cbln1 reduces pain in cisplatin-induced neuropathy model for up to 3 days after a single injection.

Other Embodiments

It is to be understood that while the invention has been described in conjunction with the detailed description thereof, the foregoing description is intended to illustrate and not limit the scope of the invention which is defined by the scope of the appended claims. Other aspects, advantages, and modification are within the scope of the following claims.

---

What is claimed is:

1. A method of treating pain in a subject in need thereof, the method comprising administering to the subject a therapeutically effective amount of a polypeptide having the amino acid sequence shown in to SEQ ID NO: 2, or a pharmaceutical composition thereof.

2. The method of claim 1, wherein administration of the polypeptide or a pharmaceutical composition thereof increases glutamate delta 1 receptor (GluD1)-cerebellin 1 (Cbln1) signaling.

3. A method of increasing GluD1-Cbln1 signaling in a subject in need thereof, the method comprising administering to the subject a polypeptide having the amino acid sequence shown in SEQ ID NO:2, or a pharmaceutical composition thereof.

4. The method of claim 1, wherein the pain comprises neuropathic pain.

5. The method of claim 4, wherein the neuropathic pain is associated with nerve compression, nerve damage, abnormal processing of pain signals, or a combination thereof.

6. The method of claim 4, wherein the neuropathic pain is a side effect of a therapeutic agent.

7. The method of claim 6, wherein the therapeutic agent is a chemotherapy.

8. The method of claim 7, wherein the chemotherapy comprises a taxane, a platinum-based agent, a *vinca* alkaloid, an epothilone, eribulin, bortezomib, thalidomide, or a combination thereof.

9. The method of claim 1, wherein the subject has chemotherapy-induced neuropathic pain.

10. The method of claim 1, wherein the pain comprises inflammatory pain.

11. The method of claim 10, wherein the inflammatory pain is associated with surgery, trauma, arthritis, or a combination thereof.

12. The method of claim 1, wherein the polypeptide or a pharmaceutical composition thereof is administered to the central nervous system of the subject.

13. A method of reducing an amount of opioid administered to a subject, the method comprising administering to the subject a therapeutically effective amount of a polypeptide having the amino acid sequence shown in SEQ ID NO: 2, or a pharmaceutical composition thereof.

* * * * *

UNITED STATES PATENT AND TRADEMARK OFFICE
CERTIFICATE OF CORRECTION

| | | |
|---|---|---|
| PATENT NO. | : 12,246,058 B2 | Page 1 of 1 |
| APPLICATION NO. | : 17/153165 | |
| DATED | : March 11, 2025 | |
| INVENTOR(S) | : Shashank Dravid | |

It is certified that error appears in the above-identified patent and that said Letters Patent is hereby corrected as shown below:

On the Title Page

Column 1, Other Publications, Line 11, delete "signalingand" and insert -- signaling and --.

In the Claims

Claim 1, Column 53, Line 14, before "SEQ" delete "to".

Signed and Sealed this
Twenty-ninth Day of April, 2025

Coke Morgan Stewart
*Acting Director of the United States Patent and Trademark Office*

SEQUENCE LISTING

```
<160> NUMBER OF SEQ ID NOS: 12

<210> SEQ ID NO 1
<211> LENGTH: 193
<212> TYPE: PRT
<213> ORGANISM: Homo sapiens

<400> SEQUENCE: 1

Met Leu Gly Val Leu Glu Leu Leu Leu Gly Ala Ala Trp Leu Ala
1               5                   10                  15

Gly Pro Ala Arg Gly Gln Asn Glu Thr Glu Pro Ile Val Leu Glu Gly
            20                  25                  30

Lys Cys Leu Val Val Cys Asp Ser Asn Pro Thr Ser Asp Pro Thr Gly
            35                  40                  45

Thr Ala Leu Gly Ile Ser Val Arg Ser Gly Ser Ala Lys Val Ala Phe
        50                  55                  60

Ser Ala Ile Arg Ser Thr Asn His Glu Pro Ser Glu Met Ser Asn Arg
65                  70                  75                  80

Thr Met Ile Ile Tyr Phe Asp Gln Val Leu Val Asn Ile Gly Asn Asn
                85                  90                  95

Phe Asp Ser Glu Arg Ser Thr Phe Ile Ala Pro Arg Lys Gly Ile Tyr
            100                 105                 110

Ser Phe Asn Phe His Val Val Lys Val Tyr Asn Arg Gln Thr Ile Gln
        115                 120                 125

Val Ser Leu Met Leu Asn Gly Trp Pro Val Ile Ser Ala Phe Ala Gly
    130                 135                 140

Asp Gln Asp Val Thr Arg Glu Ala Ala Ser Asn Gly Val Leu Ile Gln
145                 150                 155                 160

Met Glu Lys Gly Asp Arg Ala Tyr Leu Lys Leu Glu Arg Gly Asn Leu
                165                 170                 175
```

```
Met Gly Gly Trp Lys Tyr Ser Thr Phe Ser Gly Phe Leu Val Phe Pro
            180                 185                 190

Leu

<210> SEQ ID NO 2
<211> LENGTH: 172
<212> TYPE: PRT
<213> ORGANISM: Homo sapiens

<400> SEQUENCE: 2

Gln Asn Glu Thr Glu Pro Ile Val Leu Glu Gly Lys Cys Leu Val Val
1               5                   10                  15

Cys Asp Ser Asn Pro Thr Ser Asp Pro Thr Gly Thr Ala Leu Gly Ile
            20                  25                  30

Ser Val Arg Ser Gly Ser Ala Lys Val Ala Phe Ser Ala Ile Arg Ser
        35                  40                  45

Thr Asn His Glu Pro Ser Glu Met Ser Asn Arg Thr Met Ile Ile Tyr
    50                  55                  60

Phe Asp Gln Val Leu Val Asn Ile Gly Asn Asn Phe Asp Ser Glu Arg
65                  70                  75                  80

Ser Thr Phe Ile Ala Pro Arg Lys Gly Ile Tyr Ser Phe Asn Phe His
                85                  90                  95

Val Val Lys Val Tyr Asn Arg Gln Thr Ile Gln Val Ser Leu Met Leu
            100                 105                 110

Asn Gly Trp Pro Val Ile Ser Ala Phe Ala Gly Asp Gln Asp Val Thr
        115                 120                 125

Arg Glu Ala Ala Ser Asn Gly Val Leu Ile Gln Met Glu Lys Gly Asp
    130                 135                 140

Arg Ala Tyr Leu Lys Leu Glu Arg Gly Asn Leu Met Gly Gly Trp Lys
145                 150                 155                 160

Tyr Ser Thr Phe Ser Gly Phe Leu Val Phe Pro Leu
                165                 170

<210> SEQ ID NO 3
<211> LENGTH: 193
<212> TYPE: PRT
<213> ORGANISM: Homo sapiens

<400> SEQUENCE: 3

Met Leu Gly Val Leu Glu Leu Leu Leu Gly Ala Ala Trp Leu Ala
1               5                   10                  15

Gly Pro Ala Arg Gly Gln Asn Glu Thr Glu Pro Ile Val Leu Glu Gly
            20                  25                  30

Lys Cys Leu Val Val Cys Asp Ser Asn Pro Thr Ser Asp Pro Thr Gly
        35                  40                  45

Thr Ala Leu Gly Ile Ser Val Arg Ser Gly Ser Ala Lys Val Ala Phe
    50                  55                  60

Ser Ala Ile Arg Ser Thr Asn His Glu Pro Ser Glu Met Ser Asn Arg
65                  70                  75                  80

Thr Met Ile Ile Tyr Phe Asp Gln Val Leu Val Asn Ile Gly Asn Asn
                85                  90                  95

Phe Asp Ser Glu Arg Ser Thr Phe Ile Ala Pro Arg Lys Gly Ile Tyr
            100                 105                 110

Ser Phe Asn Phe His Val Val Lys Val Asp Asn Arg Gln Thr Ile Gln
        115                 120                 125

Val Ser Leu Met Leu Asn Gly Trp Pro Val Ile Ser Ala Phe Ala Gly
```

```
            130                 135                 140
Asp Gln Asp Val Thr Arg Glu Ala Ala Ser Asn Gly Val Leu Ile Gln
145                 150                 155                 160

Met Glu Lys Gly Asp Arg Ala Tyr Leu Lys Leu Glu Arg Gly Asn Leu
                165                 170                 175

Met Gly Gly Trp Lys Tyr Ser Thr Phe Ser Gly Phe Leu Val Phe Pro
            180                 185                 190

Leu

<210> SEQ ID NO 4
<211> LENGTH: 193
<212> TYPE: PRT
<213> ORGANISM: Homo sapiens

<400> SEQUENCE: 4

Met Leu Gly Val Leu Glu Leu Leu Leu Gly Ala Ala Trp Leu Ala
1               5                   10                  15

Gly Pro Ala Arg Gly Gln Asn Glu Thr Glu Pro Ile Val Leu Glu Gly
                20                  25                  30

Lys Cys Leu Val Val Cys Asp Ser Asn Pro Thr Ser Asp Pro Thr Gly
            35                  40                  45

Thr Ala Leu Gly Ile Ser Val Arg Ser Gly Ser Ala Lys Val Ala Phe
    50                  55                  60

Ser Ala Ile Arg Ser Thr Asn His Glu Pro Ser Glu Met Ser Asn Arg
65                  70                  75                  80

Thr Met Ile Ile Tyr Phe Asp Gln Val Leu Val Asn Ile Gly Asn Asn
                85                  90                  95

Phe Asp Ser Glu Arg Ser Thr Phe Ile Ala Pro Arg Lys Gly Ile Tyr
                100                 105                 110

Ser Phe Asn Phe His Val Val Lys Val Glu Asn Arg Gln Thr Ile Gln
            115                 120                 125

Val Ser Leu Met Leu Asn Gly Trp Pro Val Ile Ser Ala Phe Ala Gly
            130                 135                 140

Asp Gln Asp Val Thr Arg Glu Ala Ala Ser Asn Gly Val Leu Ile Gln
145                 150                 155                 160

Met Glu Lys Gly Asp Arg Ala Tyr Leu Lys Leu Glu Arg Gly Asn Leu
                165                 170                 175

Met Gly Gly Trp Lys Tyr Ser Thr Phe Ser Gly Phe Leu Val Phe Pro
            180                 185                 190

Leu

<210> SEQ ID NO 5
<211> LENGTH: 193
<212> TYPE: PRT
<213> ORGANISM: Homo sapiens

<400> SEQUENCE: 5

Met Leu Gly Val Leu Glu Leu Leu Leu Gly Ala Ala Trp Leu Ala
1               5                   10                  15

Gly Pro Ala Arg Gly Gln Asn Glu Thr Glu Pro Ile Val Leu Glu Gly
                20                  25                  30

Lys Cys Leu Val Val Cys Asp Ser Asn Pro Thr Ser Asp Pro Thr Gly
            35                  40                  45

Thr Ala Leu Gly Ile Ser Val Arg Ser Gly Ser Ala Lys Val Ala Phe
    50                  55                  60
```

```
Ser Ala Ile Arg Ser Thr Asn His Glu Pro Ser Glu Met Ser Asn Arg
 65                  70                  75                  80

Thr Met Ile Ile Tyr Phe Asp Gln Val Leu Val Asn Ile Gly Asn Asn
                 85                  90                  95

Phe Asp Ser Glu Arg Ser Thr Phe Ile Ala Pro Arg Lys Gly Ile Tyr
            100                 105                 110

Ser Phe Asn Phe His Val Val Lys Val Glu Asn Lys Gln Thr Ile Gln
        115                 120                 125

Val Ser Leu Met Leu Asn Gly Trp Pro Val Ile Ser Ala Phe Ala Gly
    130                 135                 140

Asp Gln Asp Val Thr Arg Glu Ala Ala Ser Asn Gly Val Leu Ile Gln
145                 150                 155                 160

Met Glu Lys Gly Asp Arg Ala Tyr Leu Lys Leu Glu Arg Gly Asn Leu
                165                 170                 175

Met Gly Gly Trp Lys Tyr Ser Thr Phe Ser Gly Phe Leu Val Phe Pro
            180                 185                 190

Leu

<210> SEQ ID NO 6
<211> LENGTH: 193
<212> TYPE: PRT
<213> ORGANISM: Homo sapiens

<400> SEQUENCE: 6

Met Leu Gly Val Leu Glu Leu Leu Leu Gly Ala Ala Trp Leu Ala
 1               5                  10                  15

Gly Pro Ala Arg Gly Gln Asn Glu Thr Glu Pro Ile Val Leu Glu Gly
                 20                  25                  30

Lys Cys Leu Val Val Cys Asp Ser Asn Pro Thr Ser Asp Pro Thr Gly
             35                  40                  45

Thr Ala Leu Gly Ile Ser Val Arg Ser Gly Ser Ala Lys Val Ala Phe
     50                  55                  60

Ser Ala Ile Arg Ser Thr Asn His Glu Pro Ser Glu Met Ser Asn Arg
 65                  70                  75                  80

Thr Met Ile Ile Tyr Phe Asp Gln Val Leu Val Asn Ile Gly Asn Asn
                 85                  90                  95

Phe Asp Ser Glu Arg Ser Thr Phe Ile Ala Pro Arg Lys Gly Ile Tyr
            100                 105                 110

Ser Phe Asn Phe His Val Val Lys Val Glu Asn Arg Gln Thr Ile Gln
        115                 120                 125

Val Ser Leu Met Leu Asn Gly Trp Pro Val Ile Ser Ala Phe Ala Gly
    130                 135                 140

Asp Gln Glu Val Thr Arg Glu Ala Ala Ser Asn Gly Val Leu Ile Gln
145                 150                 155                 160

Met Glu Lys Gly Asp Arg Ala Tyr Leu Lys Leu Glu Arg Gly Asn Leu
                165                 170                 175

Met Gly Gly Trp Lys Tyr Ser Thr Phe Ser Gly Phe Leu Val Phe Pro
            180                 185                 190

Leu

<210> SEQ ID NO 7
<211> LENGTH: 582
<212> TYPE: DNA
<213> ORGANISM: Homo sapiens

<400> SEQUENCE: 7
```

```
atgctgggcg tcctggagct gctgctgctg ggggctgcgt ggctggcggg cccggcccgc    60
gggcagaatg agacggagcc catcgtgctg gagggcaagt gcctggtggt gtgcgactcc   120
aaccccacgt ccgacccccac gggcactgcc ctgggcatct ctgtgcgctc tggcagcgcc   180
aaggtggctt tctctgccat caggagcacc aaccacgagc cgtccgagat gagtaatcgc   240
accatgatca tctacttcga ccaggtacta gtgaacattg gaacaacctt tgattcagaa   300
cgcagcactt tcatcgcccc cgcgcaaaggg atctacagtt taacttcca cgtggtaaaa   360 gtctacaaca gacaaaccat acaggtgagc ctcatgctaa acgggtggcc ggtgatttca   420
gccttcgctg gtgaccagga cgtgacccgg gaggccgcca gcaacggagt cctaatccaa   480
atggagaaag gcgaccgagc atacctcaag ctggagcggg aaacttgat ggggggctgg    540 aagtactcga ccttctccgg attcctggtg tttcctctct ga                     582

<210> SEQ ID NO 8
<211> LENGTH: 519
<212> TYPE: DNA
<213> ORGANISM: Homo sapiens

<400> SEQUENCE: 8
cagaatgaga cggagcccat cgtgctggag ggcaagtgcc tggtggtgtg cgactccaac    60
cccacgtccg accccacggg cactgccctg gcatctctg tgcgctctgg cagcgccaag   120
gtggctttct ctgccatcag gagcaccaac cacgagccgt ccgagatgag taatcgcacc   180
atgatcatct acttcgacca ggtactagtg aacattggga caactttga ttcagaacgc    240 agcactttca tcgccccgcg caaagggatc tacagtttta acttccacgt ggtaaaagtc   300
tacaacagac aaaccataca ggtgagcctc atgctaaacg gtggccggt gatttcagcc    360 ttcgctggtg accaggacgt gacccgggag gccgccagca acggagtcct aatccaaatg   420
gagaaaggcg accgagcata cctcaagctg gagcggggaa acttgatggg gggctggaag   480
tactcgacct tctccggatt cctggtgttt cctctctga                          519

<210> SEQ ID NO 9
<211> LENGTH: 582
<212> TYPE: DNA
<213> ORGANISM: Homo sapiens

<400> SEQUENCE: 9
atgctgggcg tcctggagct gctgctgctg ggggctgcgt ggctggcggg cccggcccgc    60
gggcagaatg agacggagcc catcgtgctg gagggcaagt gcctggtggt gtgcgactcc   120
aaccccacgt ccgaccccac gggcactgcc ctgggcatct ctgtgcgctc tggcagcgcc   180
aaggtggctt tctctgccat caggagcacc aaccacgagc cgtccgagat gagtaatcgc   240
accatgatca tctacttcga ccaggtacta gtgaacattg gaacaacctt tgattcagaa   300
cgcagcactt tcatcgcccc cgcgcaaaggg atctacagtt taacttcca cgtggtaaaa   360 gtcgacaaca gacaaaccat acaggtgagc ctcatgctaa acgggtggcc ggtgatttca   420
gccttcgctg gtgaccagga cgtgacccgg gaggccgcca gcaacggagt cctaatccaa   480
atggagaaag gcgaccgagc atacctcaag ctggagcggg aaacttgat ggggggctgg    540 aagtactcga ccttctccgg attcctggtg tttcctctct ga                     582

<210> SEQ ID NO 10
<211> LENGTH: 582
<212> TYPE: DNA
```

<213> ORGANISM: Homo sapiens

<400> SEQUENCE: 10

| | |
|---|---|
| atgctgggcg tcctggagct gctgctgctg ggggctgcgt ggctggcggg cccggcccgc | 60 |
| gggcagaatg agacggagcc catcgtgctg gagggcaagt gcctggtggt gtgcgactcc | 120 |
| aaccccacgt ccgaccccac gggcactgcc ctgggcatct ctgtgcgctc tggcagcgcc | 180 |
| aaggtggctt tctctgccat caggagcacc aaccacgagc cgtccgagat gagtaatcgc | 240 |
| accatgatca tctacttcga ccaggtacta gtgaacattg gaacaacttt tgattcagaa | 300 |
| cgcagcactt tcatcgcccc gcgcaaaggg atctacagtt ttaacttcca cgtggtaaaa | 360 |
| gtcgagaaca gacaaaccat acaggtgagc ctcatgctaa cgggtggcc ggtgatttca | 420 |
| gccttcgctg gtgaccagga cgtgacccgg gaggccgcca gcaacggagt cctaatccaa | 480 |
| atggagaaag gcgaccgagc atacctcaag ctggagcggg gaaacttgat gggggctgg | 540 |
| aagtactcga ccttctccgg attcctggtg tttcctctct ga | 582 |

<210> SEQ ID NO 11
<211> LENGTH: 582
<212> TYPE: DNA
<213> ORGANISM: Homo sapiens

<400> SEQUENCE: 11

| | |
|---|---|
| atgctgggcg tcctggagct gctgctgctg ggggctgcgt ggctggcggg cccggcccgc | 60 |
| gggcagaatg agacggagcc catcgtgctg gagggcaagt gcctggtggt gtgcgactcc | 120 |
| aaccccacgt ccgaccccac gggcactgcc ctgggcatct ctgtgcgctc tggcagcgcc | 180 |
| aaggtggctt tctctgccat caggagcacc aaccacgagc cgtccgagat gagtaatcgc | 240 |
| accatgatca tctacttcga ccaggtacta gtgaacattg gaacaacttt tgattcagaa | 300 |
| cgcagcactt tcatcgcccc gcgcaaaggg atctacagtt ttaacttcca cgtggtaaaa | 360 |
| gtcgagaaca aacaaaccat acaggtgagc ctcatgctaa cgggtggcc ggtgatttca | 420 |
| gccttcgctg gtgaccagga cgtgacccgg gaggccgcca gcaacggagt cctaatccaa | 480 |
| atggagaaag gcgaccgagc atacctcaag ctggagcggg gaaacttgat gggggctgg | 540 |
| aagtactcga ccttctccgg attcctggtg tttcctctct ga | 582 |

<210> SEQ ID NO 12
<211> LENGTH: 582
<212> TYPE: DNA
<213> ORGANISM: Homo sapiens

<400> SEQUENCE: 12

| | |
|---|---|
| atgctgggcg tcctggagct gctgctgctg ggggctgcgt ggctggcggg cccggcccgc | 60 |
| gggcagaatg agacggagcc catcgtgctg gagggcaagt gcctggtggt gtgcgactcc | 120 |
| aaccccacgt ccgaccccac gggcactgcc ctgggcatct ctgtgcgctc tggcagcgcc | 180 |
| aaggtggctt tctctgccat caggagcacc aaccacgagc cgtccgagat gagtaatcgc | 240 |
| accatgatca tctacttcga ccaggtacta gtgaacattg gaacaacttt tgattcagaa | 300 |
| cgcagcactt tcatcgcccc gcgcaaaggg atctacagtt ttaacttcca cgtggtaaaa | 360 |
| gtcgagaaca gacaaaccat acaggtgagc ctcatgctaa cgggtggcc ggtgatttca | 420 |

```
gccttcgctg gtgaccagga ggtgacccgg gaggccgcca gcaacggagt cctaatccaa      480
atggagaaag gcgaccgagc atacctcaag ctggagcggg gaaacttgat gggggggctgg     540 aagtactcga ccttctccgg attcctggtg tttcctctct ga                        582
```